(12) United States Patent
Zheng et al.

(10) Patent No.: US 10,844,079 B2
(45) Date of Patent: Nov. 24, 2020

(54) SPIRO AROMATIC RING COMPOUND AND APPLICATION THEREOF

(71) Applicant: Etern Biopharma (Shanghai) Co., Ltd., Shanghai (CN)

(72) Inventors: Qiangang Zheng, Shanghai (CN); Ming Xu, Shanghai (CN); Qinglong Zeng, Shanghai (CN); Jing Li, Shanghai (CN); Hao Zhuge, Shanghai (CN)

(73) Assignee: Etern Biopharma (Shanghai) Co., Ltd., Shanghai (CN)

( * ) Notice: Subject to any disclaimer, the term of this patent is extended or adjusted under 35 U.S.C. 154(b) by 0 days.

(21) Appl. No.: 16/908,604

(22) Filed: Jun. 22, 2020

(65) Prior Publication Data

US 2020/0317695 A1 Oct. 8, 2020

Related U.S. Application Data

(63) Continuation of application No. PCT/CN2019/115754, filed on Nov. 5, 2019.

(30) Foreign Application Priority Data

Nov. 6, 2018 (CN) .......................... 2018 1 1314910

(51) Int. Cl.
*C07D 519/00* (2006.01)
(52) U.S. Cl.
CPC .................................. *C07D 519/00* (2013.01)
(58) Field of Classification Search
CPC .... A61K 31/519; A61K 45/06; C07D 519/00; C07D 487/04; C07D 471/04; C07D 471/10
See application file for complete search history.

(56) References Cited

U.S. PATENT DOCUMENTS

| | | | |
|---|---|---|---|
| 2017/0015680 A1 | 1/2017 | Chen et al. | |
| 2017/0204080 A1 | 7/2017 | Chen et al. | |
| 2020/0108071 A1* | 4/2020 | Chin ...................... | A61K 45/06 |

FOREIGN PATENT DOCUMENTS

| | | |
|---|---|---|
| CN | 105916845 A | 8/2016 |
| CN | 108341791 A | 7/2018 |
| CN | 105899491 A | 4/2019 |
| WO | WO 2015/107493 A1 | 7/2015 |
| WO | WO 2016/203404 A1 | 12/2016 |
| WO | WO 2016/203406 A1 | 12/2016 |
| WO | WO 2017/211303 A1 | 12/2017 |
| WO | WO 2017/216706 A1 | 12/2017 |
| WO | WO 2018057884 A1 | 3/2018 |
| WO | WO 2018/136265 A1 | 7/2018 |
| WO | WO 2018/172984 A1 | 9/2018 |
| WO | WO 2019/075265 A1 | 4/2019 |
| WO | WO 2019/118909 A1 | 6/2019 |
| WO | WO 2019/158019 A1 | 8/2019 |
| WO | WO 2019/183367 A1 | 9/2019 |
| WO | WO 2019/199792 A1 | 10/2019 |
| WO | WO 2020/063760 A1 | 4/2020 |
| WO | WO 2020/072656 A1 | 4/2020 |
| WO | WO 2020/094104 A1 | 5/2020 |
| WO | WO 2020/108590 A1 | 6/2020 |

OTHER PUBLICATIONS

Huang et al., "Discovery of First-in-Class, Potent, and Orally Bioavailable Embryonic Ectoderm Development (EED) Inhibitor With Robust Anticancer Efficacy," *J. Med. Chem.*, 60(6):2215-2226 (2017).

* cited by examiner

*Primary Examiner* — Erich A Leeser
(74) *Attorney, Agent, or Firm* — Jones Day

(57) ABSTRACT

Provided is a compound of formula I or a pharmaceutically acceptable salt, enantiomer, diastereomer, tautomer, solvate, isotopic substituent, polymorph, prodrug, or metabolite thereof. Also provided is a method for preparing the compound of formula I. The compound of formula I has higher inhibitory activity against SHP2, and thus can be used to prevent or treat a disease related to SHP2.

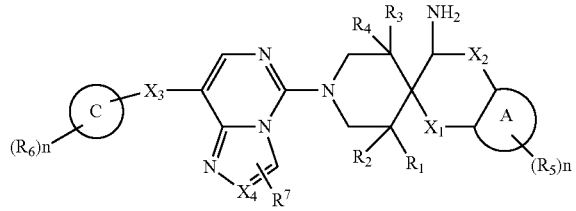

2 Claims, No Drawings

SPIRO AROMATIC RING COMPOUND AND APPLICATION THEREOF

CROSS REFERENCE TO RELATED APPLICATIONS

This application is a continuation under 35 U.S.C. § 120 of International Patent Application No. PCT/CN2019/115754, filed Nov. 5, 2019, which claims priority of Chinese Patent Application No. 201811314910.1, filed Nov. 6, 2018, the entirety of each of which is incorporated herein by reference.

TECHNICAL FIELD

This disclosure relates to spiro aromatic ring compounds. In particular, the disclosure relates to spiro aromatic ring compounds which can be used as an SHP2 inhibitor, the pharmaceutically acceptable salts thereof, or enantiomers, diastereoisomers, tautomers, solvates, isotope-substituted derivative, prodrugs or metabolites thereof. In addition, the disclosure also relates to methods for the preparation of the compounds, pharmaceutical compositions comprising the compounds and use of the compounds in the preparation of medicaments for the prevention or treatment of diseases or conditions related to abnormal SHP2 activity.

BACKGROUND

Protein tyrosine phosphatase SHP2 plays an important role in cell signaling and is a target for the treatment of major diseases such as diabetes, autoimmune diseases and cancers. SHP2 is mutated or highly expressed in various diseases, such as Noonan Syndrome, Leopard Syndrome, juvenile myelomonocytic leukemia, neuroblastoma, melanoma, acute myeloid leukemia, breast cancer, esophageal cancer, lung cancer, colon cancer, head cancer, neuroblastoma, squamous cell carcinoma of head and neck, gastric cancer, anaplastic large cell lymphoma, and glioblastoma, etc. Molecular biological studies show that SHP2 is involved in multiple tumor cell signaling pathways, such as MAPK, JAK/STAT, and PI3K/Akt, etc. At the same time, SHP2 is also responsible for the signal transduction of PD1-PDL1 immunosuppressive pathway. Therefore, inhibition of SHP2 activity can reverse immunosuppression in tumor microenvironment.

SHP2 consists of two N-terminal Src Homolgy-2 domains (N-SH2 and C-SH2) and a protein tyrosine phosphatase catalytic domain (PTP). In the self-inhibiting state, N-SH2 combines with PTP to form a ring structure, which hinders the binding of PTP to substrate, thus inhibiting the enzyme catalytic activity; when the tyrosine of an upstream receptor protein is phosphorylated and binds to N-SH2, PTP catalytic domain is released to exhibit phosphatase activity.

At present, the development of SHP2 inhibitors mainly focus on allosteric inhibitors in the non-catalytic region, such as the compounds disclosed in WO2015107493A1, WO2016203404A1, WO2016203406A1, WO2017216706A1, WO2017211303A1, CN201710062495, WO2018136265A1, WO2018057884, etc. This year's research shows that SHP2 as a novel drugable target has attracted more and more attention. Therefore, there is an urgent need in the art to develop SHP2 inhibitors with novel structures, good biological activity, and high druggability.

SUMMARY

One object of the disclosure is to provide a compound of Formula I or a pharmaceutically acceptable salt thereof, a pharmaceutical composition comprising the compound or the pharmaceutically acceptable salt thereof, and use of the compound or the pharmaceutical composition in the prevention or treatment of diseases or conditions related to abnormal SHP2 activity.

The first aspect of the disclosure provides a compound of Formula I:

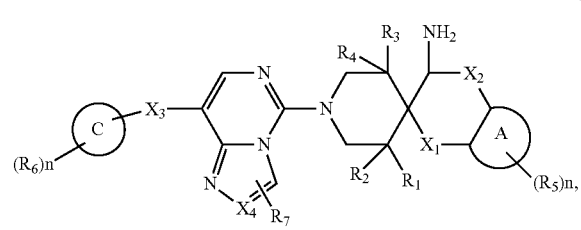

or a pharmaceutically acceptable salt thereof, or an enantiomer, diastereoisomer, tautomer, solvate, isotope-substituted derivative, polymorph, prodrug or metabolite thereof, wherein:

$X_1$ and $X_2$ are independently selected from a bond, O, $CR_aR_b$ or $NR_c$;

$X_3$ is selected from a bond, $CR_aR_b$, $NR_c$, S or O;

$X_4$ is selected from N or $CR_c$; and $R_a$, $R_b$ and $R_c$ are independently selected from H, halogen, substituted or unsubstituted $C_{1-6}$ alkyl, or substituted or unsubstituted $C_{1-6}$ alkoxyl;

$R_1$, $R_2$, $R_3$, $R_4$ and $R_7$ are independently selected from H, —OH, halogen, substituted or unsubstiuted amino, substituted or unsubstiuted $C_{1-6}$ alkyl, or substituted or unsubstiuted $C_{1-6}$ alkoxyl; and $R_1$, $R_2$, $R_3$, $R_4$ and $R_7$ cannot be —OH or —NH$_2$ simultaneously;

ring A is selected from substituted or unsubstiuted $C_{4-5}$ cyclic hydrocarbyl, substituted or unsubstiuted 4 to 8-membered heterocyclyl, substituted or unsubstiuted $C_{5-10}$ aryl, or substituted or unsubstiuted 5 to 10-membered heteroaryl, wherein the heterocyclyl or heteroaryl comprises 1-3 heteroatoms selected from the following atoms: N, O, S or P;

ring C is selected from substituted or unsubstiuted $C_{4-5}$ cyclic hydrocarbyl, substituted or unsubstiuted 5 to 6-membered monocyclic heterocyclyl, substituted or unsubstiuted 8 to 10-membered bicyclic heterocyclyl, substituted or unsubstiuted $C_{5-10}$ monocyclic or bicyclic aryl, substituted or unsubstiuted 5 to 6-membered monocyclic heteroaryl, or substituted or unsubstiuted 8 to 10-membered bicyclic heteroaryl, wherein the heterocyclyl or heteroaryl comprises 1-4 heteroatoms selected from the following atoms: N, O, S or P;

$R_5$ and $R_6$ are independently selected from H, —OH, halogen, cyano, substituted or unsubstiuted amino, substituted or unsubstiuted $C_{1-6}$ alkyl, or substituted or unsubstiuted $C_{1-6}$ alkoxyl;

n is any integer from 0 to 3; and the "substituted" refers to one or more hydrogen atoms on the group are substituted by a substituent selected from the following substituents: halogen, —OH, —NO$_2$, —NH$_2$, —NH(unsubstituted or halogenated $C_{1-6}$ alkyl), —N(unsubstituted or halogenated $C_{1-6}$ alkyl)$_2$, —CN, unsubstituted or halogenated $C_{1-8}$ alkyl, unsubstituted or halogenated $C_{1-8}$ alkoxyl, unsubstituted or halogenated $C_{1-8}$ alkoxyl-$C_{1-8}$ alkyl, unsubstituted or halogenated $C_{3-8}$ cycloalkyl-$C_{1-8}$ alkyl, unsubstituted or halogenated $C_{1-6}$ alkyl carbonyl, unsubstituted or halogenated $C_{1-6}$ alkoxyl carbonyl, hydroxamic acid group, unsubstituted or halogenated $C_{1-6}$ alkyl thiol, —S(O)$_2$N (unsubstituted or halogenated $C_{1-6}$ alkyl)$_2$, —S(O)$_2$ unsubstituted or halogenated $C_{1-6}$ alkyl, —N(unsubstituted or halogenated $C_{1-6}$ alkyl) S(O)$_2$N (unsubstituted or halogenated $C_{1-6}$ alkyl)$_2$, —S(O)N (unsubstituted or halogenated $C_{1-6}$ alkyl)$_2$, —S(O)(unsubstituted or halogenated $C_{1-6}$ alkyl), —N(unsubstituted or halogenated $C_{1-6}$ alkyl) S(O)N (unsubstituted or halogenated $C_{1-6}$ alkyl)$_2$, —N(unsubstituted or halogenated $C_{1-6}$ alkyl) S(O) (unsubstituted or halogenated $C_{1-6}$ alkyl), unsubstituted or halogenated $C_{5-10}$ aryl, unsubstituted or halogenated 5 to 10-membered heteroaryl, unsubstituted or halogenated $C_{4-5}$ cyclic hydrocarbyl, or unsubstituted or halogenated 4 to 8-membered heterocyclyl, wherein the heterocyclyl and heteroaryl comprise 1-4 heteroatoms selected from the following atoms: N, O or S.

As a preferred embodiment, one of $X_1$ and $X_2$ is $CH_2$, and the other is a bond.

As a preferred embodiment, $X_3$ is S.

As a preferred embodiment, $X_4$ is selected from N or CH.

As a preferred embodiment, $R_1$, $R_2$, $R_3$, $R_4$ and $R_7$ are independently selected from H, —OH, —F, —Cl, —Br, —NH$_2$, —NHC$_{1-3}$ alkyl, methyl, ethyl, propyl, isopropyl, butyl, methoxy, ethoxy, propoxy or isopropoxy; $C_{1-3}$ alkyl substituted by halogen, —NH$_2$, —OH, $C_{1-3}$ alkyl or $C_{1-3}$ alkoxyl; or $C_{1-3}$ alkoxyl substituted by halogen, —NH$_2$, —OH, $C_{1-3}$ alkyl or $C_{1-3}$ alkoxyl. As a preferred embodiment, $R_5$ and $R_6$ are independently selected from H, —OH, —F, —Cl, —Br, —CN, —NH$_2$, —NHC$_{1-3}$ alkyl, methyl, ethyl, propyl, isopropyl, butyl, methoxy, ethoxy, propoxy or isopropoxy; $C_{1-3}$ alkyl substituted by halogen, —NH$_2$, —OH, $C_{1-3}$ alkyl or $C_{1-3}$ alkoxyl; or $C_{1-3}$ alkoxyl substituted by halogen, —NH$_2$, —OH, $C_{1-3}$ alkyl or $C_{1-3}$ alkoxyl.

As a preferred embodiment, the substituent is selected from —F, —Cl, —Br, —OH, —NO$_2$, —NH$_2$, —NH(C$_{1-6}$ alkyl), —N(C$_{1-6}$ alkyl)$_2$, —CN, $C_{1-6}$ alkyl, CM alkoxyl, CM alkoxyl-$C_{1-6}$ alkyl, $C_{3-8}$ cycloalkyl-$C_{1-8}$ alkyl, $C_{1-6}$ alkyl carbonyl, $C_{1-6}$ alkoxyl carbonyl, $C_{1-6}$ alkyl thiol, —S(O)$_2$N (C$_{1-6}$ alkyl)$_2$, —S(O)$_2$ $C_{1-6}$ alkyl, —N(C$_{1-6}$ alkyl) S(O)$_2$N (C$_{1-6}$ alkyl)$_2$, —S(O)N(C$_{1-6}$ alkyl)$_2$, —S(O)(C$_{1-6}$ alkyl), —N(C$_{1-6}$ alkyl)S(O)N(C$_{1-6}$ alkyl)$_2$, —N(C$_{1-6}$ alkyl)S(O) (C$_{1-6}$ alkyl), substituted or unsubstituted $C_{5-10}$ aryl, substituted or unsubstituted 5 to 10-membered heteroaryl, substituted or unsubstituted $C_{4-8}$ cyclic hydrocarbyl, or substituted or unsubstituted 4 to 8-membered heterocyclyl, wherein the heterocyclyl and heteroaryl comprise 1-4 heteroatoms selected from the following atoms: N, O or S.

As a preferred embodiment, the substituent is selected from —F, —Cl, —Br, —OH, —NO$_2$, —NH$_2$, —NH(C$_{1-3}$ alkyl), —N(C$_{1-3}$ alkyl)$_2$, —CN, $C_{1-3}$ alkyl, $C_{1-3}$ alkoxyl, $C_{1-3}$ alkyl carbonyl, cyclopropyl, cyclobutyl, cyclopentyl, cyclopentenyl, cyclohexyl, cyclohexenyl, cyclohexadienyl, cycloheptyl, cyclooctyl, pyrrolidinyl, morpholinyl, piperazinyl, homopiperazinyl, piperidinyl, thiomorpholinyl, phenyl, naphthyl, anthracyl, phenanthryl, fluorenyl, thiophenyl, imidazolyl, pyrazolyl, thiazolyl, oxazolyl, oxadiazolyl, isoxazolyl, pyridyl, pyrimidinyl, pyrazinyl, pyridazinyl, benzimidazolyl, benzopyrazolyl, indolyl, furanyl, pyrrolyl, triazolyl, tetrazolyl, triazinyl, indolizinyl, isoindolyl, indazolyl, isoindazolyl, purinyl, quinolinyl or isoquinolinyl.

As a preferred embodiment, the substituent is selected from —F, —Cl, —Br, —OH, —NO$_2$, —NH$_2$, —NH(C$_{1-3}$ alkyl), —N(C$_{1-3}$ alkyl)$_2$, —CN, methyl, ethyl, propyl, isopropyl, butyl, methoxy, ethoxy, propoxy, isopropoxy or phenyl.

As a preferred embodiment, the ring C is selected from any of the following groups:

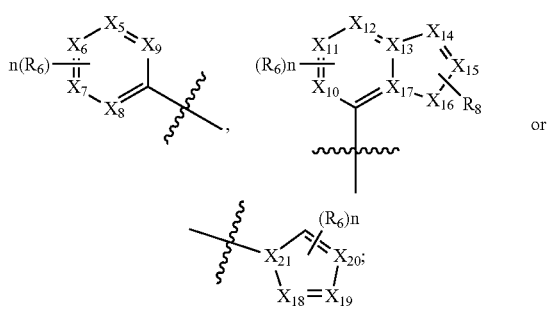

wherein:

$X_5$, $X_6$, $X_7$, $X_8$ and $X_9$ are independently selected from N or $CR_d$; and at most 3 of $X_5$, $X_6$, $X_7$, $X_8$ and $X_9$ are N simultaneously;

$X_{10}$, $X_{11}$, $X_{12}$, $X_{13}$, $X_{14}$, $X_{15}$, $X_{16}$ and $X_{17}$ are independently selected from N or $CR_d$; and at most 5 of $X_{10}$, $X_{11}$, $X_{12}$, $X_{13}$, $X_{14}$, $X_{15}$, $X_{16}$ and $X_{17}$ are N simultaneously;

$X_{18}$, $X_{19}$, $X_{20}$ and $X_{21}$ are independently selected from N or $CR_d$, and at most 3 of $X_{18}$, $X_{19}$, $X_{20}$ and $X_{21}$ are N simultaneously;

$R_6$ and $R_8$ are independently selected from H, —NH$_2$, —CN, —OH, —NO$_2$, halogen, unsubstituted or halogenated $C_{1-6}$ alkyl, or unsubstituted or halogenated $C_{1-6}$ alkoxyl; and $R_d$ is selected from H, halogen, unsubstituted or halogenated $C_{1-6}$ alkyl, or unsubstituted or halogenated $C_{1-6}$ alkoxyl.

As a preferred embodiment, the ring C is selected from any of the following groups:

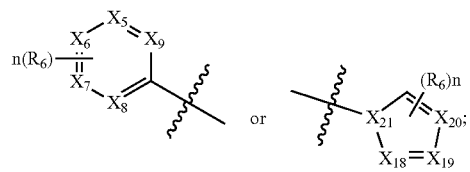

wherein:

0, 1 or 2 of $X_5$, $X_6$, $X_7$, $X_8$ and $X_9$ are N, the others are $CR_d$;

0, 1 or 2 of $X_{18}$, $X_{19}$, $X_{20}$ and $X_{21}$ are N, the others are $CR_d$;

$R_6$ is selected from H, —NH$_2$, —CN, —OH, —NO$_2$, —F, —Cl, —Br, methyl, ethyl, propyl, isopropyl, butyl, methoxy, ethoxy, propoxy, isopropoxy, fluorinated or brominated $C_{1-3}$ alkyl, fluorinated or brominated $C_{1-3}$ alkoxyl; and $R_d$ is selected from H, —F, —Cl, —Br, methyl, ethyl, propyl, isopropyl, butyl, methoxy, ethoxy, propoxy, isopropoxy, fluorinated or brominated $C_{1-3}$ alkyl, or fluorinated or brominated $C_{1-3}$ alkoxyl.

As a preferred embodiment, the ring C is selected from any of the following groups:

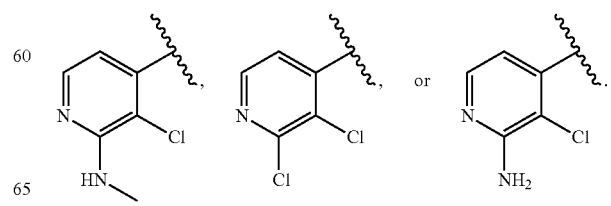

As a preferred embodiment, the ring A is selected from substituted or unsubstiuted C$_{4-6}$ cyclic hydrocarbyl, substituted or unsubstiuted 4 to 6-membered heterocyclyl, substituted or unsubstiuted C$_{5-6}$ aryl, or substituted or unsubstiuted 5 to 6-membered heteroaryl, wherein the heterocyclyl or heteroaryl comprises 1-3 N atoms.

As a preferred embodiment the ring A is selected from any of the following groups:

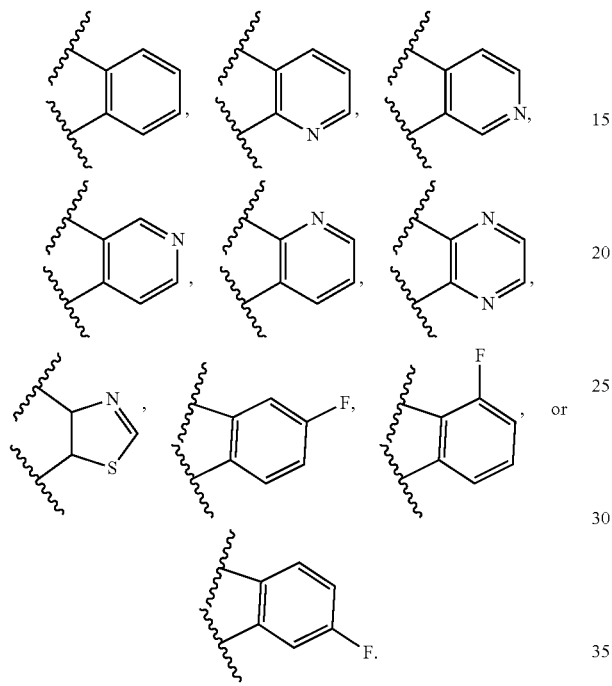

As a preferred embodiment, the ring A is selected from any of the following groups:

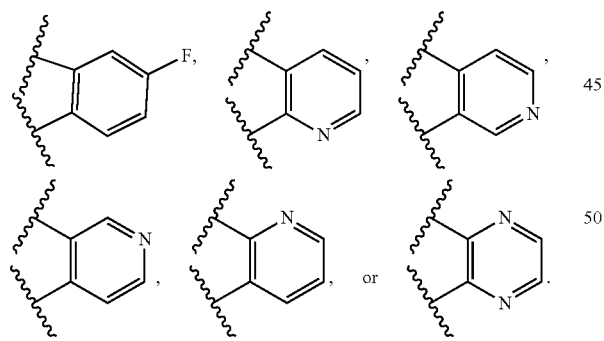

As a further preferred embodiment, the compound has a structure selected from:

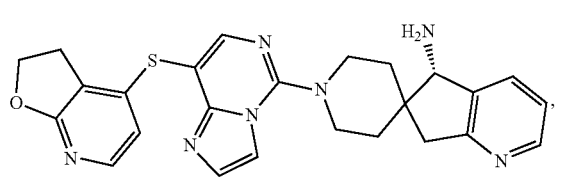

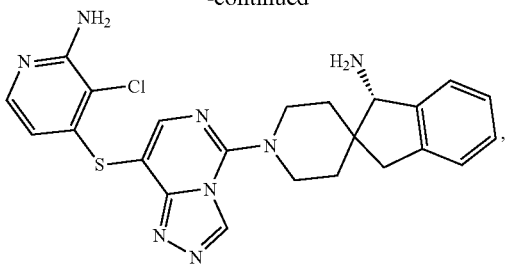

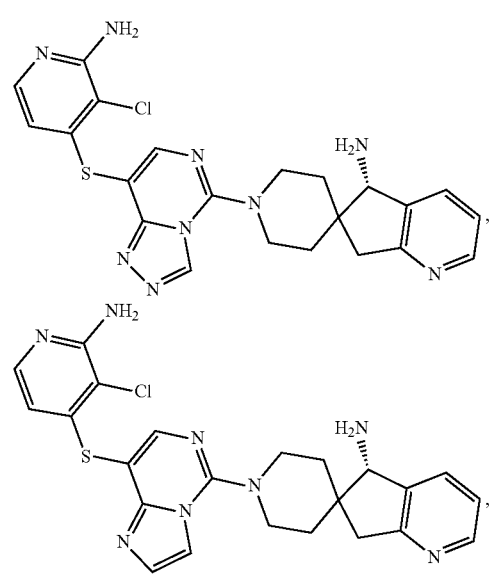

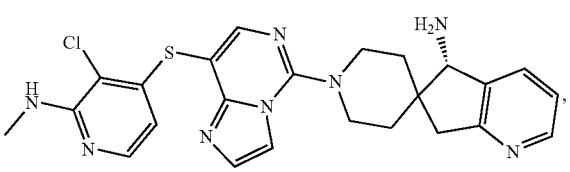

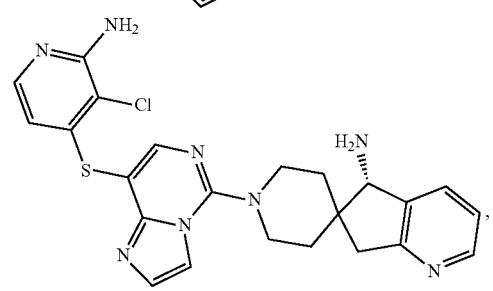

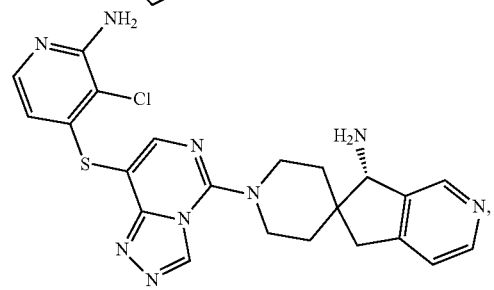

-continued
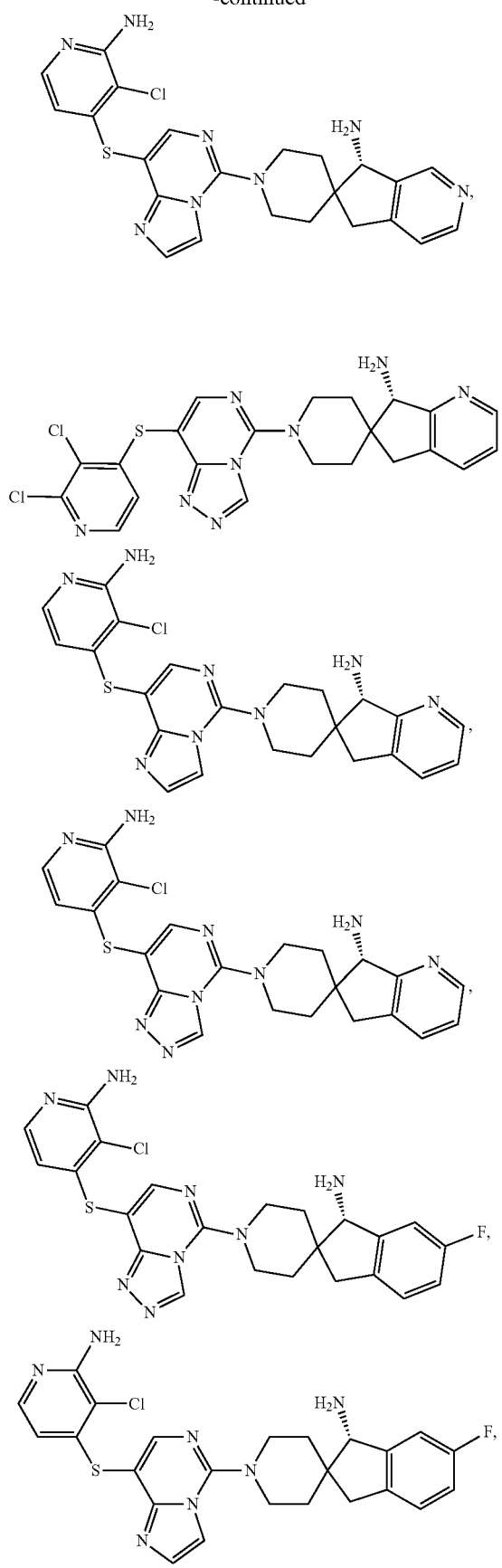
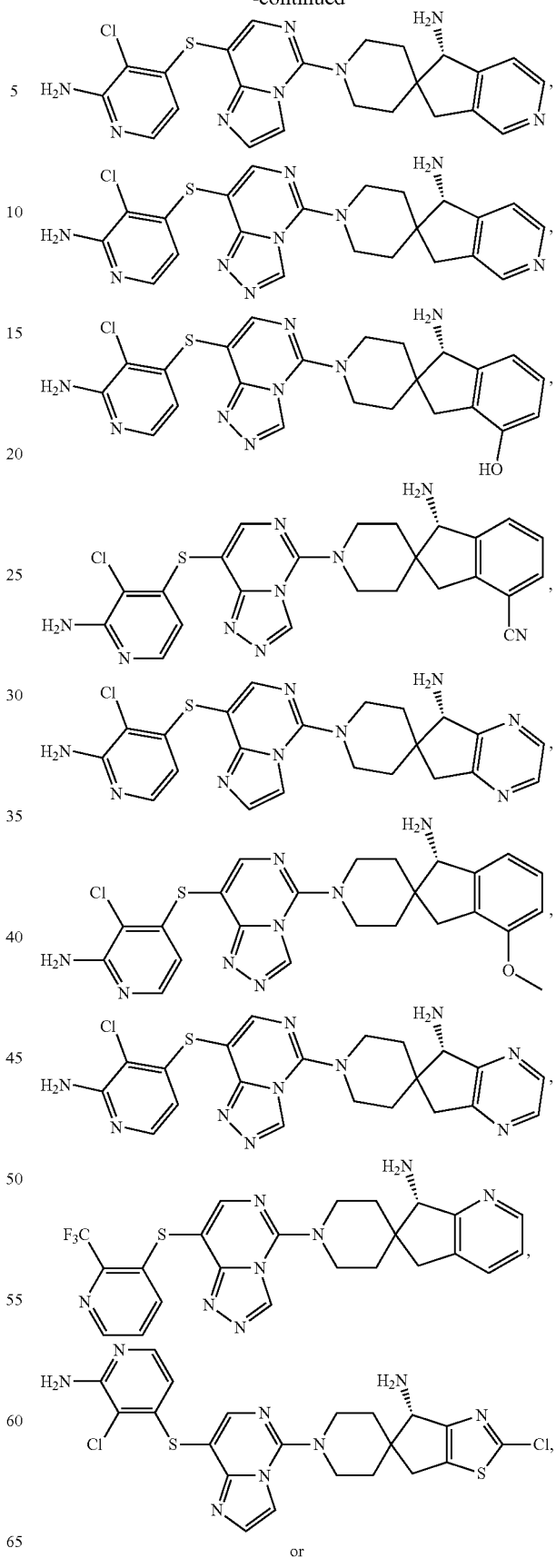
or

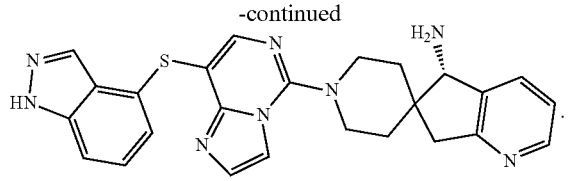

As a preferred embodiment, the isotopic substitution of the isotope-substituted derivative of the compound herein relates to atom comprises but not limited to hydrogen, carbon, nitrogen, oxygen, fluorine, phosphorus, chlorine or iodine; and preferably is $^2H$, $^3H$, $^{11}C_{1-6}$, $^{13}C$, $^{14}C$, $^{15}N$, $^{17}O$, $^{18}O$, $^{18}F$, $^{31}P$, $^{32}P$, $^{35}S$, $^{36}Cl$ or $^{125}I$.

The second aspect of the disclosure provides a method for preparation of a compound of Formula i of the disclosure, wherein the method comprises:

(i) performing nucleophilic substitution reaction between Formula Ib and Formula Ic to obtain Formula Id;

(ii) performing substitution reaction between Formula Id and Formula Ie to obtain Formula If; and (iii) deprotecting Formula If by acid to obtain the compound of Formula I:

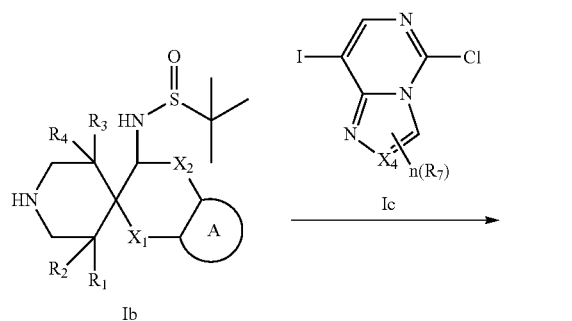

Ib

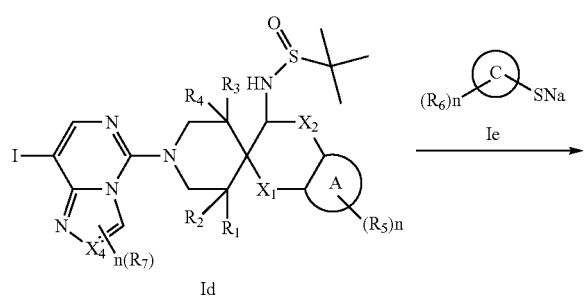

Id

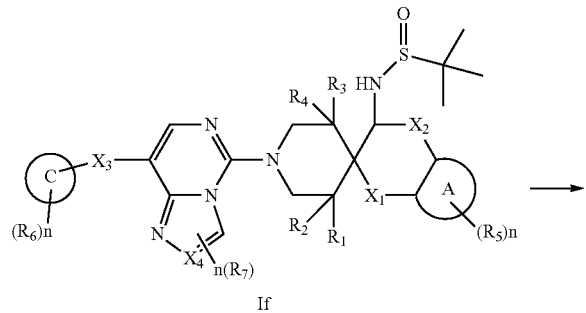

If

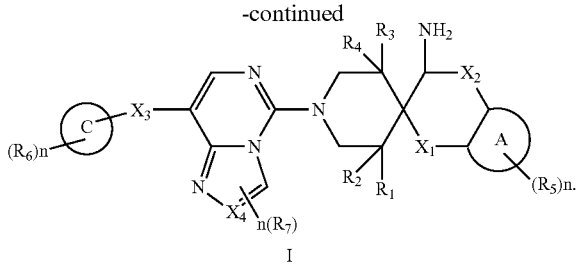

I

The third aspect of the disclosure provides use of a compound of Formula I of the disclosure in a method for:

(a) preparing a medicament for the prevention or treatment of diseases or conditions related to abnormal SHP2 activity;

(b) preparing a medicament for the prevention or treatment of SHP2-mediated diseases or conditions;

(c) preparing an inhibitor medicament for the inhibition of SHP2 activity;

(d) inhibiting SHP2 activity non-therapeutically in vitro;

(e) inhibiting tumor cell proliferation non-therapeutically in vitro; or (f) treating diseases or conditions related to abnormal SHP2.

As a preferred embodiment, the disease is cancer, preferably is Noonan Syndrome, Leopard Syndrome, juvenile myelomonocytic leukemia, neuroblastoma, melanoma, acute myeloid leukemia, breast cancer, esophageal cancer, lung cancer, colon cancer, head cancer, neuroblastoma, squamous cell carcinoma of head and neck, gastric cancer, anaplastic large cell lymphoma or glioblastoma.

The fourth aspect of the disclosure provides a pharmaceutical composition comprising:

(i) an effective amount of a compound of Formula I, or a pharmaceutically acceptable salt, enantiomer, diastereoisomer, tautomer, solvate, isotope-substituted derivative, polymorph, prodrug or metabolite thereof; and (ii) a pharmaceutically acceptable carrier.

The fifth aspect of the disclosure provides a method for inhibiting SHP2 activity, wherein the method comprises the following step: administering to a subject in need thereof an effective amount of a compound of Formula I of the disclosure or a pharmaceutically acceptable salt thereof, or administering to a subject in need thereof an effective amount of a pharmaceutical composition of the disclosure.

It should be understood that the above technical features of the disclosure and the technical featetres specifically described in the following (such as embodiments) can be combined within the scope of the disclosure to form new or preferred technical solutions. For purposes of simplicity, they will not be described one by one herein.

DETAILED DESCRIPTION OF THE DISCLOSURE

After long and intensive research, the inventors prepared novel allosteric inhibitor compounds of Formula I, which can achieve the purpose of inhibiting SHP2 activity by binding to the non-catalytic region of SHP2 and "locking" the self-inhibiting state with weak SHP2 activity. The compounds of the disclosure exhibit very good biological activity and druggability, and have very good drug development prospects; they have an inhibitory effect on SHP2 at very low concentrations (as low as ≤100 nM/L), and the inhibitory activity is quite excellent, so they can be used to treat SHP2-related diseases or conditions, such as tumors.

Based on the above discovery, the inventors completed the invention.

Term

Unless defined otherwise, all technical and scientific terms used herein have the same meaning as commonly understood by those of ordinary skill in the art to which the subject matter of the claims belong. Unless specified otherwise, all patents, patent applications, and disclosed materials cited herein are incorporated into the present disclosure by reference in their entirety.

It should be understood that the above brief description and the following detailed description are exemplary and are for interpretation only, without any limitation to the subject matter of the disclosure. In this disclosure, unless specified otherwise, the plural is also included when the singular is used. It should be noted that unless otherwise clearly stated in the text, the singular form used in the specification and claims includes the plural form of the subject referred to. It should also be noted that unless specified otherwise, the term "or" is used for representing "and/or". In addition, the term "include" and its grammatical variants, such as "comprise", "contain" and "have", are not restrictive and may be open, semi closed and closed. In other words, the term "include" and its grammatical variants also include the meaning of "substantially consist of", or "consists of".

The definitions of standard chemical terms can be found in references (including Carey and Sundberg "ADVANCED ORGANIC CHEMISTRY 4TH ED." Vols. A (2000) and B (2001), *Plenum Press*, New York). Unless specified otherwise, conventional methods within the scope of the art, e.g., mass spectroscopy, NMR, IR and UV/VIS spectroscopy and pharmacology methods, are used. Unless specifically defined, the terms used in the present disclosure related to analytical chemistry, organic synthetic chemistry, medicine and pharmaceutical chemistry herein are known in the art. Standard techniques can be used in chemical synthesis, chemical analysis, drug preparation, preparations and delivery, and in the treatment of patients. For example, reactions and purifications may be carried out according to the manufacturer's instructions for use of kit, or in a manner well known in the art or according to the description of the disclosure. Generally, the above techniques and methods can be implemented in accordance with the conventional methods well known in the art according to the descriptions in the multiple general and more specific literatures cited and discussed in the present description. In the present description, groups and substituents may be selected by a person skilled in the art to provide stable structural parts and compounds.

When a substituent is described by a conventional formula written from left to right, the substituent also includes the chemically equivalent substituent obtained when the structural formula is written from right to left. For example, —CH$_2$O— is equal to —OCH$_2$—.

The section headings as used herein are for the purpose of organizing the article only and should not be interpreted as limitation to the subject. All the literatures or literature parts cited herein, including but not limited to patents, patent applications, articles, books, operation manuals and papers, are incorporated into the present disclosure by reference in their entirety.

Some chemical groups defined herein are preceded by simplified symbols to represent the total number of carbon atoms in the group. For example, $C_1$-$C_6$ alkyl refers to an alkyl as defined below having a total of 1 to 6 carbon atoms. The total number of carbon atoms in the simplified symbols does not comprise carbon atoms that may exist in the substituents of the group.

In addition to the foregoing, when used in the specification and claims of the disclosure, unless specifically indicated otherwise, the following terms have the meanings as follows.

In the disclosure, the term "halogen" refers to fluorine, chlorine, bromine or iodine.

"Hydroxyl" refers to —OH group.

"Hydroxyl alkyl" refers to an alkyl as defined below substituted by hydroxyl (—OH).

"Carbonyl" refers to —C(=O)— group.

"Nitryl" refers to —NO$_2$.

"Cyano" refers to —CN.

"Amino" refers to —NH$_2$.

"Substituted amino" refers to an amino substituted by one or two of the alkyl, alkyl carbonyl, aryl alkyl, heteroaryl alkyl as defined below, for example, substituted amino may be monoalkyl amino, dialkyl amino, alkyl acylamino, aryl alkyl amino, heteroaryl alkyl.

"Carboxyl" refers to —COOH.

In the disclosure, as a group or part of other groups (for example, used in groups such as halogenated (such as fluorinated, chlorinated, brominated or iodinated) alkyl), the term "alkyl" refers to a fully saturated straight or branched hydrocarbon chain group, consisting only of carbon atoms and hydrogen atoms, for example, comprising 1 to 12 (preferably 1 to 8, more preferably 1 to 6) carbon atoms, and connected to the rest of the molecule by a single bond. For example, "alkyl" includes, but is not limited to methyl, ethyl, n-propyl, isopropyl, n-butyl, isobutyl, sec-butyl, tert-butyl, n-amyl, 2-methylbutyl, 2,2-dimethylpropyl, n-hexyl, heptyl, 2-methylhexyl, 3-methylhexyl, octyl, nonyl and decyl, etc. In the case of the present disclosure, the term "alkyl" refers to an alkyl group containing 1 to 8 carbon atoms.

In the disclosure, as a group or part of other groups, the term "alkenyl" refers to a straight or branched hydrocarbon chain group, consisting only of carbon atoms and hydrogen atoms, for example, comprising 2 to 20 (preferably 2 to 10, more preferably 2 to 6) carbon atoms, comprising at least one double bond, and connected to the rest of the molecule by a single bond, Examples, include but are not limited to, vinyl, propenyl, allyl, but-1-enyl, but-2-enyl, pent-1-enyl, pent-1,4-dienyl, etc.

In the disclosure, as a group or part of other groups, the term "cyclic hydrocarbyl" refers to a stable non-aromatic monocyclic or polycyclic hydrocarbyl (such as alkyl, alkenyl or alkynyl) consisting only of carbon atoms and hydrogen atoms, which may comprise fused ring system, bridged ring system or spiro ring system, comprise 3 to 15 carbon atoms, preferably comprise 3 to 10 carbon atoms, more preferably comprise 3 to 8 carbon atoms, for example, comprise 3, 4, 5, 6, 7 or 8 carbon atoms, and which is saturated or unsaturated and may be connected to the rest of the molecule via any suitable carbon atom by a single bond. Unless otherwise specifically indicated in the description, the carbon atoms in the cyclic hydrocarbyl may be optionally oxidized. Embodiments of cyclic hydrocarbyl include but are not limited to cyclopropyl, cyclobutyl, cyclopentyl, cyclopentenyl, cyclohexyl, cyclohexenyl, cyclohexadienyl, cycloheptyl, cyclooctyl, 1H-indenyl, 2,3-dihydroindenyl, 1,2,3,4-tetrahydro-naphthyl, 5,6,7,8-tetrahydro-naphthyl, 8,9-dihydro-7H-benzocycloheptene-6-yl, 6,7,8,9-tetrahydro-5H-benzocycloheptenyl, 5,6,7,8,9,10-hexahydro-benzocyclooctenyl, fluorenyl, bicyclo[2.2.1]heptyl, 7,7-dimethyl-bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octenyl, bicyclo[3.2.1]octenyl, adamantyl, octahydro-4,7-methylene-1H-indenyl and octahydro-2,5-methylene-dicyclopentadienyl, etc.

In the disclosure, as a group or part of other groups, the term "heterocyclyl" refers to a stable 3 to 20-membered non-aromatic cyclic group consisting of 2 to 14 carbon atoms (for example, 2, 3, 4, 5, 6, 7, 8, 9, 10, 11, 12, 13 or 14 carbon atoms) and 1 to 6 heteroatoms selected from nitrogen, phosphorus, oxygen or sulfur. Unless otherwise specifically indicated in the description, a heterocyclyl may be a monocyclic ring system, a dicyclic ring system, a tricyclic ring system or a ring system with more rings, and may comprise fused ring system, bridged ring system or spiro ring system; the nitrogen, phosphorus or sulfur atoms in the heterocyclyl may be optionally oxidized; the nitrogen atoms in the heterocyclyl may be optionally quaternized; and the heterocyclyl may be partially or fully saturated. The heterocyclyl may be connected to the rest of the molecule via a carbon atom or a heteroatom by a single bond. In a heterocyclyl containing fused ring, one or more rings may be aryl or heteroaryl as defined below, provided that the connection point between the group and the rest of the molecule is a non-aromatic ring atom. For the purpose of the present disclosure, heterocyclyl is preferably a stable 4 to 11-membered non-aromatic monocyclic, dicyclic, bridged or spiro ring group comprising 1 to 3 heteroatoms selected from nitrogen, oxygen or sulfur, more preferably a stable 4 to 8-membered non-aromatic monocyclic, dicyclic, bridged or spiro ring group comprising 1 to 3 heteroatoms selected from nitrogen, oxygen or sulfur. Exemplary heterocyclyls include but are not limited to: pyrrolidinyl, morpholinyl, piperazinyl, homopiperazinyl, piperidinyl, thiomorpholinyl, 2,7-diaza-spiro[3.5]nonane-7-yl, 2-oxa-6-aza-spiro[3.3]heptane-6-yl, 2,5-diazabicyclo[2.2.1]heptane-2-yl, azacyclobutanyl, pyranyl, tetrahydropyranyl, thiopyranyl, tetrahydrofuranyl, oxazinyl, dioxolanyl, tetrahydroisoquinolinyl, decahydroisoquinolinyl, imidazolinyl, imidazolidinyl, quinolizinyl, thiazolidinyl, isothiazolidinyl, isoxazolidinyl, dihydroindolyl, octahydroindolyl, octahydroisoindolyl, pyrrolidinyl, pyrazolidinyl, phthalimido, etc.

In the disclosure, as a group or part of other groups, the term "aryl" refers to a conjugated hydrocarbon ring system group comprising 6 to 18 carbon atoms (preferably comprising 6 to 10 carbon atoms, for example, 6, 7, 8, 9 or 10 carbon atoms). For the purpose of the present disclosure, aryl may be a monocyclic ring system, a dicyclic ring system, a tricyclic ring system or a ring system with more rings, and may be fused with the cyclic hydrocarbyl or heterocyclyl as defined above, provided that the aryl and the rest of the molecule are connected via an atom on the aromatic ring by a single bond. Exemplary aryls include but are not limited to phenyl, naphthyl, anthracyl, phenanthrenyl, fluorenyl, 2,3-dihydro-1H-isoindolyl, 2-benzoxazolinone, 2H-1,4-benzoxazin-3(4H)-one-7-yl, etc.

In the disclosure, the term "aryl alkyl" refers to an alkyl as defined above which is substituted by an aryl as defined above.

In the disclosure, as a group or part of other groups, the term "heteroaryl" refers to a 5 to 16-membered conjugated ring system group comprising 1 to 15 carbon atoms (preferably comprising 1 to 10 carbon atoms, for example, 1, 2, 3, 4, 5, 6, 7, 8, 9 or 10 carbon atoms) and 1 to 6 heteroatoms selected from nitrogen, oxygen or sulfur. Unless otherwise specifically indicated in the description, a heteroaryl may be a monocyclic ring system, a dicyclic ring system, a tricyclic ring system or a ring system with more rings, and may be fused with the cycloalkyl or heterocyclyl, provided that the heteroaryl and the rest of the molecule are connected via an atom on the aromatic ring by a single bond. The nitrogen, carbon or sulfur atoms in the heteroaryl may be optionally oxidized; the nitrogen atoms in the heteroaryl may be optionally quaternized. For the purpose of the disclosure, heteroaryl is preferably a stable 5 to 12-membered aromatic group comprising 1 to 5 heteroatoms selected from nitrogen, oxygen or sulfur, and is more preferably a stable 5 to 10-membered aromatic group comprising 1 to 4 heteroatoms selected from nitrogen, oxygen or sulfur, or a 5 to 6-membered aromatic group comprising 1 to 3 heteroatoms selected from nitrogen, oxygen or sulfur. Exemplary heteroaryls include but are not limited to thiophenyl, imidazolyl, pyrazolyl, thiazolyl, oxazolyl, oxadiazolyl, isoxazolyl, pyridyl, pyrimidinyl, pyrazinyl, pyridazinyl, benzimidazolyl, benzopyrazolyl, indolyl, furanyl, pyrrolyl, triazolyl, tetrazolyl, triazinyl, indolizinyl, isoindolyl, indazolyl, isoindazolyl, purinyl, quinolinyl, isoquinolinyl, diazanaphthalenyl, naphthyridinyl, quinoxalinyl, pteridinyl, carbazolyl, carbolinyl, phenanthridinyl, phenanthrolinyl, acridinyl, phenazinyl, isothiazolyl, benzothiazolyl, benzothiophenyl, oxatriazolyl, cinnolinyl, quinazolyl, phenylthio, indolizinyl, phenanthrolinyl, isoxazolyl, phenoxazinyl, phenothiazinyl, 4,5,6,7-tetrahydrobenzo[b]thiophenyl, naphthopyridinyl, [1,2,4]triazolo[4,3-b]pyridazine, [1,2,4]triazolo[4,3-a]pyrazine, [1,2,4]triazolo[4,3-c]pyrimidine, [1,2,4]triazolo[4,3-a]pyridine, imidazo[1,2-a]pyridine, imidazo[1,2-b]pyridazine, imidazo[1,2-a]pyrazine, etc.

In the disclosure, the term "heteroaryl alkyl" refers to an alkyl as defined above which is substituted by heteroaryl as defined above.

In the disclosure, "optional" or "optionally" means that the subsequently described event or condition may or may not occur, and such description includes both occurrence and non-occurrence of the event or condition. For example, "optionally substituted aryl" means an aryl being substituted or not being substituted, and such description includes both substituted aryl and unsubstituted aryl. The "optional" substituent employed in the claims and description of the disclosure is selected from alkyl, alkenyl, alkynyl, halogen, haloalkyl, haloalkenyl, haloalkynyl, cyano, nitro, optionally substituted aryl, optionally substituted heteroaryl, optionally substituted cyclic hydrocarbyl, or optional substituted heterocyclyl.

"SHP2" refers to "Src Homolgy-2 phosphatase", also called SH-PTP2, SH-PT3, Syp, PTP1D, PTP2C$_{1-6}$, SAP-2 or PTPN11.

The terms "part", "structural part", "chemical part", "group", "chemical group" as employed herein refer to specific part or functional group in the molecular. Chemical part is generally considered to be chemical entity embedded or attached to molecule.

"Stereisomer" refers to a compound composed of the same atoms, bonded by the same bonds, but having different three-dimensional structures. The present disclosure will cover various stereoisomers and mixtures thereof.

When a compound of the present disclosure contains an olefinic double bond, unless specified otherwise, the compound of the present disclosure is intended to include E- and Z-geometric isomers.

"Tautomer" refers to an isomer formed by the transfer of proton from one atom of a molecule to another atom of the same molecule. All tautomeric forms of a compound of the disclosure will also be included within the scope of the disclosure.

A compound of the disclosure or pharmaceutically acceptable salt thereof may comprise one or more chiral carbon atoms, and thus may produce enantiomers, diastereomers, and other stereoisomeric forms. Each chiral carbon atom can be defined as (R)- or (s)-based on stereochemistry. The disclosure is intended to include all possible isomers, as well as racemes and optically pure forms thereof. A compound of the disclosure can be prepared by using raceme, diastereomer or enantiomer as raw material or intermediate. The optically active isomers can be prepared by using chiral synthons or chiral reagents, or separated by conventional techniques, such as crystallization and chiral chromatography.

Conventional techniques for preparing/separating individual isomers include chiral synthesis from suitable optically pure precursors, or separation of racemes (or racemates of salts or derivatives) using, for example, chiral high performance liquid chromatography, for example, see Gerald Gubitz and Martin G. Schmid (Eds.), Chiral Separations, Methods and Protocols, Methods in Molecular Biology, Vol. 243, 2004; A. M. Stalcup, Chiral Separations, Annu. Rev. Anal. Chem. 3:341-63, 2010; Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; Heller, Acc. Chem. Res. 1990, 23, 128.

The disclosure also includes all suitable isotopic variations of the compounds of the present disclosure or pharmaceutically acceptable salts thereof. Isotopic variations of the compounds of the present disclosure or pharmaceutically acceptable salts thereof are defined as those in which at least one atom is replaced by an atom having the same atomic number but an atomic mass different from the atomic mass often found in nature. Isotopes that can be incorporated into the compounds of the present disclosure and their pharmaceutically acceptable salts thereof include but are not limited to H, C, N and O, for example, $^2H$, $^3H$, $^{11}C$, $^{13}C$, $^{14}C$, $^{15}N$, $^{17}O$, $^{18}O$, $^{35}S$, $^{18}F$, $^{36}Cl$ and $^{125}I$. Suitable isotopic variations of the compounds or pharmaceutically acceptable salts thereof of the present disclosure may be prepared by conventional techniques using appropriate isotopic variants of suitable reagents.

In the disclosure, the term "pharmaceutically acceptable salt" includes pharmaceutically acceptable acid addition salts and pharmaceutically acceptable base addition salts.

"Pharmaceutically acceptable acid addition salt" refers to a salt formed with an inorganic acid or an organic acid that can retain the biological effectiveness of the free base without other side effects. Inorganic acid salts include but are not limited to hydrochloride, hydrobromide, sulfate, nitrate, phosphate, etc.; organic acid salts include but are not limited to formate, acetate, 2,2-dichloroacetate, trifluoroacetate, propionate, hexanoate, caprylate, caprate, undecylenate, glycolate, gluconate, lactate, sebacate, adipate, glutarate, malonate, oxalate, maleate, succinate, fumarate, tartrate, citrate, palmitate, stearate, oleate, cinnamate, laurate, malate, glutamate, pyroglutamate, aspartate, benzoate, methanesulfonate, benzenesulfonate, p-toluenesulfonate, alginate, ascorbate, salicylate, 4-aminosalicylate, naphthalene disulfonate, etc. These salts can be prepared by methods known in the art.

"Pharmaceutically acceptable base addition salts" refers to a salt formed with an inorganic base or an organic base that can retain the biological effectiveness of the free acid without other side effects. Salts derived from inorganic bases include but are not limited to sodium salt, potassium salt, lithium salt, ammonium salt, calcium salt, magnesium salt, iron salt, zinc salt, copper salt, manganese salt, aluminum salt, etc. Preferred inorganic salts are ammonium salt, sodium salt, potassium salt, calcium salt and magnesium salt. Salts derived from organic bases include but are not limited to the following salts: primary amines, secondary amines, and tertiary amines, substituted amines, including natural substituted amines, cyclic amines and basic ion exchange resins, such as ammonia, isopropylamine, trimethylamine, diethylamine, triethylamine, tripropylamine, ethanolamine, diethanolamine, triethanolamine, dimethylethanolamine, 2-dimethylaminoethanol, 2-diethylaminoethanol, dicyclohexylamine, lysine, arginine, histidine, caffeine, procaine, choline, betaine, ethylenediamine, glucosamine, methylglucosamine, theobromine, purine, piperazine, piperidine, N-ethylpiperidine, polyamine resin, etc. Preferred organic bases include isopropylamine, diethylamine, ethanolamine, trimethylamine, dicyclohexylamine, choline and caffeine. These salts can be prepared by methods known in the art.

In the disclosure, "pharmaceutical composition" refers to a formulation of a compound of the present disclosure and a medium generally accepted in the art for delivering a biologically active compound to a mammal (e.g., human). The medium includes a pharmaceutically acceptable carrier. The purpose of the pharmaceutical composition is to promote the administration of living organisms, which facilitates the absorption of active ingredients and thus exerts biological activity.

The term "pharmaceutically acceptable" as used herein refers to a substance (such as a carrier or diluent) that does not affect the biological activity or properties of the compound of the present disclosure, and is relatively non-toxic, that is, the substance can be administered to an individual without causing adverse biological reactions or interacting with any components contained in the composition in an undesirable manner.

In the disclosure, "pharmaceutically acceptable excipient" includes but is not limited to any adjuvant, carrier, excipient, glidant, sweetener, diluent, preservative, dye/colorant, corrigent, surfactant, wetting agent, dispersant, suspending agent, stabilizer, isotonic agent, solvent or emulsifier that is approved by relevant government regulatory agency to be acceptable for human or domestic animal use.

"Tumour" in the disclosure includes but is not limited to Noonan Syndrome, Leopard Syndrome, juvenile myelomonocytic leukemia, neuroblastoma, sarcoma, melanoma, articular chondroma, cholangioma, leukemia, breast cancer, gastrointestinal stromal tumor, histiocytic lymphoma, non-small cell lung cancer, small cell lung cancer, esophageal cancer, pancreatic cancer, lung squamous cancer, lung adenocarcinoma, breast cancer, prostate cancer, liver cancer, skin cancer, epithelial cell cancer, cervical cancer, ovarian cancer, intestinal cancer, nasopharynx cancer, brain cancer, bone cancer, kidney cancer, oral cancer/head cancer, neuroblastoma, squamous cell carcinoma of head and neck, anaplastic large cell lymphoma or glioblastoma and other diseases.

The terms "preventive", "prevent" and "prevention" as employed herein include reducing the possibility of the occurrence or deterioration of a disease or condition in a patient.

The term "treatment" and other similar synonyms as employed herein include the following meanings:

(i) prevention of the occurrence of a disease or condition in mammals, especially when such mammals are susceptible to the disease or condition but have not been diagnosed with the disease or condition;

(ii) suppression of a disease or condition, that is, inhibition of the development of the disease or condition;

(iii) alleviation of a disease or condition, that is, abatement of the status of the disease or condition; or (iv) relief of the symptoms caused by the disease or condition.

The term "effective amount", "therapeutically effective amount" or "pharmaceutically effective amount" as used herein refers to the amount of at least one medicament or compound sufficient to relieve one or more symptoms of the disease or disease being treated to a certain extent after administration. The result may be the reduction and/or remission of signs, symptoms or causes, or any other desired changes in the biological system. For example, an "effective amount" for treatment is the amount of a composition comprising a compound as disclosed herein required to provide a clinically significant disease relief effect. Techniques such as dose escalation tests may be used to determine the effective amount suitable for any individual case.

The terms "taking", "application", "administration" and the like refer to a method capable of delivering a compound or composition to a desired site for biological action. These methods include but are not limited to oral route, transduodenal route, parenteral injection (including intravenous, subcutaneous, intraperitoneal, intramuscular, intraarterial injection or infusion), local administration, and transrectal administration. One skilled in the art is familiar with the administration techniques that can be used for the compounds and methods as described herein, such as those discussed in Goodman and Gilman, The Pharmacological Basis of Therapeutics, current ed.; Pergamon; and Remington's, Pharmaceutical Sciences (current edition), Mack Publishing Co., Easton, Pa. In a preferred embodiment, the compounds and compositions discussed herein are administered orally.

The terms "medicament combination", "medicament co-administration", "combined medication", "administration of other treatments", "administration of other therapeutic agents" and the like as employed herein refer to medical treatment obtained by mixing or combining more than one active ingredient, and include fixed and unfixed combinations of active ingredients. The term "fixed combination" refers to the simultaneous administration of at least one compound described herein and at least one synergistic medicament to a patient in the form of a single entity or a single dosage form. The term "unfixed combination" refers to simultaneous administration, co-administration, or sequential administration at variable intervals of at least one compound described herein and at least one synergistic formulation to a patient in the form of separate entities. These also apply to cocktail therapy, such as the administration of three or more active ingredients.

One skilled in the art should also understand that in the method described below, the functional group of an intermediate compound may need to be protected by an appropriate protecting group. Such functional groups include hydroxyl, amino, sulfydryl and carboxylic acid. Suitable hydroxyl-protecting groups include trialkylsilyl or diarylalkylsilyl (e.g. tert-butyldimethylsilyl, tert-butyldiphenylsilyl or trimethylsilyl), tetrahydropyranyl, benzyl, etc. Suitable protecting groups for amino, amidino and guanidino include tert-butoxycarbonyl, benzyloxycarbonyl, etc. Suitable sulfydryl-protecting groups include —C(O)—R" (wherein R" is alkyl, aryl or aralkyl), p-methoxybenzyl, trityl, etc. Suitable carboxy-protecting groups include alkyl, aryl or aralkyl esters.

Protecting groups may be introduced and removed according to standard techniques known to one skilled in the art and as described herein. The use of protecting groups is described in detail in Greene, T. W. and P. G. M. Wuts, Protective Groups in Organi Synthesis, (1999), 4th Ed., Wiley. Protecting groups may also be polymer resins.

Preparation of the Compound of Formula I

The compound of Formula I provided by the present disclosure may be prepared by the following method: performing nucleophilic substitution reaction between Formula Ib and Formula Ic to obtain Formula Id; performing substitution reaction between Formula Id and Formula Ie to obtain Formula If; and deprotecting Formula If using acid to obtain the compound of Formula I:

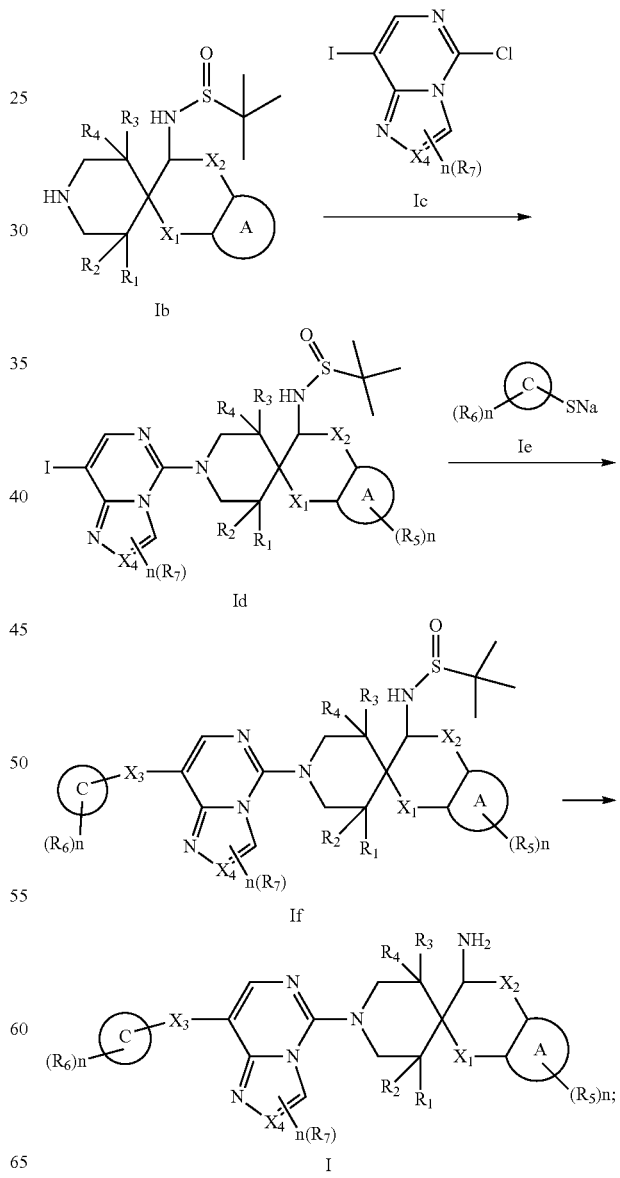

In the formula, the definition of each group is as described above.

Pharmacology and Use

Src Hommolgy-2 phosphatase (SHP2) is a protein tyrosine phosphatase encoded by the PTPN11 gene, which promotes various cell functions, including proliferation, differentiation, cell cycle maintenance, and migration. SHP2 is involved in signaling via Ras-mitogen-activated protein kinase, JAK-STAT or phosphoinositide 3-kinase-AKT pathway. SHP2 mediates the activation of receptor tyrosine kinases such as ErbBland ErbB2, and Erk1 and Erk2 MAP kinases of c-Met.

SHP2 has two N-terminal Src Homolgy-2 domains (N-SH2 and C-SH2), a catalytic domain (PTP) and a C-terminal tail. The two SH2 domains control the subcellular localization and functional regulation of SHP2. The molecule exists in an inactive conformation, inhibiting its own activity via a binding network involving residues from N-SH2 and PTP domains. In response to the stimulation of growth factor, SHP2 binds to specific tyrosine-phosphorylation sites, such as Gab1 and Gab2, on docking proteins via SHP2's SH2 domain. This causes conformational change, leading to SHP2 activation.

Mutations in PTPN11 have been identified in various human diseases such as Noonan Syndrome, Leopard Syndrome, juvenile myelomonocytic leukemia, neuroblastoma, melanoma, acute myeloid leukemia and cancers of breast, lung and colon. SHP2 is an important downstream signaling molecule for various receptor tyrosine kinases, including the receptors of platelet-derived growth factor (PDGF-R), fibroblast growth factor (FGF-R) and epidermal growth factor (EGF-R). SHP2 is also an important downstream signaling molecule that activates the mitogen-activated protein (MAP) kinase pathway, which can lead to cell transformation (a necessary condition for cancer development). The knockdown of SHP2 significantly inhibits cell growth of lung cancer cell lines having SHP2 mutations or EML4/ALK translocation, as well as EGFR-amplified breast and esophageal cancer. SHP2 is also a downstream gene of the activation of oncogenes in gastric cancer, anaplastic large cell lymphoma, and glioblastoma.

Noonan Syndrome (NS) and Leopard Syndrome (LS)-PTPN11 mutation causes LS (multiple pigmented nevus syndrome, abnormal ECG conduction, distance between eyes too far, pulmonary valve stenosis, abnormal genitalia, growth retardation, sensorineural hearing loss) and NS (including congenital abnormalities of heart defect, craniofacial deformity and short stature). These two disorders are parts of autosomal dominant syndrome family caused by germline mutations in the components of the RAS/RAF/MEK/ERK mitogen-activated protein kinase pathway (required for normal cell growth and differentiation). Abnormal regulation of this pathway has far-reaching effects, especially on heart development, leading to a variety of abnormalities, including valvuloseptal defects and/or hypertrophic cardiomyopathy (HCM). It has been determined that the disturbance of MAPK signaling pathway is important for these disorders, and some candidate genes that follow this pathway have been identified in humans, including mutations in KRAS, NRAS, SCS1, RAF1, BRAF, MEK1, MEK2, SH0C2 and CBL. The most frequently mutated gene in NS and LS is PTPN11. Germline mutations of PTPN11 (SHP2) were found in about 50% of NS cases and in almost all LS patients having certain characteristics of NS. For NS, Y62D and Y63C in the protein are the most common mutations. These two mutations affect the non-catalytic activity conformation of SHP2, but do not interfere with the binding of phosphatase and its phosphorylated signaling ligand.

Juvenile myelomonocytic leukemia (JMML)—Somatic mutations in PTPN11 (SHP2) occur in approximately 35% of patients with JMML (a childhood myelodysplastic disease (MPD)). These gain-of-function mutations are usually point mutations in the N-SH2 domain or the phosphatase domain, which prevent the self-inhibition between the catalytic domain and the N-SH2 domain to produce SHP2 activity.

Acute myeloid leukemia—PTPN11 mutations have been identified in about 10% of pediatric acute leukemias such as myelodysplastic syndrome (MDS), about 7% of B-cell acute lymphoblastic leukemia (B-ALL) and about 4% of acute myeloid leukemia (AML).

NS and leukemia mutations cause changes of the amino acids at the interface formed by the N-SH2 and PTP domains in the self-inhibiting SHP2 conformation, disrupt inhibitory intramolecular interactions, and result in hyperactivity of the catalytic domain.

SHP2 acts as a positive regulator in receptor tyrosine kinase (RTK) signaling. Cancers containing RTK changes ($EGFR^{amp}$, $Her2^{amp}$, $FGFR^{amp}$, $Met^{amp}$, translocated/activated RTK, namely ALK, BCR/ABL) include esophageal cancer, breast cancer, lung cancer, colon cancer, gastric cancer, glioma, and head and neck cancer.

Esophageal cancer (or esophagus cancer) is a malignant disease of the esophagus. There are many subtypes of esophageal cancer, mainly squamous cell carcinoma (<50%) and adenocarcinoma. There is a higher rate of RTK expression in esophageal adenocarcinoma and squamous cell carcinoma. Therefore, the SHP2 inhibitor of the disclosure can be used for innovative treatment strategies.

Breast cancer is an important type of cancer and the leading cause of death in women, where patients develop resistance to existing drugs. There are four main breast cancer subtypes, including luminal A, luminal B, Her2lik and triple-negative/Basal-like. Triple-negative breast cancer (TNBC) is an invasive breast cancer that lacks specific targeted therapies. Epidermal growth factor receptor I (EGFR) has been shown as a promising target in TNBC. Inhibition of HER2 and EGFR via SHP2 may be a promising treatment for breast cancer.

Lung cancer—NSCLC is currently an important cause of cancer-related mortality. It accounts for about 85% of lung cancer (mainly adenocarcinoma and squamous cell carcinoma). Although cytotoxic chemotherapy is still an important part of treatment, targeted therapies based on genetic changes (such as EGFR and ALK) in tumors are more likely to benefit from targeted therapy.

Colon cancer—About 30% to 50% of colorectal tumors are known to have mutated (abnormal) KRAS, and BRAF mutations occur in 10% to 15% of colorectal cancers. For a subgroup of patients whose colorectal tumors have been shown to overexpress EGFR, these patients present a favorable clinical response to anti-EGFR therapy.

Gastric cancer is one of the most popular types of cancer. The abnormal expression of tyrosine kinase (as reflected by abnormal tyrosine phosphorylation in gastric cancer cells) is known in the art. Three receptor tyrosine kinases, namely c-met (HGF receptor), FGF receptor 2 and erbB2/neu, are often amplified in gastric cancer. Therefore, the destruction of different signaling pathways can promote the progression of different types of gastric cancer.

Neuroblastoma is a pediatric tumor of the developing sympathetic nervous system, accounting for about 8% of childhood cancers. Genomic changes of anaplastic lymphoma kinase (ALK) gene have been proposed to promote the pathogenesis of neuroblastoma.

Squamous cell carcinoma of the head and neck (SCCHN)—High levels of EGFR expression are associated with poor prognosis and resistance to radiotherapy in a variety of cancers, most commonly squamous cell carcinoma of the head and neck (SCCHN). Blocking of EGFR signal leads to the inhibition of receptor stimulation and the decrease of cell proliferation, invasion and metastasis. Therefore, EGFR is the best target of new anticancer therapy in SCCHN.

The present disclosure relates to compounds capable of inhibiting SHP2 activity. The disclosure also provides a preparation method of the compound of the disclosure and a pharmaceutical preparation containing the compound. Another aspect of the disclosure relates to a method of treating a SHP2-mediated disease or condition, which comprises a step of administering to a patient in need thereof a therapeutically effective amount of the compound of Formula I of the disclosure.

In some embodiments, the disclosure relates to the method as described above, wherein the SHP2-mediated disease or condition is selected from but not limited to the following cancers: JMML, AML, MDS, B-ALL, neuroblastoma, esophageal cancer, breast cancer, lung cancer, colon cancer, stomach cancer, head and neck cancer.

The compound of the disclosure also may be used for treating other diseases or conditions related to abnormal SHP2 activity. Therefore, as a preferred embodiment, the disclosure relates to a method for treating a disease or condition selected from: NS, LS, JMML, AML, MDS, B-ALL, neuroblastoma, esophageal cancer, breast cancer, lung cancer, colon cancer, stomach cancer, head and neck cancer.

The SHP2 inhibitors of the present disclosure may be combined with another pharmacologically active compound or with two or more other pharmacologically active compounds, especially in the treatment of cancer. For example, the compound of Formula (I) of the present disclosure or a pharmaceutically acceptable salt thereof may be administered simultaneously, sequentially, or separately in combination with one or more substances selected from: chemotherapeutic agents, such as mitotic inhibitors, such as taxane, vinca alkaloids, paclitaxel, docetaxel, vincristine, vinblastine, vinorelbine or vinflunine, and other anticancer agents, such as cisplatin, 5-fluorouracil or 5-fluoro-2-4(1H,3H)-pyrimidinedione (5FU), flutamide or gemcitabine.

Some combinations can provide significant benefits in therapy, including synergistic activity.

In some embodiments, the disclosure relates to the method as described above, wherein the compound is administrated parenterally.

In some embodiments, the disclosure relates to the method as described above, wherein the compound is administered intramuscularly, intravenously, subcutaneously, orally, pulmonaryly, intrathecally, topically or intranasally.

In some embodiments, the disclosure relates to the method as described above, wherein the compound is administered systemically.

In some embodiments, the disclosure relates to the method as described above, wherein the patient is a mammal.

In some embodiments, the disclosure relates to the method as described above, wherein the patient is a primate.

In some embodiments, the disclosure relates to the method as described above, wherein the patient is a human.

In some embodiments, the disclosure relates to the method of treating a SHP2-mediated disease or condition, wherein the method comprises the following step: administering to a patient in need thereof a combination of a therapeutically effective amount of chemotherapeutic agent and a therapeutically effective amount of the compound of Formula I of the disclosure.

The main advantages of the disclosure include:

1. The disclosure provides a compound of Formula I.
2. The disclosure provides a novel structure SHP2 inhibitor and its preparation and use, and the inhibitor has a high inhibitory activity on SHP2.
3. The disclosure provides a pharmaceutical composition for the treatment of SHP2-related diseases or conditions.

The disclosure is further described below in combination with specific examples. It should be understood that these examples are only used to illustrate the present disclosure and not to limit the scope of the present disclosure. The experimental methods without specific conditions in the following examples generally follow the conventional conditions or the conditions recommended by the manufacturer. Unless otherwise stated, percentages and parts are calculated by weight.

The starting materials used in the following examples can be purchased from chemical distributors such as Aldrich, TCI, Alfa Aesar, Bide, Energy, etc., or can be synthesized by known methods.

The meanings of the English abbreviations involved in the following examples are described in the following table.

| | | | |
|---|---|---|---|
| Ti(OEt)$_4$ | tetraethyl titanate | DMF | N,N-dimethylformamide |
| LiBH$_4$ | lithium borohydride | Na$_2$CO$_3$ | sodium carbonate |
| TFA | trifluoroacetic acid | EtOH | ethyl alcohol |
| LDA | N,N-lithium diisopropylamine | CBr$_4$ | carbon tetrabromide |
| Pd(AmPhos)$_2$Cl$_2$ | bis(di-tert-butyl(4-dimethylaminophenyl)phosphine)dichloropalladium(II) | Ph$_3$P | triphenylphosphine |
| | | NBS | N-bromosuccinimide |
| | | BPO | benzoyl peroxide |
| Cs$_2$CO$_3$ | cesium carbonate | TMP | 2,2,6,6-tetramethylpiperidine |
| DMAc or DMA | N,N-dimethylacetamide | PBr$_3$ | phosphorus tribromide |
| | | CCl$_4$ | carbon tetrachloride |
| THF | tetrahydrofuran | N$_2$H$_4$ | hydrazine |
| DCM | dichloromethane | H$_2$SO$_4$ | sulfuric acid |
| Ms$_2$O | methyl sulfonic anhydride | POCl$_3$ | phosphorus oxychloride |
| n-BuLi | n-butyllithium | Pd(OAc)$_2$ | palladium acetate |
| Dibal-H | diisobutyl aluminum hydride | EtONa | sodium ethoxide |
| Dioxane | 1,4-dioxane | Pd$_2$(dba)$_3$ | tris(dibenzylideneacetone)dipalladium |
| PPA | polyphosphoric acid | | |
| NaBH$_4$ | sodium borohydride | XantPhos | 4,5-bis(diphenylphosphino)-9,9-dimethylxanthene |
| MeOH | methyl alcohol | | |

| | | | |
|---|---|---|---|
| Et₃N or TEA | triethylamine | CH₃CN | acetonitrile |
| | | Boc₂O | di-tert-butyl dicarbonate |
| DIPEA | N,N-diisopropylethylamine | K₂CO₃ | potassium carbonate |
| HCl | hydrogen chloride | | |
| PMB-Br | 4-methoxybenzyl bromide | | |

In the following examples, the ice bath refers to −5° C. to 0° C., the room temperature refers to 10° C. to 30° C., and the reflux temperature generally refers to the reflux temperature of the solvent under normal pressure. Overnight reaction generally refers to a time of 8-15 hours. In the following examples, operations without a specific operating temperature are all carried out at room temperature.

In the following examples, the separation and purification of the intermediate and final products are performed by normal phase or reversed phase chromatography column separation or other suitable methods. Normal phase flash chromatography columns use ethyl acetate and n-hexane or methanol and methylene chloride as mobile phases. Reversed phase preparative high-pressure liquid chromatography (HPLC) uses a C18 column and UV at 214 nm and 254 nm with mobile phases A (water and 0.1% formic acid) and B (acetonitrile), or mobile phases A (water and 0.1% Ammonium bicarbonate) and B (acetonitrile).

In the examples: LCMS instrument: Pump Agilent 1260, UV detector: Agilent 1260 DAD Mass Spectrometer API 3000;

Chromatography column: Waters sunfire C18, 4.6×50 mm, 5 um;

Mobile phases: A-H₂O (0.1% HCOOH); B-acetonitrile

NMR instrument: Bruker Ascend 400M (1H NMR: 400 MHz; 13C NMR: 100 MHz).

Synthesis of intermediate A1: (R)—N—((S)-1,3-dihydrospiro[indene-2,4'-piperidin-1-yl)-2-methyl-propane-2-sulfinamide

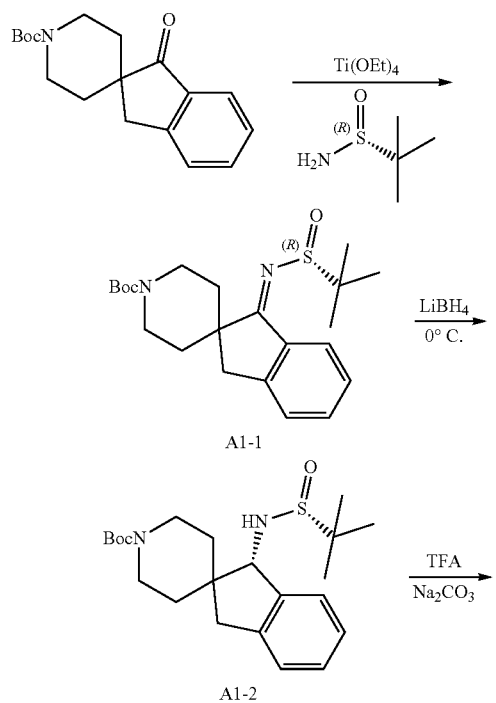

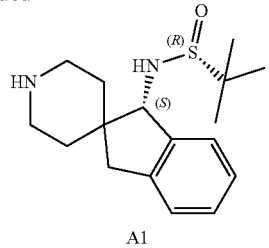

A1

Step 1: 1-oxo-1,3-dihydrospiro[indene-2,4'-piperidine]-1'-carboxylic acid tert-butyl ester (1.51 g, 5 mmol), tetraethyl titanate (6.84 g, 30 mmol) and (R)-(+)-tert-butylsulfinamide (2.41 g, 20 mmol) were successively added to a dry 100 mL single-necked flask, and the mixture was stirred under heating and reflux for 15 hours. After the reaction system was cooled to room temperature, saturated brine (60 mL) was added to the reaction residue, after which the resulting mixture was stirred for 15 minutes and then filtered through diatomite. The aqueous mixture was extracted with ethyl acetate (3×80 mL). The organic phase was dried over Na₂SO₄ and filtered, and volatiles were removed under reduced pressure. The resulting residue was purified by silica gel chromatography (0 to 30% gradient ethyl acetate: petroleum ether) to obtain (R,Z)-1-((tert-butyl sulfinyl)imino)-1,3-dihydrospiro[indene-2,4'-piperidine]-1'-carboxylic acid tert-butyl ester (A1-1, 1.61 g, yield: 80%) as a white solid.

¹H NMR (400 MHz, CDCl₃) δ 8.34 (d, J=7.2 Hz, 1H), 7.48-7.39 (m, 1H), 7.35-7.28 (m, 2H), 4.21-3.92 (m, 2H), 3.00 (s, 2H), 2.88 (t, J=11.9 Hz, 2H), 2.00-1.80 (m, 2H), 1.48-1.30 (m, 11H), 1.24 (d, J=13.1 Hz, 9H); LCMS: m/z 405.1 [M+H]⁺.

Step 2: (R,Z)-1-((tert-butylsulfinyl)imino)-1,3-dihydrospiro[indene-2,4'-piperidine]-1'-carboxylic acid tert-butyl ester (A1-1, 0.802 g, 2 mmol) and THF (10 mL) were successively added to a dry 100 mL single-necked flask, the mixture was cooled to 0° C., and then lithium borohydride (66 mg, 3 mmol) was added. The resulting mixture was then stirred for 1 hour. Methanol was slowly added to quench excess borohydride. The reaction solution was filtered, and concentrated, and volatiles were removed under reduced pressure. The resulting residue was purified by silica gel chromatography (0 to 50% gradient ethyl acetate:petroleum ether) to obtain (S)-1-(((R)-tert-butylsulfinyl)amino)-1,3-dihydrospiro[indene-2,4'-piperidine]-1'-carboxylic acid tert-butyl ester (A1-2, 0.63 g, yield: 78%) as a light yellow solid.

¹H NMR (400 MHz, DMSO) δ 7.30-7.15 (m, 4H), 5.64 (d, J=10.5 Hz, 1H), 4.38 (d, J=10.5 Hz, 1H), 3.86 (s, 2H), 3.05 (d, J=15.8 Hz, 1H), 2.87 (s, 2H), 2.62 (d, J=15.8 Hz, 1H), 1.89 (s, 1H), 1.61-1.35 (m, 12H), 1.27-1.10 (m, 11H); LCMS: m/z 407.1 [M+H]⁺.

Step 3: (S)-1-(((R)-tert-butylsulfinyl)amino)-1,3-dihydrospiro[indene-2,4'-piperidine]-1'-carboxylic acid tert-butyl ester (A1-2, 0.406 g, 1 mmol), dichloromethane (5 mL), and TFA (1 mL) were successively added to a dry 50 mL single-necked flask, and the resulting mixture was stirred at room temperature for 1 hour. Na₂CO₃ saturated aqueous solution was added until pH reached 7, and the aqueous mixture was extracted with DCM (3×30 mL). The combined organic phase was washed with brine, dried over Na₂SO₄, and filtered, and the volatiles were removed under reduced pressure. The resulting residue was cooled to obtain (R)—N—((S)-1,3-dihydrospiro[indene-2,4'-piperidine]-1-yl)-2-methylpropane-2-sulfinamide (A1, 0.183 g, yield: 70%) as a colorless oily matter.

¹H NMR (400 MHz, CDCl₃) δ 7.26-7.11 (m, 5H), 4.45 (d, J=10.1 Hz, 1H), 3.77 (s, 1H), 3.18 (s, 2H), 3.04 (d, J=15.9 Hz, 3H), 2.67 (d, J=15.8 Hz, 1H), 2.20 (td, J=12.7, 3.5 Hz, 1H), 1.82 (t, J=11.1 Hz, 1H), 1.61 (d, J=12.9 Hz, 1H), 1.34-1.11 (m, 10H); LCMS: m/z 307.1 [M+H]⁺.

Synthesis of Intermediate A2: R—N—((S)-5,7-dihydrospiro[cyclopenta[b]pyridine-6,4'-piperidine]-5-yl)-2-methylpropane-2-sulfinamide

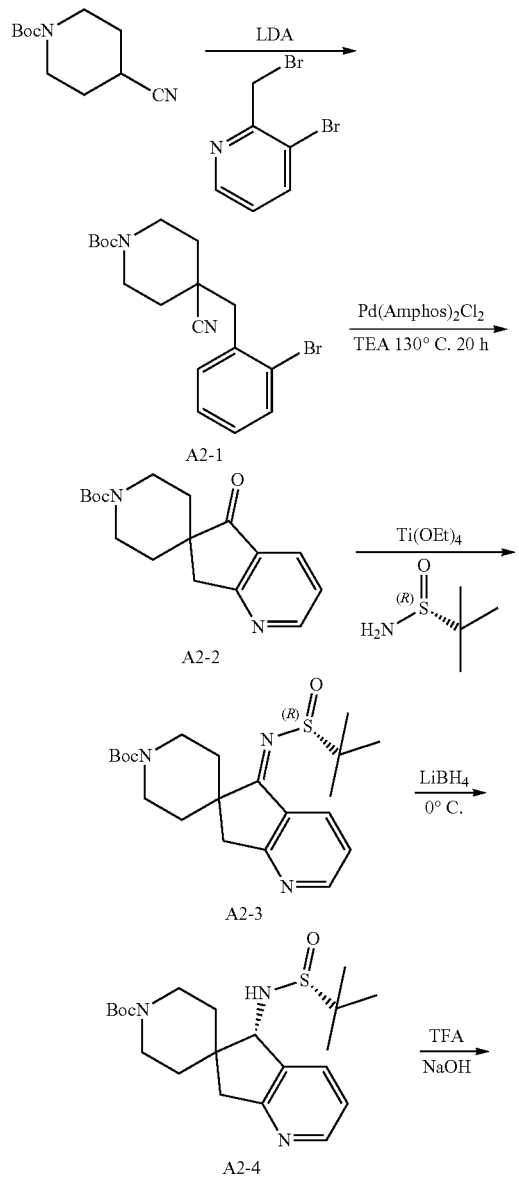

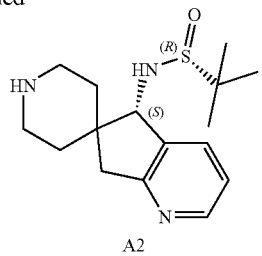

Step 1: 4-cyanopiperidine-1-carboxylic acid tert-butyl ester (1.05 g, 5 mmol) and THF (20 mL) were successively added to a dry 100 mL flask. Under the protection of nitrogen, the mixture was cooled to −78° C., and then 2M of LDA (3.3 mL, 6.5 mmol) was slowly added to the reaction mixture. The reaction mixture was allowed to react for 1 hour, and then 3-bromo-2-(bromomethyl)pyridine (1.24 g, 5 mmol) was added thereto, and then the reaction mixture was allowed to continue to react for 2 hours. After the reaction, saturated ammonium chloride solution (15 ml) was added to quench the reaction, the resulting mixture was extracted with ethyl acetate (3×30 ml), the organic layers were combined, washed with saturated brine, dried over anhydrous sodium sulfate and filtered, and the residue obtained by concentration under reduced pressure was purified by silica gel chromatography (0 to 30% gradient of ethyl acetate/petroleum ether) to obtain 4-((3-bromopyridine-2-yl)methyl)-4-cyanopiperidine-1'-carboxylic acid tert-butyl ester (A2-1, 1.40 g, yield: 75%) as a white solid.

Step 2: Under the protection of nitrogen, 4-((3-bromopyridine-2-yl)methyl)-4-cyanopiperidine-1'-carboxylic acid tert-butyl ester (A2-1, 379 mg, 1 mmol), trimethylamine (404 mg, 4 mmol), bis(di-tert-butyl(4-dimethylaminophenyl)phosphine)dichloropalladium(II) Pd(AmPhos)₂Cl₂ (71 mg, 0.1 mmol) and DMA:H₂O=10:1 (6 mL) were successively added to a dry 25 mL single-necked flask, and then the mixture was stirred at 130° C. for 18 hours. After the reaction was completed, the obtained residue was filtered and the residue obtained by concentration under reduced pressure was purified by silica gel chromatography (0 to 50% gradient of ethyl acetate:petroleum ether) to obtain 5-oxo-5,7-dihydrospiro[cyclopenta[b]pyridine-6,4'-piperidine]-1'-carboxylic acid tert-butyl ester (A2-2, 180 mg, yield: 60%) as a yellow solid. LCMS: m/z 303.1 [M+H]⁺.

Step 3: 5-oxo-5,7-dihydrospiro[cyclopenta[b]pyridine-6,4'-piperidine]-1'-carboxylic acid tert-butyl ester (A2-2, 0.302 g, 1 mmol), tetraethyl titanate (1.37 g, 6 mmol) and (R)-(+)-tert-butylsulfinamide (0.480 g, 4 mmol) were successively added to a dry 100 mL single-necked flask and the mixture was stirred under heating and reflux for 15 hours. After the reaction system was cooled to room temperature, saturated brine (15 mL) was added to the reaction residue, after which the resulting mixture was stirred for 15 minutes and then filtered through diatomite. The aqueous mixture was extracted with ethyl acetate (3×300 mL). The organic phase was dried over Na₂SO₄ and filtered, and volatiles were removed under reduced pressure. The resulting residue was purified by silica gel chromatography (0 to 50% gradient of ethyl acetate:petroleum ether) to obtain (R,Z)-5-((tert-butylsulfinyl)imino)-5,7-dihydrospiro[cyclopenta[b]pyridine-6,4'-piperidine]-1'-carboxylic acid tert-butyl ester (A2-3, 0.333 g, yield: 82%) as a yellow solid. LCMS: m/z 406.1 [M+H]⁺.

Step 4: (R,Z)-5-((tert-butylsulfinyl)imino)-5,7-dihydrospiro[cyclopenta[b]pyridine-6,4'-piperidine]-1'-carboxylic acid tert-butyl ester (A2-3, 0.20 g, 0.491 mmol) and THF (50 mL) were successively added to a dry 100 mL single-necked flask, the mixture was cooled to 0° C., and then lithium borohydride (0.018 g, 0.737 mmol) was added. The resulting mixture continued to react with stirring for 1 hour. Methanol was slowly added to quench excess borohydride. The reaction solution was filtered, and concentrated, and volatiles were removed under reduced pressure. The resulting residue was purified by silica gel chromatography (0 to 80% gradient of ethyl acetate:petroleum ether) to obtain (S)-5-((R)-tert-butylsulfonamido)-dihydrospiro[cyclopenta[b]pyridine-6,4'-piperidine]-1'-carboxylic acid tert-butyl ester (A2-4, 0.130 g, yield: 65%) as a white solid. LCMS: m/z 408.1 [M+H]$^+$.

Step 5: (S)-5-((R)-tert-butylsulfonamido)-dihydrospiro[cyclopenta[b]pyridine-6,4'-piperidine]-1'-carboxylic acid tert-butyl ester (A2-4, 0.100 g, 0.245 mmol), dichloromethane (5 mL), and TFA (1 mL) were successively added to a dry 50 mL single-necked flask, and the resulting mixture was reacted with stirring at room temperature for 1 hour. Na$_2$CO$_3$ saturated aqueous solution was added until pH reached 7, and the aqueous mixture was extracted with DCM (3×30 mL). The combined organic phase was washed with brine, dried over Na$_2$SO$_4$, and filtered, and the volatiles were removed under reduced pressure. The resulting residue was cooled to obtain R—N—((S)-5,7-dihydrospiro[cyclopenta[b]pyridine-6,4'-piperidine]-5-yl)-2-methylpropane-2-sulfinamide (A2, 0.056 g, yield: 75%) as a colorless oily matter. LCMS: m/z 308.1 [M+H]$^+$.

Synthesis of Intermediate A3: (S)-1,3-dihydrospiro[indene-2,4'-piperidine]-1-amine

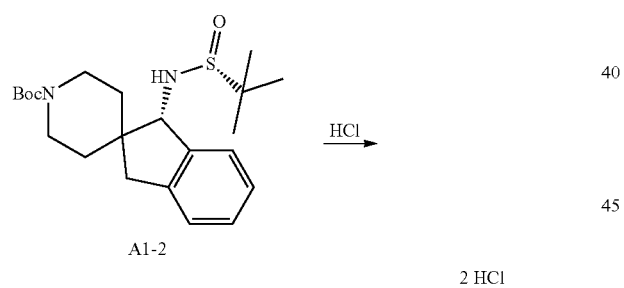

Step: Methyl alcohol (1 mL), dichloromethane (1 mL) and A1-2 (540 mg, 1.33 mmol, 1.0 eq) were added to a dry 100 mL round-bottom flask. HCl/1,4-dioxane (3.3 mL, 4 M) was added dropwise at room temperature, white solid precipitated, and the reaction system was heated to 50° C. and stirred for 2 hours. After the reaction was completed, the reaction mixture was concentrated under reduced pressure to obtain (S)-1,3-dihydrospiro[indene-2,4'-piperidine]-1-amine (A3, 373 mg, yield: 97.1%, HCl salt) as a white solid. LCMS: m/z 203.1 [M+H]$^+$.

Synthesis of Intermediate A4: (S)-5,7-dihydrospiro[cyclopenta[b]pyridine-6,4'-piperidine]-5-amine

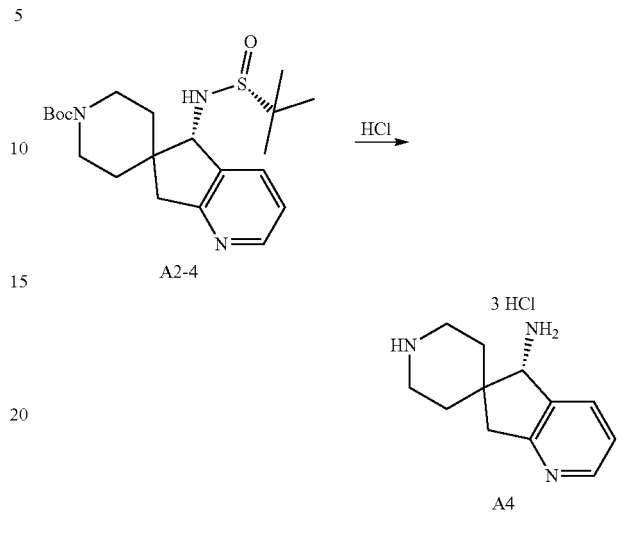

Intermediate (S)-5,7-dihydrospiro[cyclopenta[b]pyridine-6,4'-piperidine]-5-amine (A4) was synthesized according to the synthesis protocol of intermediate A3, using intermediate A2-4 instead of intermediate A1-2. LCMS: m/z 204.1 [M+H]$^+$.

Synthesis of intermediate A5: (S)-5,7-dihydrospiro[cyclopenta[c]pyridine-6,4'-piperidine]-7-amine

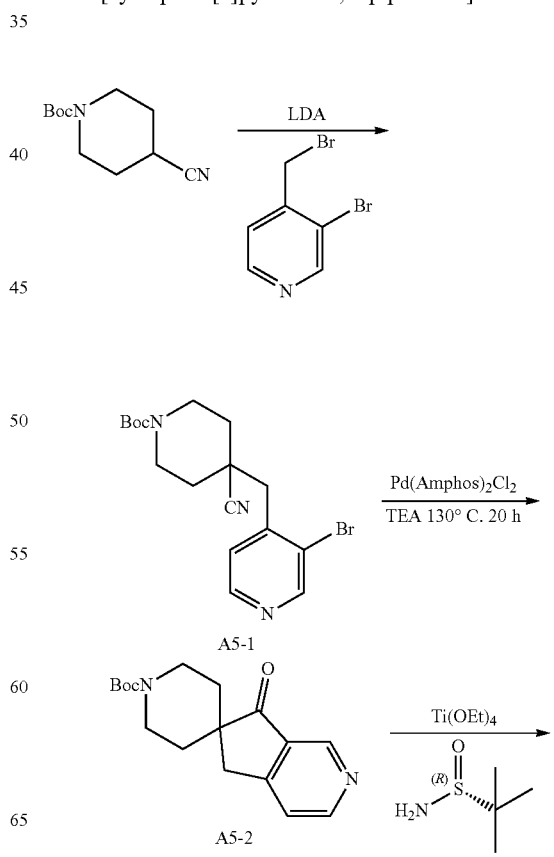

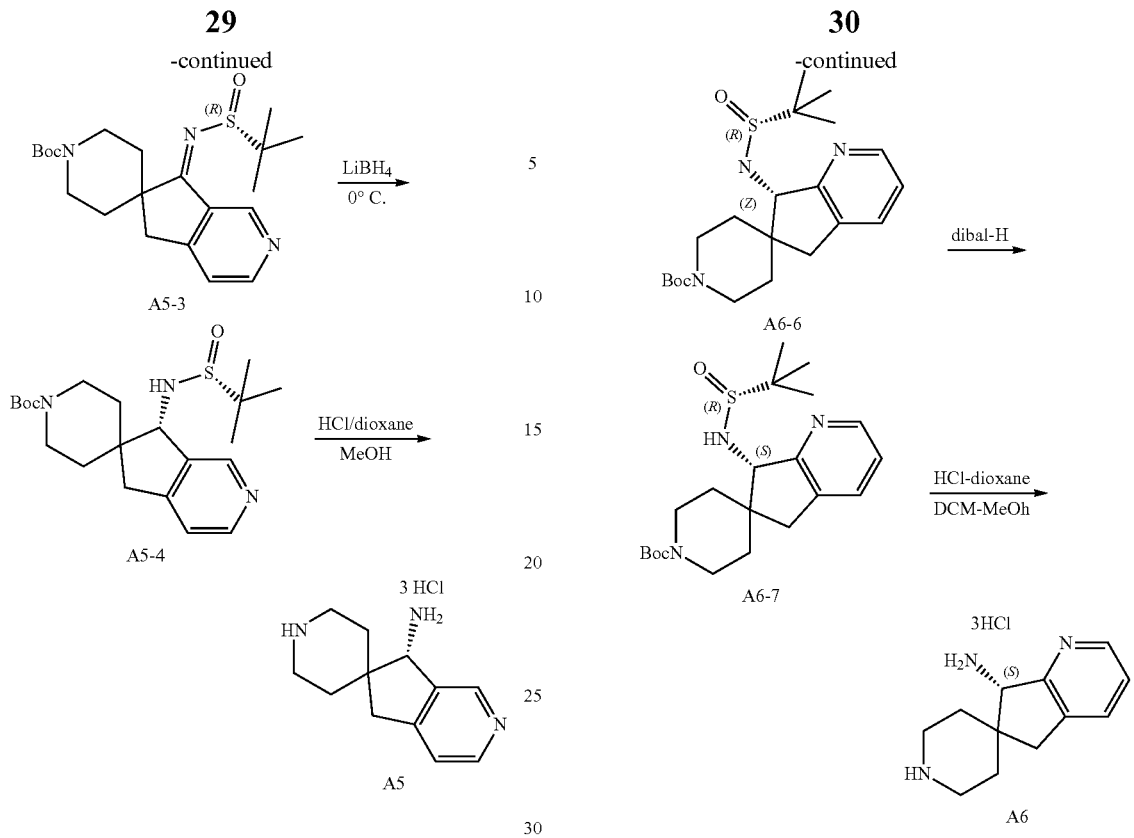

A5 was synthesized according to the synthesis protocol of intermediate A2 and A3. LCMS: m/z 204.1 [M+H]+.

Synthesis of Intermediate A6: (S)-5,7-dihydrospiro[cyclopenta[b]pyridine-6,4'-piperidine]-7-amine

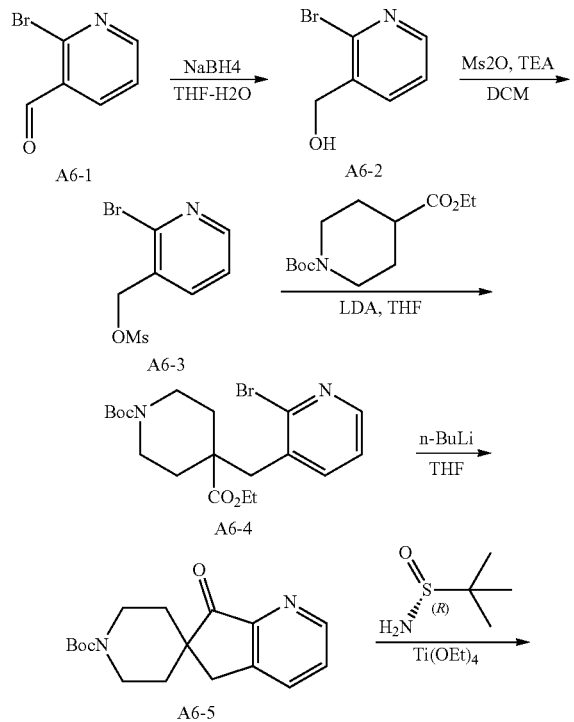

Step 1: A6-1 (11.1 g, 60 mmol) and NaBH$_4$ (2.51 g, 66 mmol) were successively added to 300 mL of THF and 60 mL of H$_2$O in a 1 L flask, and the mixture was reacted at 20° C. for 2 hours. After the raw materials were confirmed to be completely reacted by spot plate detection, the reaction mixture was quenched with saturated NH$_4$Cl solution, diluted with water, and extracted with ethyl acetate. The combined organic phase was washed with saturated NaCl solution, dried over anhydrous sodium sulfate, filtered and concentrated under reduced pressure to obtain 2-bromopyridin-3-ylmethanol (A6-2, 11.2 g, yield: 100%) as a white solid.

Step 2: A6-2 (6.73 g, 36 mmol) and Ms$_2$O (6.96 g,g, 40 mmol) were successively added to 120 mL of dichloromethane in a dry 250 mL single-necked flask, then the mixture was cooled to 0° C., then TEA (5.45 g, 54 mmol) was slowly added, and then the mixture was heated to room temperature and stirred for 3 hours. After the reaction was completed, the reaction solution was washed with water. The organic phase was dried over anhydrous sodium sulfate, filtered, and concentrated under reduced pressure. The resulting residue was purified by silica gel chromatography (0 to 10% gradient of ethyl acetate/dichloromethane) to obtain methylsulfonic acid (2-bromopyridin-3-yl)methyl ester (A6-3, 8.02 g, yield: 84%) as a colorless oily matter.

Step 3: 4-ethoxycarbonylpiperidine-1-carboxylic acid tert-butyl ester (9.3 g, 36.2 mmol) and THF (133 mL) were successively added to a dry 500 mL three-necked flask. Under the protection of nitrogen, the mixture was cooled to −70° C., and then 2M of LDA (21.1 mL, 42.3 mmol) was slowly added to the reaction mixture. The reaction mixture was allowed to react for 1 hour, then methylsulfonic acid (2-bromopyridin-3-yl)methyl ester (A6-3, 8.0 g, 30.2 mmol) dissolved in 65 mL of THF was added thereto, then the reaction mixture was allowed to continue to react for 0.5 hours, and then the reaction mixture was slowly heated to room temperature and stirred for 1 hour. After the reaction was completed, the reaction mixture was quenched by saturated brine and extracted with ethyl acetate. The organic phases were combined, washed with saturated brine, dried over anhydrous sodium sulfate, filtered and concentrated under reduced pressure. The obtained residue was purified by silica gel chromatography (8 to 12% gradient of ethyl acetate/dichloromethane) to obtain 4-ethoxycarbonyl-4-(2-bromo-3-pyridyl)methyl-piperidine-1-carboxylic acid tert-butyl ester (A6-4, 10.5 g, yield: 81%) as a colorless oily matter.

Step 4: 4-ethoxycarbonyl-4-(2-bromo-3-pyridyl)methyl-piperidine-1-carboxylic acid tert-butyl ester (A6-4, 7.85 g, 18.4 mmol) and THF (120 mL) were successively added to a dry 250 mL three-necked flask. Under the protection of nitrogen, the mixture was cooled to −70° C., and then 2.5 M of n-butyllithium (111 mL, 27.6 mmol) was slowly added to the reaction mixture. The reaction mixture was allowed to react for 1.5 hours. After the reaction was completed, saturated ammonium chloride aqueous solution was added thereto to quench the reaction, and then saturated brine was added to dilute and separate the liquid. The aqueous phase was extracted with ethyl acetate. The organic phases were combined, washed with saturated brine, dried over anhydrous sodium sulfate, filtered and concentrated under reduced pressure. The obtained residue was purified by silica gel chromatography (0 to 60% gradient of ethyl acetate/petroleum ether) to obtain 7-oxo-5,7-dihydrospiro[cyclopenta[b]pyridine-6,4'-piperidine]-1'-carboxylic acid tert-butyl ester (A6-5, 1.4 g, yield: 25%) as a light brown solid.

Step 5: Intermediate (R,Z)-7-((tert-butylsulfinyl)imino)-5,7-dihydrospiro[cyclopenta[b]pyridine-6,4'-piperidine]-1'-carboxylic acid tert-butyl ester (A6-6, 1.46 g, yield: 68%) was synthesized according to the synthesis protocol of intermediate A2-3, using intermediate A6-5 instead of intermediate A2-2.

Step 6: (R,Z)-7-((tert-butylsulfinyl)imino)-5,7-dihydrospiro[cyclopenta[b]pyridine-6,4'-piperidine]-1'-carboxylic acid tert-butyl ester (A6-6, 530 mg, 1.31 mmol) and THF (10 mL) were successively added to a dry 50 mL three-necked flask. Under the protection of nitrogen, the mixture was cooled to −70° C., and then 1.5 M of diisobutylaluminum hydride in toluene (1.3 mL, 1.95 mmol) was slowly added to the reaction mixture. The reaction mixture was allowed to react for 0.5 hours, and then the mixture was slowly heated to room temperature, quenched with saturated potassium sodium tartrate aqueous solution and stirred for 0.5 hours. The reaction mixture was extracted with ethyl acetate. The organic phases were combined, washed with saturated brine, dried over anhydrous sodium sulfate, filtered and concentrated under reduced pressure. The obtained residue was purified by silica gel chromatography (0 to 5% gradient of methyl alcohol/dichloromethane) to obtain (S)-7-((R)-tert-butylsulfonamido)-5,7-dihydrospiro[cyclopenta[b]pyridine-6,4'-piperidine]-1'-carboxylic acid tert-butyl ester (A6-7, 466 mg, yield: 87%) as a light yellow foamy solid.

Step 7: (S)-7-((R)-tert-butylsulfonamido)-5,7-dihydrospiro[cyclopenta[b]pyridine-6,4'-piperidine]-1'-carboxylic acid tert-butyl ester (A6-7, 312 mg, 0.766 mmol), MeOH (5 mL), and 4M of HCl/1,4-dioxane solution (3.83 mL, 15.3 mmol) were successively added to a dry 25 mL single-necked flask, and then the mixture was heated to 50° C. and reacted for 8 hour to obtain a white suspension. The suspension was concentrated under reduced pressure to obtain (S)-5,7-dihydrospiro[cyclopenta[b]pyridine-6,4'-piperidine]-7-amine HCl salt (A6, 232 mg, yield: 97%) as a whit solid. LCMS: m/z 204.1 [M+H]$^+$.

Synthesis of Intermediate A7: (S)-6-fluoro-1,3-dihydrospiro[indene-2,4'-piperidine]-1-amine

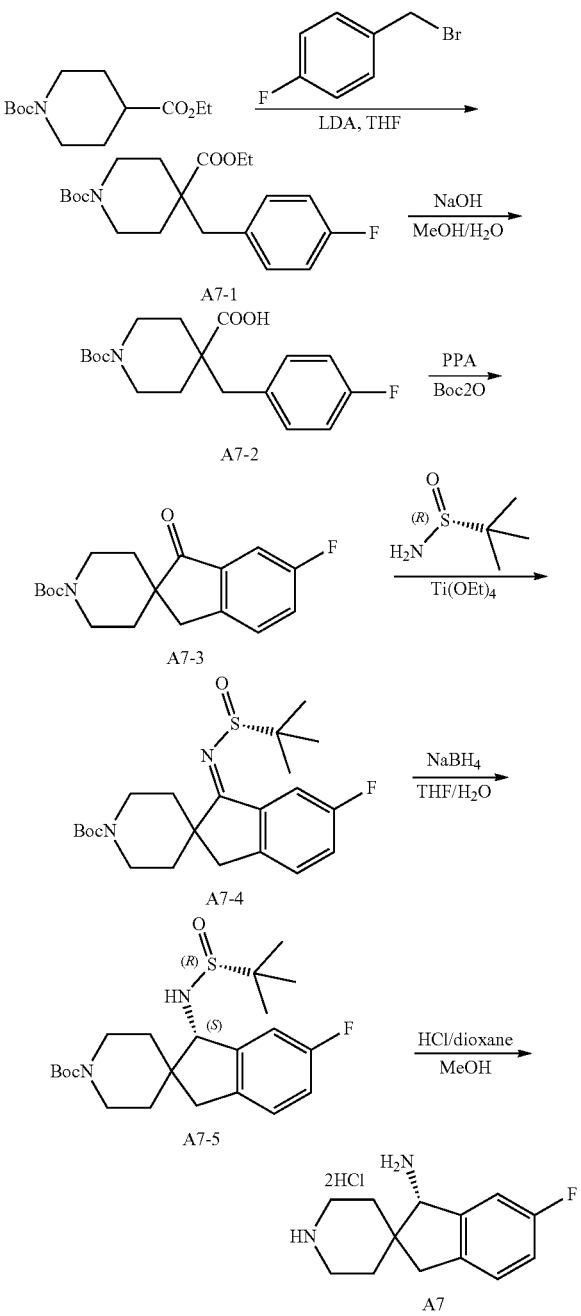

Step 1: Intermediate 4-ethoxycarbonyl-4-(4-fluorobenzyl)-pyridine-1-carboxylic acid tert-butyl ester A7-1 was synthesized according to the synthesis protocol of intermediate A2, using raw material 4-fluorobenzyl bromide instead of raw material 3-bromo-2(bromomethyl)pyridine.

Step 2: 4-ethoxycarbonyl-4-(4-fluorobenzyl)-pyridin-1-carboxylic acid tert-butyl ester (A7-1, 3.40 g, 9.30 mmol) and sodium hydroxide (1.86 g, 46.5 mmol) were successively added to 20 mL of methyl alcohol and 20 mL of water in a 100 mL single-necked flask. The reaction solution was reacted at 70° C. for 17 hours. The reaction mixture was cool to room temperature, and then concentrated under reduced pressure to get rid of the volatiles. The obtained residue was diluted with water (50 mL) and dilute hydrochloric acid was added to adjust pH to 3, and then the mixture was extracted 3 times with ethyl acetate (80 mL). The organic phases were combined, washed with saturated brine, dried over anhydrous sodium sulfate, filtered and concentrated under reduced pressure to obtain 1-tert-butoxycarbonyl-4-(4-fluorobenzyl)-pyridine-4-carboxylic acid (A7-2, 3.0 g, crude product) as a yellow solid.

Step 3: 1-tert-butoxycarbonyl-4-(4-fluorobenzyl)-pyridine-4-carboxylic acid (A7-2, 2.0 g, 5.93 mmol) and PPA (15 mL) were successively added to a dry 50 mL single-necked flask. The reaction solution was reacted at 120° C. for 2 hours. The reaction solution was poured into ice-water mixture (50 mL) while it was still hot, and NaOH solid was added to adjust pH to 10.

Then, Boc$_2$O (1.94 g, 8.90 mmol) was added to the resulting mixture, and the reaction solution was stirred at 20° C. for 1 hour. The reaction solution was extracted 3 times with ethyl acetate (80 mL). The organic phases were combined, washed with saturated brine, dried over anhydrous sodium sulfate, filtered and concentrated under reduced pressure. The obtained residue was purified by silica gel chromatography (petroleum ether/ethyl acetate=5:1) to obtain 6-fluoro-1-oxo-1,3-dihydrospiro[indene-2,4'-piperidine]-1'-carboxylic acid tert-butyl ester (A7-3, 1.20 g, yield: 63.5%) as a yellow solid.

$^1$HNMR (400 MHz, CDCl$_3$) δ 7.46-7.38 (m, 2H), 7.37-7.30 (m, 1H), 4.20-4.06 (m, 2H), 3.07-2.95 (m, 4H), 1.96-1.85 (m, 2H), 1.48 (s, 9H), 1.44-1.35 (m, 2H).

Step 4: Intermediate (R,Z)-1-((tert-butylsulfinyl)imino)-6-fluoro-1-oxo-1,3-dihydrospiro[indene-2,4'-piperidine]-1'-formate A7-4 was synthesized according to the synthesis protocol of intermediate A2, using intermediate A7-3 instead of intermediate A2-2.

Step 5: (R,Z)-1-((tert-butylsulfinyl)imino)-6-fluoro-1-oxo-1,3-dihydrospiro[indene-2,4'-piperidine]-1'-formate (A7-4, 1.59 g, 3.76 mmol), tetrahydrofuran/water (98:2, 32 mL) and sodium borohydride (427 mg, 11.3 mmol) were successively added to a round-bottom flask at −50° C., and the reaction solution was heated to 20° C. in 3 hours undering stirring. The reaction was confirmed to be complete by TLC spot plate. The reaction solution was diluted with water (30 mL), and extracted 3 times with ethyl acetate (30 mL). The organic phases were combined, washed with saturated brine, dried over anhydrous sodium sulfate, filtered and concentrated under reduced pressure. The obtained residue was purified by silica gel chromatography (petroleum ether/ethyl acetate=2:1) to obtain (S)-1-(((R)-tert-butylsulfinyl)amino)-6-fluoro-1,3-dihydrospiro[indene-2,4'-piperidine]-1'-carboxylic acid tert-butyl ester (A7-5, 850 mg, yield: 53%) as a white solid.

Step 6: Intermediate (S)-6-fluoro-1,3-dihydrospiro[indene-2,4'-piperidine]-1-amine A7 was synthesized according to the synthesis protocol of intermediate A3, using intermediate A7-5 instead of intermediate A1-2. LCMS: m/z 220.1 [M+H]$^+$.

Intermediate A8: (S)-5,7-dihydrospiro[cyclopenta[c]pyridine-6,4'-piperidine]-7-amine

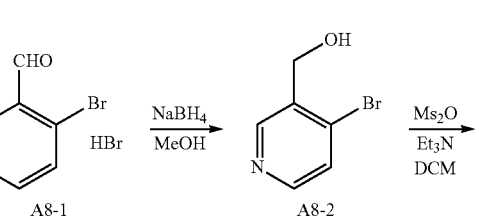

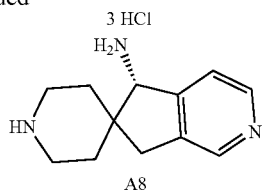

Step 1: 4-bromonicotinicaldehyde hydrobromide salt (A8-1, 2.5 g, 9.36 mmol) was dissolved in methyl alcohol (50 mL), sodium borohydride (0.72 g, 18.93 mmol, 2.0 eq) was added in batches in an ice bath, and the mixture was reacted at 0° C. for 1 hour. After the reaction was completed, saturated ammonium chloride aqueous solution (50 mL) was added in an ice bath to quench the reaction, and the reaction mixture was extracted with ethyl acetate (100 mL×2). The organic phases were combined, washed with saturated sodium chloride aqueous solution. The organic phase was separated, dried over anhydrous sodium sulfate, filtered and concentrated to obtain (4-bromopyridin-3-yl)methanol (A8-2, 1.7 g, yield: 100%) as a white solid. LCMS: m/z 190.3 [M+H]+

Step 2: (4-bromopyridin-3-yl)methanol (A8-2, 1.7 g, 9.04 mmol) was dissolved in dichloromethane (100 mL), and triethylamine (2.30 g, 22.7 mmol) was added in an ice bath. Under the protection of nitrogen, methanesulfonic anhydride (1.95 g, 11.2 mmol) was added in batches, the mixture was reacted at 0° C. for 2 hours, and then the reaction was completed. Saturated sodium chloride (50 mL) was added to quench the reaction in an ice bath, and the organic phase was separated and washed with saturated sodium chloride aqueous solution. The organic phase was dried over anhydrous sodium sulfate, filtered and concentrated to obtain methanesulfonic acid (4-bromopyridin-3-yl)methyl ester (A8-3, 1.7 g, yield: 70.7%) as a reddish brown solid. LCMS: m/z 266.2 [M+H]+

Step 3: 4-cyanopiperidine-1-carboxylic acid tert-butyl ester (1.61 g, 7.67 mmol) was dissolved in anhydrous tetrahydrofuran (60 mL). In a dry ice acetone bath (−78° C.) and the protection of nitrogen, LDA (4.6 mL, 9.2 mmol) was slowly added dropwise, the mixture was reacted for 0.5 hours while the temperature was maintained, and a lot of white solid precipitated from the reaction solution. A solution of methanesulfonic acid (4-bromopyridin-3-yl)methyl ester (A8-3, 1.7 g, 6.39 mmol) in anhydrous tetrahydrofuran (50 mL) was slowly added dropwise at −78° C., the mixture continued to be reacted for 2 hours while the temperature was maintained, and then the reaction was completed. Saturated ammonium chloride (100 mL) was added to quench the reaction, and the mixture was extracted with ethyl acetate (100 mL×3). The organic phases were combined and washed with saturated sodium chloride aqueous solution. The organic phase was dried over anhydrous sodium sulfate, filtered and concentrated. The residue was purified by silica gel chromatography (0 to 50% gradient of dichloromethane/petroleum ether) to obtain 4-((4-bromopyridin-3-yl)methyl)-4-cyanopiperidine-1-carboxylic acid tert-butyl ester (A8-4, 1.58 g, yield: 54%) as a white solid. LCMS: m/z 326.0 [M+H−56]+

Step 4: 4-((4-bromopyridin-3-yl)methyl)-4-cyanopiperidine-1-carboxylic acid tert-butyl ester (A8-4, 1.5 g, 3.95 mmol) was dissolved in DMAc/H$_2$O (100 mL/10 mL), DIPEA (1.34 g, 15.8 mmol) and Pd(AmPhos)$_2$Cl$_2$ (142 mg, 0.20 mmol) were added, the atmosphere in the reaction system was replaced with nitrogen three times, the mixture was reacted at 130° C. for 2 hours, and then the reaction was completed. Water (50 mL) was added, and the mixture was extracted with ethyl acetate (100 mL×3). The organic phases were combined and washed with saturated sodium chloride aqueous solution. The organic phase was dried over anhydrous sodium sulfate, filtered and concentrated. The residue was purified by silica gel chromatography to obtain 5-oxo-5,7-dihydrospiro[cyclopenta[c]pyridine-6,4'-piperidine]-1'-carboxylic acid tert-butyl ester (A8-5, 750 mg, yield: 62%) as a solid. LCMS: m/z 303.3 [M+H]+

Step 5: 5-oxo-5,7-dihydrospiro[cyclopenta[c]pyridine-6,4'-piperidine]-1'-carboxylic acid tert-butyl ester (A8-5, 750 mg, 2.48 mmol) was dissolved in THF (10 mL), and (R)-(+)-tert-butylsulfinamide (390 mg, 3.22 mmol) and tetraethyl titanate (10 mL) were added. Under the protection of nitrogen, the mixture was heated to 90° C. and refluxed for 18 hours. After the reaction was completed, the reaction mixture was cooled to room temperature and diluted with ethyl acetate (50 mL), saturated brine (10 mL) was added, and white solid precipitated. The mixture was filtered, and the filter cake was washed with ethyl acetate. The filtrate was washed with saturated brine, and the organic phase was dried over anhydrous sodium sulfate, filtered and concentrated. The crude product was purified by silica gel chromatography to obtain (R,Z)-5-((tert-butylsulfinyl)imino)-5,7-dihydrospiro[cyclopenta[c]pyridine-6,4'-piperidine]-1'-carboxylic acid tert-butyl ester (A8-6, 800 mg, yield: 80%) as a white solid. LCMS: m/z 406.2 [M+H]$^+$ Step 6: (R,Z)-5-((tert-butylsulfinyl)imino)-5,7-dihydrospiro[cyclopenta[c]pyridine-6,4'-piperidine]-1'-carboxylic acid tert-butyl ester (A8-6, 800 mg, 1.98 mmol) was dissolved in THF (50 mL), and the mixture was cooled to −78° C. under the protection of nitrogen. 1.5M of DIBAL-H (2 mL, 3 mmol) was slowly dripped into the reaction solution. After dripping was completed, the mixture was reacted at −78° C. for 1 hour, and then the reaction was completed. Water was added to quench the reaction, saturated potassium sodium tartrate solution (20 mL) was added, and the mixture was extracted with ethyl acetate (100 mL×2). The organic phase was washed once with saturated sodium chloride aqueous solution. The organic phase was separated, dried over anhydrous sodium sulfate, filtered and concentrated. The crude product was purified by silica gel chromatography to obtain (S)-5-(((R)-tert-butylsulfinyl)amino)-5,7-dihydrospiro[cyclopenta[c]pyridine-6,4'-piperidine]-1'-carboxylic acid tert-butyl ester (A8-7, 680 mg, yield: 84%) as a white solid. LCMS: m/z 408.3 [M+H]+

Step 7: (S)-5-(((R)-tert-butylsulfinyl)amino)-5,7-dihydrospiro[cyclopenta[c]pyridine-6,4'-piperidine]-1'-carboxylic acid tert-butyl ester (A8-7, 680 mg, 1.67 mmol) was dissolved in MeOH (50 mL), the mixture was cooled to 0° C., 4 M of hydrochloric acid dioxane solution (10 mL, 40 mmol) was added dropwise, the resulting mixture was react at room temperature for 3 hours, and then the reaction was completed. The reaction solution was concentrated to obtain (S)-5,7-dihydrospiro[cyclopenta[c]pyridine-6,4'-piperidine]-7-amine hydrochloride (A8, 400 mg, yield: 99%) as a white solid. LCMS: m/z 204.1 [M+H]$^+$ Intermediate A9: (S)-1-amino-1,3-dihydrospiro[indene-2,4'-piperidin]-4-ol

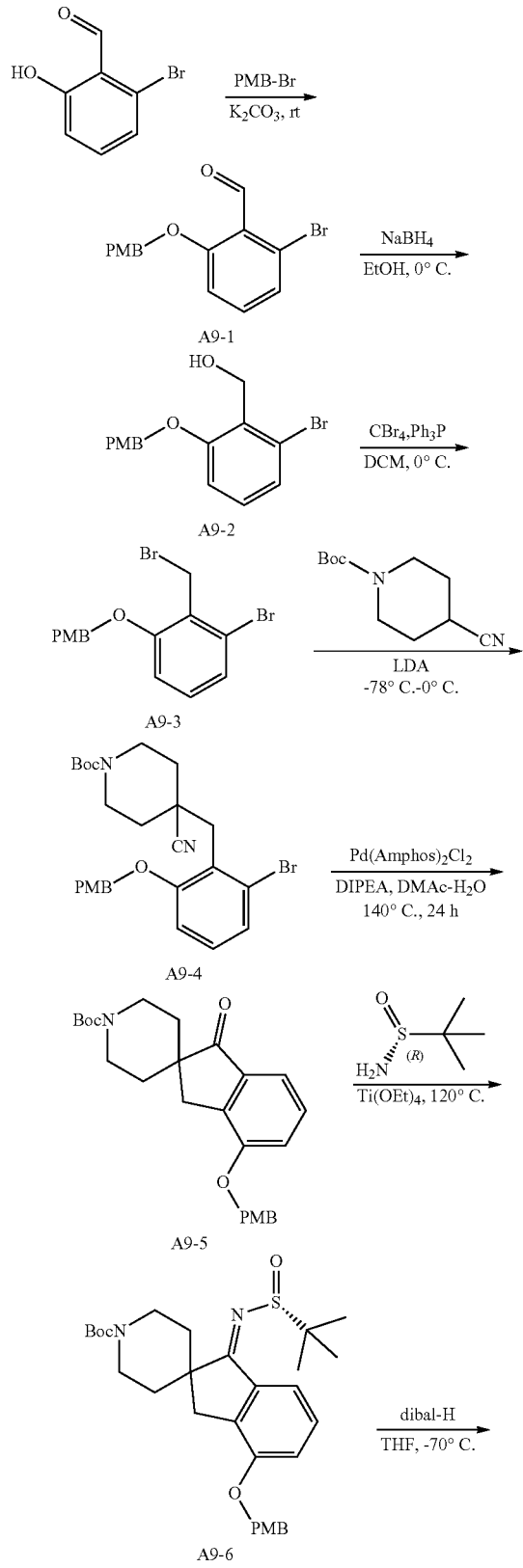

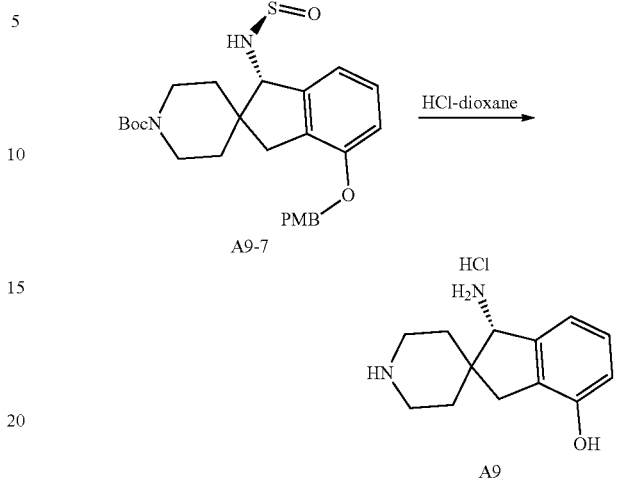

Step 1: 2-bromo-6-hydroxybenzaldehyde (5 g, 24.9 mmol) was dissolved in DMF (100 mL), anhydrous potassium carbonate (6.88 g, 49.8 mmol) and 4-methoxybenzyl bromide (5.26 g, 26.1 mmol) was added, the mixture was reacted at room temperature for 18 hours under nitrogen protection, and then the reaction was completed. The reaction solution was poured into ice water, and extracted with ethyl acetate (250 mL) twice. The organic phases were combined and washed with saturated brine. The organic phase was separated, dried over anhydrous sodium sulfate, filtered and concentrated. The crude product was purified by silica gel chromatography to obtain 2-bromo-6-((4-methoxybenzyl)oxy)benzaldehyde (A9-1, 8 g, yield 100%) as a light yellow solid. LCMS: m/z 343.0 [M+Na]+

Step 2: 2-bromo-6-((4-methoxybenzyl)oxy)benzaldehyde (A9-1, 8 g, 24.9 mmol) was dissolved in ethanol (100 mL) and the mixture was cooled to 0° C. in an ice bath. Sodium borohydride (942 mg, 24.9 mmol) was carefully added in multiple batches. The mixture was reacted at 0° C. for 0.5 hours, and then the reaction was completed. The reaction solution was poured into ice water and extracted twice with ethyl acetate (200 mL). The organic phases were combined, washed with saturated brine, dried over anhydrous sodium sulfate, filtered and concentrated to obtain (2-bromo-6-((4-methoxybenzyl)oxy)phenyl)methanol (A9-2, 7.3 g, yield: 90%) as a solid. LCMS: m/z 345.0 [M+Na]+

Step 3: (2-bromo-6-((4-methoxybenzyl)oxy)phenyl)methanol (A9-2, 7.3 g, 22.6 mmol) was dissolved in dichloromethane (200 mL), and the mixture was cooled in an ice bath to 0° C. Carbon tetrabromide (11.2 g, 33.9 mmol) and triphenylphosphine (8.88 g, 33.9 mmol) were added under nitrogen protection. The mixture was reacted at 0° C. for 5 hours, and then the reaction was completed. The reaction solution was poured into ice water and extracted twice with ethyl acetate (200 mL). The organic phases were combined, washed with saturated brine, dried over anhydrous sodium sulfate, filtered and concentrated. The crude product was purified by silica gel chromatography to obtain 1-bromo-2-(bromomethyl)-3-((4-methoxybenzyl)oxy)benzene (A9-3, 4 g, yield: 46%) as a solid. 1H NMR (400 MHz, CDCl3) δ 7.40 (t, J=4.4 Hz, 2H), 7.17-7.20 (m, 1H), 7.11 (t, J=8.2 Hz, 1H), 6.92-6.95 (m, 2H), 6.87-6.89 (m, 1H), 5.30 (s, 2H), 4.76 (s, 2H), 3.83 (s, 3H);

Step 4: 4-cyanopiperidine-1-carboxylic acid tert-butyl ester (2.6 g, 12.4 mmol) was dissolved in anhydrous THF (60 mL) and the mixture was cooled to −78° C. 2M of LDA (7.5 mL, 14.9 mmol) was slowly added dropwise. The mixture was reacted at −78° C. for 0.5 hours, and then a solution of 1-bromo-2-(bromomethyl)-3-((4-methoxybenzyl)oxy)benzene (A9-3, 4 g, 10.4 mmol) in anhydrous THF (40 mL) was added dropwise. The mixture was reacted at −78° C. for 2 hours and then slowly heated to 0° C. The reaction was complete. The reaction solution was poured into ice water and extracted twice with ethyl acetate (200 mL). The organic phases were combined, washed with saturated brine, dried over anhydrous sodium sulfate, filtered and concentrated. The crude product was purified by silica gel chromatography to obtain 4-(2-bromo-6-((4-methoxybenzyl)oxy)benzyl)-4-cyanopiperidine-1-carboxylic acid tert-butyl ester (A9-4, 2.8 g, yield: 44%) as a solid. LCMS: m/z 537.0 [M+Na]$^+$ Step 5: 4-(2-bromo-6-((4-methoxybenzyl)oxy)benzyl)-4-cyanopiperidine-1-carboxylic acid tert-butyl ester (A9-4, 2.6 g, 5.0 mmol) was dissolved in DMAc (100 mL), H$_2$O (10 mL), DIPEA (3.225 g, 25.0 mmol) and PdCl$_2$(AmPhos)$_2$ (354 mg, 0.5 mmol) were added. The mixture was reacted at 130° C. under argon protection for 18 hours, and then the reaction was completed. After cooled to room temperature, the reaction solution was poured into ice water and extracted twice with ethyl acetate (300 mL). The organic phases were combined, washed once with water and saturated brine, dried over anhydrous sodium sulfate, filtered and concentrated. The crude product was purified by silica gel chromatography to obtain 4-((4-methoxybenzyl)oxy)-1-oxo-1,3-dihydrospiro[indene-2,4'-piperidine]-1'-carboxylic acid tert-butyl ester (A9-5, 1.8 g, yield: 82%) as a solid. LCMS: m/z 382.2 [M−56]$^+$ Step 6: 4-((4-methoxybenzyl)oxy)-1-oxo-1,3-dihydrospiro[indene-2,4'-piperidine]-1'-carboxylic acid tert-butyl ester (A9-5, 1.8 g, 4.12 mmol) was dissolved in THF (20 mL), (R)-2-methylpropane-2-sulfinamide (748 mg, 6.18 mmol) and tetraethyl titanate (50 mL) were added. The reaction mixture was heated to 100° C. and refluxed for 18 hours under nitrogen protection. The reaction was completed, and after the mixture was cooled to room temperature, ethyl acetate (200 mL) was added for dilution, saturated brine (50 mL) was added, and white solid precipitated. The mixture was filtered and the filter cake was washed with ethyl acetate. The filtrate was washed with saturated brine, and the organic phase was separated, dried over anhydrous sodium sulfate, filtered, and concentrated. The crude product was purified by silica gel chromatography to obtain (R,Z)-1-((tert-butylsulfinyl)imino)-4-((4-methoxybenzyl)oxy)-1,3-dihydrospiro[indene-2,4'-piperidine]-1'-carboxylic acid tert-butyl ester (A9-6, 1.7 g, yield: 76%) as a white solid. LCMS: m/z 541.3 [M+H]$^+$ Step 7: (R,Z)-1-((tert-butylsulfinyl)imino)-4-((4-methoxybenzyl)oxy)-1,3-dihydrospiro[indene-2,4'-piperidine]-1'-carboxylic acid tert-butyl ester (A9-6, 1.7 g, 3.15 mmol) was dissolved in THF (100 mL) and the mixture was cooled to −78° C. under nitrogen protection. 1.5M of DIBAL-H (3.15 mL, 4.7 mmol) was slowly added dropwise to the reaction solution. After the addition was completed, the reaction solution was reacted at −78° C. for 1 hour until the reaction was completed. Water was added to quench the reaction, saturated potassium sodium tartrate solution (50 mL) was added, the mixture was extracted with ethyl acetate (200 mL×2), and the organic phase was washed once with saturated sodium chloride aqueous solution. The organic phase was separated, dried over anhydrous sodium sulfate, filtered and concentrate. The crude product was purified by silica gel chromatography to obtain (S)-1-(((R)-tert-butylsulfinyl)amino)-4-((4-methoxybenzyl)oxy)-1,3-dihydrospiro[indene-2,4'-piperidine]-1'-carboxylic acid tert-butyl ester (A9-7, 1.5 g, yield: 88%) as a white solid. LCMS: m/z 543.3 [M+H]$^+$ Step 8: (S)-1-(((R)-tert-butylsulfinyl)amino)-4-((4-methoxybenzyl)oxy)-1,3-dihydrospiro[indene-2,4'-piperidine]-1'-carboxylic acid tert-butyl ester (A9-7, 1.5 g, 2.77 mmol) was dissolved in MeOH (50 mL), the mixture was cooled to 0° C., and 4 M of hydrochloric acid dioxane solution (10 mL, 40 mmol) was added dropwise. The mixture was reacted at room temperature for 3 hours, and then the reaction is completed. The reaction solution was concentrated to obtain (S)-1-amino-1,3-dihydrospiro[indene-2,4'-piperidin]-4-ol hydrochloride (A9, 600 mg, yield: 85%) as a white solid. LCMS: m/z 219.2 [M+H]$^+$ Intermediate A10: (S)-1-(((R)-tert-butylsulfinyl)amino)-4-cyano-1,3-dihydrospiro[indene-2,4'-piperidine]

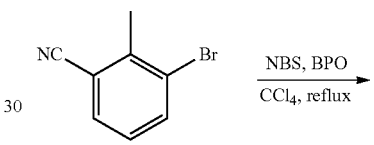

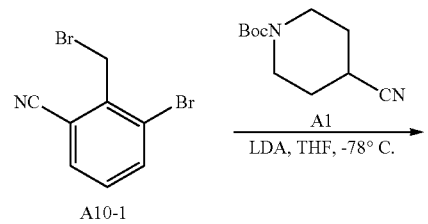

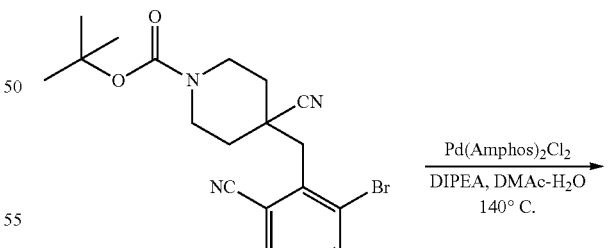

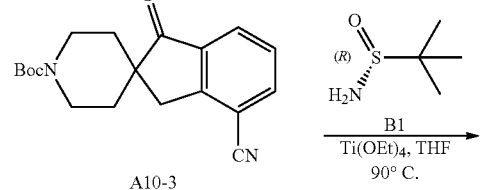

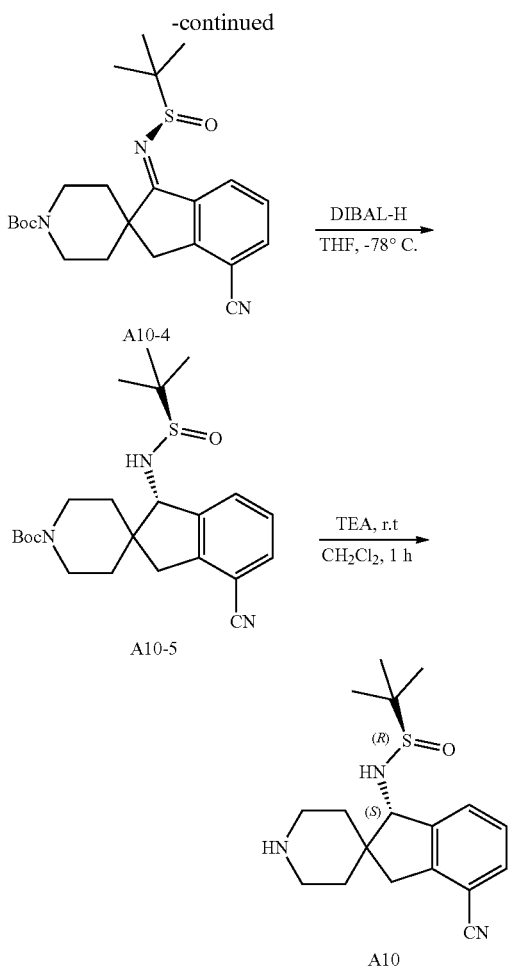

Step 1: 2-methyl-3-cyanobromobenzene (3.0 g, 15.3 mmol, 1.0 eq), N-bromosuccinimide (2.72 g, 15.3 mmol, 1.0 eq), dibenzoyl peroxide (371 mg, 1.53 mmol, 0.1 eq) and carbon tetrachloride (40 mL) was successively added to a 100 mL round-bottom flask, and the mixture was stirred at 80° C. for 16 hours. The reaction solution was concentrated under reduced pressure to obtain a residue. The residue was dissolved in ethyl acetate (200 mL), washed twice with 2N of NaOH aqueous solution (50 mL) and once with saturated brine (50 mL), dried over anhydrous sodium sulfate, and filtered. The filtrate was concentrated under reduced pressure to obtain a crude product. The crude product was purified by silica gel chromatography to obtain 1-bromo-2-(bromomethyl)-3-cyanobenzene (A10-1, 2.0 g, yield: 47.5%) as a white solid.

Step 2: Tetrahydrofuran (30 mL) and 4-cyanopiperidine-1-carboxylic acid tert-butyl ester (1.84 g, 8.73 mmol, 1.2 eq) were successively added to a 100 mL round-bottom flask, the mixture was cooled to −78° C., then 2.0 M of LDA (5.1 mL, 10.2 mmol, 1.4 eq) was added, and the mixture was stirred at −78° C. for one hour. Then, a solution of 1-bromo-2-(bromomethyl)-3-cyanobenzene (A10-1, 2.0 g, 7.27 mmol, 1.0 eq) in tetrahydrofuran (15 mL) was added, and the mixture was stirred at −78° C. for 0.5 hours. Then, the low temperature bath was removed, the mixture was allowed to return to room temperature and then continued to be stirred for one hour. After the raw material was confirmed to be reacted completed by TLC, saturated brine (30 mL) was added to quench, and then the mixture was extracted with ethyl acetate (100 mL*2). The combined organic phase was washed with saturated brine (50 mL), dried over anhydrous sodium sulfate, and filtered. The filtrate was concentrated under reduced pressure to obtain a crude product. The crude product was purified by silica gel chromatography to obtain tert-butyl-4-(2-bromo-6-cyanobenzyl)-4-cyanopiperidine-1-carboxylate (A10-2, 1.5 g, yield: 51%) as a light yellow oily matter. LC-MS: m/z 404.1, 406.1 [M+H]$^+$.

Step 3: Tert-butyl-4-(2-bromo-6-cyanobenzyl)-4-cyanopiperidine-1-carboxylate (A10-2, 1.5 g, 3.71 mmol, 1.0 eq), Pd(AmPhos)$_2$Cl$_2$ (262 mg, 0.37 mmol. 0.1 eq), diisopropylethylamine (2.4 g, 18.5 mmol, 5.0 eq), N,N-dimethyl acetamide (30 mL) and water (4 mL) were successively added to a dry 100 mL round-bottom three-necked flask. With stirring, the atmosphere in the reaction system was replaced with nitrogen three times, and then the reaction mixture was heated to 140° C. and reacted for 16 hours. After the reaction was completed, the reaction solution was cooled to room temperature, diluted with ethyl acetate (100 mL) and filtered under reduced pressure. The filter cake was washed with ethyl acetate (20 mL), and the resulting filtrate was washed with saturated brine (30 mL) 3 times, dried over anhydrous sodium sulfate and filtered. The filtrate was concentrated under reduced pressure to obtain a crude product. The crude product was purified by silica gel chromatography to obtain tert-butyl-4-cyano-1-oxo-1,3-dihydrospiro[indene-2,4'-piperidine]-1-formate (A10-3, 0.90 g, yield: 74.3%) as a white solid. LC-MS: m/z 327.2 [M+H]$^+$.

Step 4: Tert-butyl-4-cyano-1-oxo-1,3-dihydrospiro[indene-2,4'-piperidine]-1-formate (A10-3, 900 mg, 2.76 mmol), titanium tetraethoxylate (3.78 g, 16.6 mmol), (R)-(+)-tert-butylsulfinamide (401 mg, 3.3 mmol) and tetrahydrofuran (20 mL) were successively added to a dry 100 mL single-necked flask, and the mixture was stirred under heating and reflux for 16 hours. After cooling to room temperature, saturated brine (60 mL) was added to the reaction residue, and then the resulting mixture was stirred for 15 minutes and then filtered through diatomite. The aqueous mixture was extracted with ethyl acetate (3×80 mL). The organic phase was dried over anhydrous sodium sulfate, filtered, and concentrated under reduced pressure. The resulting residue was purified by silica gel chromatography (0 to 30% gradient of ethyl acetate:petroleum ether) to obtain (R,Z)-1-((tert-butylsulfinyl)imide)-4-cyano-1,3-dihydrospiro[indene-2,4'-piperidine]-1'-carboxylic acid tert-butyl ester (A10-4, 980 mg, yield: 82.7%) as a white solid. LCMS: m/z 430.2 [M+H]$^+$.

Step 5: Tetrahydrofuran (15 mL) and (R,Z)-1-((tert-butylsulfinyl)imide)-4-cyano-1,3-dihydrospiro[indene-2,4'-piperidine]-1'-carboxylic acid tert-butyl ester (A10-4, 980 mg, 2.28 mmol, 1.0 eq) was successively added to a dry 50 mL three-necked flask. Diisobutyl aluminum hydride (6.8 ml, 1.5 M in toluene, 10.3 mmol, 4.5 eq) was added dropwise at −78 $^O$C and under nitrogen protection, and the mixture continued to be stirred for half an hour. Then the mixture was heated to 0° C. and continued to be stirred for half an hour. After the reaction was completed, the reaction mixture was quenched with potassium sodium tartrate (4 g dissolved in 20 mL of water), stirred for half an hour, and extracted with ethyl acetate (30 mL*3). The obtained organic phase was washed with saturated brine (30 mL), dried with anhydrous sodium sulfate, filtered, and concentrated under reduced pressure. The residue was purified by silica gel chromatography (0-70% gradient of ethyl acetate:petroleum ether) to obtain (S)-1-((R)-tert-butyl sulfinyl)amino)-4-cyano-1,3-dihydrospiro[indene-2,4'-piperidine]-1'-carboxylic acid tert-butyl ester (A10-5, 800 mg, yield: 81.3%) as a yellow solid. LC-MS: m/z 432.2 [M+H]⁺.

Step 6: (S)-1-((R)-tert-butylsulfinyl)amino)-4-cyano-1,3-dihydrospiro[indene-2,4'-piperidine]-1'-carboxylic acid tert-butyl ester (A10-5, 800 mg, 1.85 mmol), dichloromethane (15 mL), and trifluoroacetic acid (5 mL) was successively added to a dry 50 mL single flask, and the resulting mixture was stirred at room temperature for 1 hour. Na$_2$CO$_3$ saturated aqueous solution was added until pH=7, and the aqueous mixture was extracted with dichloromethane (3×50 mL). The combined organic phase was washed with saline solution, dried over anhydrous sodium sulfate, filtered and concentrated under reduced pressure. The residue was purified by silica gel chromatography (0-70% gradient of ethyl acetate:petroleum ether) to obtain (R)—N—((S)-4-cyano-1,3-dihydrospiro[indene-2,4'-piperidine]-1-yl)-2-methylpropyl-2-sulfinamide (A10, 490 mg, yield: 79.8%) as a yellow solid. LCMS: m/z 332.2 [M+H]⁺.

Intermediate A11: (S)-5,7-dihydrospiro[cyclopenta[b]pyridine-6,4'-piperidine]-5-amine

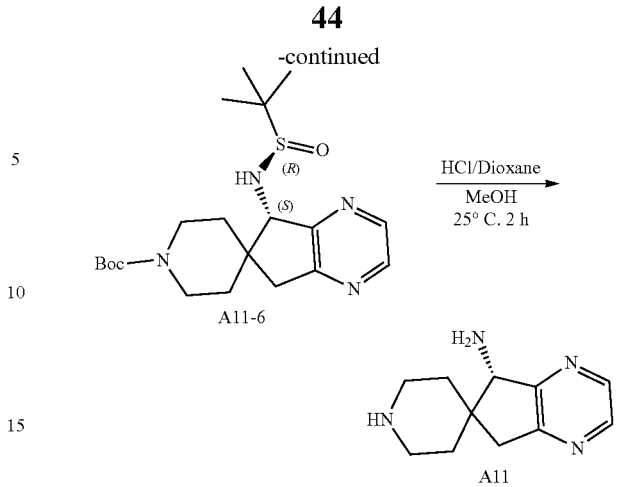

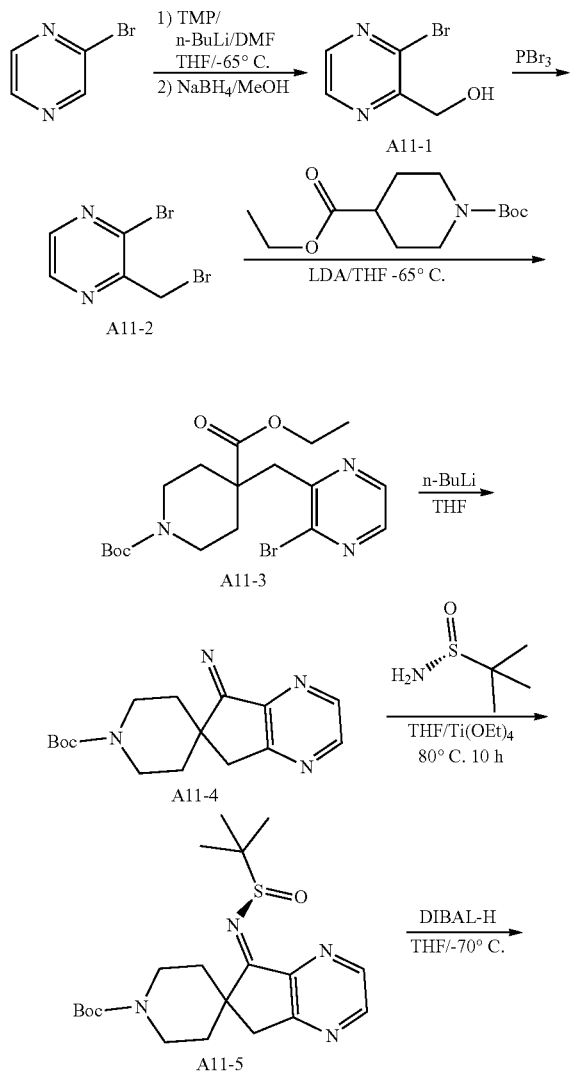

Step 1: 2,2,6,6-tetramethylpiperidine (5.33 g, 37.8 mmol) was dissolved in 100 mL of tetrahydrofuran, the mixture was cooled to −65° C. under argon protection in a dry ice acetone bath, n-butyl lithium (2.5M, 15.8 mL, 39.5 mmol) was added dropwise, then the temperature of the mixture was maintained at 0° C. for 30 min and then lowed to −65° C. again, a mixture of 2-bromopyrazine (5.0 g, 31.4 mmol) and 10 mL of tetrahydrofuran was added dropwise, the temperature was maintained for 30 min, a mixture of DMF (5.75 g, 78.6 mmol) and 10 mL of tetrahydrofuran was added dropwise, the resulting mixture continued to be stirred for 2 hours, and then the reaction was complete. Then, 75 mL of methanol was added dropwise at −65° C., the mixture was stirred for 10 minutes, NaBH$_4$ (2.38 g, 62.9 mmol) was slowly added, the temperature of the mixture was slowly raised to 0° C. and maintained for 1 hour, and then the reaction was completed. The reaction liquid was poured into 500 mL of ice NH$_4$Cl aqueous solution, and extracted with ethyl acetate for three times. The organic phase was washed once with saturated brine. The organic phases were combined, dried over anhydrous sodium sulfate, filtered, concentrated and passed through the column to obtain (3-bromopyridin-2-yl)methanol (A11-1, 4.33 g, yield: 72.9%) as a yellow solid. LCMS: m/z 191 [M+H]⁺

Step 2: (3-bromopyridin-2-yl)methanol (A11-1, 4.33 g, 22.9 mmol) was dissolved in 80 mL of ether, PBr$_3$ (6.83 g, 25.2 mmol) was added dropwise at 0° C. under the protection of nitrogen, then the mixture was heated to reflux at about 40° C. and reacted for 4 hours, and then the reaction was completed. The reaction liquid was poured into an ice NaHCO$_3$ aqueous solution, extracted twice with dichloromethane, and washed once with saturated brine. The organic phases were combined, dried over anhydrous sodium sulfate, filtered, concentrated, and passed thorough the column to obtain 2-bromo-3-(bromomethyl)pyrazine (A11-2, 5.14 g, yield: 89.0%) as a near colorless transparent oily matter. LCMS: m/z 252.9 [M+H]⁺

Step 3: N-Boc-4-piperidine ethyl formate (6.81 g, 26.5 mmol) was dissolved in 160 mL of anhydrous tetrahydrofuran, the mixture was cooled to −65° C. in a dry ice acetone bath under the protection of argon, LDA (2.0 M, 16.8 mL, 33.6 mmol) was slowly added dropwise, and the mixture was reacted for 1 hour while the temperature was maintained. A solution of 2-bromo-3-(bromomethyl)pyrazine (A11-2, 5.14 g, 24.1 mmol) in anhydrous tetrahydrofuran (30 mL) was added dropwise at −65° C., the reaction continued for 2 hours while the temperature was maintained, and then the reaction was completed. The reaction solution was poured into 300 mL of ice NH₄Cl aqueous solution, and extracted with ethyl acetate for three times. The organic phase was washed with saturated brine for one time. The organic phases were combined, dried over anhydrous sodium sulfate, filtered, concentrated and passed through the column to obtain 1-(tert-butyl)-4-ethyl-4-((3-bromopyrazin-2-yl)methyl)piperidine-1,4-dicarboxylate (A11-3, 5.81 g, yield: 56.4%). LCMS: m/z 328.1 [M+H−100]⁺

Step 4: 1-(tert-butyl)-4-ethyl-4-((3-bromopyrazin-2-yl)methyl)piperidine-1,4-dicarboxylate (A11-3, 5.8 g, 13.5 mmol) was dissolved in 300 mL of tetrahydrofuran, the mixture was cooled to −65° C. in a dry ice acetone bath under the protection of argon, n-butyl lithium (2.5M, 8.2 ml, 20.3 mmol) was added dropwise, the mixture was naturally warmed up to −10° C. and maintained for 3 hours, and then the reaction was complete. The reaction liquid was poured into 300 mL of ice NH₄Cl aqueous solution, and extracted with ethyl acetate for three times. The organic phase was washed with saturated brine once. The organic phases were combined, dried over anhydrous sodium sulfate, filtered, concentrated, and passed through the column to obtain 5-oxo-5,7-dihydrospiro[cyclopenta[b]pyrazine-6,4'-piperidine]-1'-carboxylic acid tert-butyl ester (A11-4, 2.23 g, yield: 54.4%) as a yellow solid.

LCMS: m/z 304.2 [M+H]⁺ weak

Step 5: 5-oxo-5,7-dihydrospiro[cyclopenta[b]pyrazine-6,4'-piperidine]-1'-carboxylic acid tert-butyl ester (A11-4, 2.23 g, 7.35 mmol) was dissolved in 350 mL tetrahydrofuran, and (R)-2-methylpropane-2-sulfinamide (980 mg, 8.09 mmol) and tetraethyl titanate (21.8 g, 95.6 mmol) were added. Under nitrogen protection, the mixture was heated to 80° C. and refluxed for 10 hours. The reaction was completed. The reaction mixture was cooled to room temperature, poured into 400 mL of ice water, and extracted with 300 mL of ethyl acetate for 3 times (the aqueous phase contained a large amount of white flocculent solid, and the organic phase was almost without solid). The organic phase was washed once with 200 mL of water and once with 200 mL of saturated brine. The organic phases was combined, dried over anhydrous sodium sulfate, filtered, concentrated, and passed through the column to obtain (R,Z)-5-((tert-butylsulfinyl)imino)-5,7-dihydrospiro[cyclopenta[b]pyrazine-6,4'-piperidine]-1'-carboxylic acid tert-butyl ester (A11-5, 2.38 g, yield: 79.6%) as a light orange foamed solid. LCMS: m/z 407.1 [M+H]⁺

Step 6: (R,Z)-5-((tert-butylsulfinyl)imino)-5,7-dihydrospiro[cyclopenta[b]pyrazine-6,4'-piperidine]-1'-carboxylic acid tert-butyl ester (A11-5, 2.38 g, 5.85 mmol) was dissolved in 280 mL of tetrahydrofuran, and the mixture was cooled to −65° C. in a dry ice acetone bath under the protection of argon. 1.5M of DIBAL-H (5.07 mL, 7.61 mmol) was slowly added dropwise, and the temperature of the mixture continued to be maintained for 2 hours, and then the reaction is completed. The reaction solution was poured into 300 mL of saturated potassium sodium tartrate aqueous solution, extracted with ethyl acetate for 3 times. The organic phases were combined, dried over sodium sulfate, filtered and concentrated to dry to obtain (S)-5-((R)-tert-butylsulfinyl)amino)-5,7-dihydrospiro[cyclopenta[b]pyrazine-6,4'-piperidine]-1'-carboxylic acid tert-butyl ester crude product (A11-6, 2.48 g) as a golden yellow foamed solid. LCMS: m/z 309.3 [M+H−100]⁺

Step 7: (S)-5-((R)-tert-butylsulfinyl)amino)-5,7-dihydrospiro[cyclopenta[b]pyrazine-6,4'-piperidine]-1'-carboxylic acid tert-butyl ester crude product (A11-6, 2.48 g, 5.85 mmol) was dissolved in 120 mL of methanol, the mixture was cooled in ice water to about 0° C. under the protection of argon, 4 M of dioxane hydrochloride solution (18 mL, 72 mmol) was added dropwise, the mixture was reacted at room temperature for 2 hours, and then the reaction was completed. The reaction solution was concentrated to dry, anhydrous acetonitrile was added for pulping, and the mixture was filtered under the protection of argon to obtain (S)-5,7-dihydrospiro[cyclopenta[b]pyrazine-6,4'-piperidine]-5-amine hydrochloride (A11, 1.77 g, yield: 99%) as a dark green solid powder (very easy to absorb moisture and become dark green oil drop), which was preserved under argon protection. LCMS: m/z 205.3 [M+H]⁺

Intermediate A12: (S)-1-(((R)-tert-butylsulfinyl)amino)-4-methoxy-1,3-dihydrospiro[indene-2,4'-piperidine]

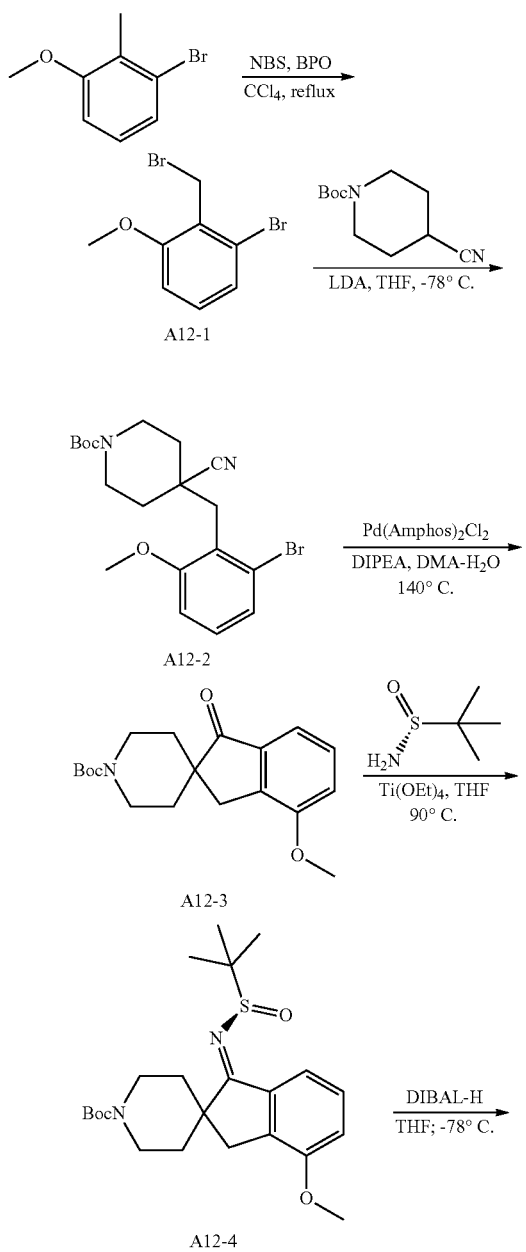

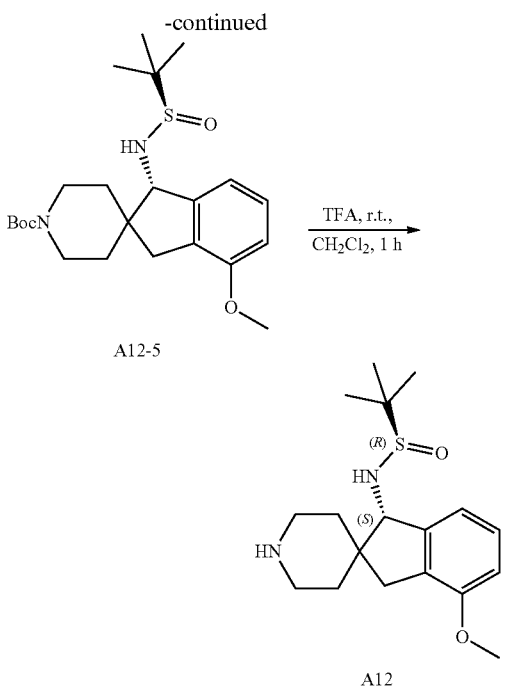

Step 1: 2-methyl-3-methoxybromobenzene (2.0 g, 9.95 mmol, 1.0 eq), N-bromosuccinimide (1.77 g, 9.95 mmol, 1.0 eq), dibenzoyl peroxide (241 mg, 0.995 mmol, 0.1 eq) and carbon tetrachloride (40 mL) was added into a 100 mL round-bottom flask successively, the mixture was stirred at 80° C. for 16 hours, and the reaction solution is concentrated under reduced pressure to obtain a residue. The residue was dissolved in ethyl acetate (200 mL), washed twice with 2N of NaOH aqueous solution (50 ml*2) and once with saturated brine (50 mL), dried over anhydrous sodium sulfate and filtered. The filtrate was concentrated under reduced pressure to obtain a crude product. The crude product was purified by silica gel chromatography to obtain 1-bromo-2-(bromomethyl)-3-methoxybenzene (A12-1, 2.0 g, yield: 71.8%) as a white solid.

Step 2: Tetrahydrofuran (30 mL) and N-Boc-4-cyanopyridine (1.8 g, 8.57 mmol, 1.2 eq) were added to a 100 mL round-bottom flask successively, the mixture was cooled to −78° C., then 2.0 M of LDA (5 mL, 10 mmol, 1.4 eq) was added and the mixture was stirred at −78° C. for one hour. Then a solution of 1-bromo-2-(bromomethyl)-3-methoxybenzene (A12-1, 2.0 g, 7.14 mmol, 1.0 eq) in tetrahydrofuran (15 mL) was added and the mixture was stirred at −78° C. for 0.5 h. Then the low temperature bath was removed. The mixture was allowed to warm to room temperature naturally, and continued to be stirred for one hour. After the raw materials were confirmed to be reacted completely by TLC, saturated brine (30 mL) was added to quench the reaction, and then the mixture was extracted with ethyl acetate (100 mL*2). The combined organic phase was washed with saturated brine (50 mL), dried over anhydrous sodium sulfate and filtered. The filtrate was concentrated under reduced pressure to obtain a crude product. The crude product was purified by silica gel chromatography to obtain N-Boc-4-(2-bromo-6-methoxybenzyl)-4-cyanopyridine (A12-2, 1.5 g, yield: 51.3%) as a light yellow oily matter. LCMS: m/z 409.1, 411.1 [M+H]⁺.

Step 3: N-Boc-4-(2-bromo-6-methoxybenzyl)-4-cyanopyridine (A12-2, 1.5 g, 3.66 mmol, 1.0 eq), Pd (AmPhos)$_2$Cl$_2$ (259 mg, 0.37 mmol, 0.1 eq), diisopropylethylamine (2.37 g, 18.3 mmol, 5.0 eq), N,N-dimethylacetamide (30 mL) and water (4 mL) were added to a dry 100 mL round-bottom flask successively. Under stirring, the atmosphere in the reaction system was replaced with nitrogen three times, and then the reaction mixture was heated to 140° C. and reacted for 16 hours. After the reaction was completed, the reaction liquid is cooled to room temperature, diluted with ethyl acetate (100 mL) and filtered under reduced pressure. The filter cake was washed with ethyl acetate (20 mL). The obtained filtrate was washed with saturated brine (30 ml*3) for three times, dried over anhydrous sodium sulfate and filtered. The filtrate was concentrated under reduced pressure to obtain a crude product. The crude product was purified by silica gel chromatography to obtain N-Boc-4-methoxy-1-oxo-1,3-dihydrospiro[indene-2,4'-piperidine] (A12-3, 0.90 g, yield: 74.1%) as a white solid.
LC-MS: m/z 332.2 [M+H]⁺.

Step 4: N-Boc-4-methoxy-1-oxo-1,3-dihydrospiro[indene-2,4'-piperidine] (A12-3, 900 mg, 2.72 mmol), tetraethoxy titanium (3.72 g, 16.3 mmol), (R)-(+)-tert-butylsulfinamide (395 mg, 3.26 mmol) and tetrahydrofuran (20 mL) were added to a dry 100 mL single-necked flask successively, and the mixture was stirred for 16 hours under heating and reflux. After the reaction mixture was cooled to room temperature, saturated brine (60 mL) was added to the reaction residue, and then the resulting mixture was stirred for 15 minutes and filtered through diatomite. The aqueous mixture was extracted with ethyl acetate (3×80 mL). The organic phase was dried over anhydrous sodium sulfate, filtered and concentrated under reduced pressure. The obtained residue was purified by silica gel chromatography (0-30% gradient of ethyl acetate:petroleum ether) to obtain N-Boc-(R,Z)-1-((tert-butylsulfinyl)imide)-4-methoxy-1,3-dihydrospiro[indene-2,4'-piperidine] (A12-4, 800 mg, yield: 67.8%) as a white solid.
LC-MS: m/z 435.2 [M+H]⁺.

Step 5: Tetrahydrofuran (15 mL) and N-Boc-(R,Z)-1-((tert-butylsulfinyl)imide)-4-methoxy-1,3-dihydrospiro[indene-2,4'-piperidine] (A12-4, 800 mg, 1.84 mmol, 1.0 eq) were added to a dry 50 mL three-necked flask successively. Diisobutyl aluminum hydride (5.52 ml, 1.5M in toluene, 8.28 mmol, 4.5 eq) was added dropwise at −78° C. under nitrogen protection, and the mixture continued to stirred for half an hour. Then the mixture was heated to 0° C. and continued to be stirred for half an hour. After the reaction was completed, the reaction mixture was quenched with potassium sodium tartrate (4 g dissolved in 20 mL of water), stirred for half an hour, and extracted with ethyl acetate (30 mL*3). The obtained organic phase was washed with saturated brine (30 mL), dried over anhydrous sodium sulfate, filtered, and concentrated under reduced pressure. The residue is purified by silica gel chromatography (0-70% gradient of ethyl acetate:petroleum ether) to obtain tert-butyl (S)-1-(((R)-tert-butylsulfinyl)amino)-4-methoxy-1,3-dihydrospiro[indene-2,4'-piperidine]-1'-formate (A12-5, 720 mg, yield: 89.6%) as a yellow solid. LCMS: m/z 437.2 [M+H]⁺.

Step 6: Tert-butyl (S)-1-(((R)-tert-butylsulfinyl)amino)-4-methoxy-1,3-dihydrospiro[indene-2,4'-piperidine]-1'-formate (A12-5, 720 mg, 1.65 mmol), dichloromethane (15 mL) and trifluoroacetic acid (5 mL) were added to a dry 50 mL single-necked flask successively, and the resulting mixture was stirred for 1 hour at room temperature. Na$_2$CO$_3$ saturated aqueous solution was added until pH=7, and the aqueous mixture was extracted with dichloromethane (3×50 mL). The combined organic phase was washed with saline water, dried over anhydrous sodium sulfate, filtered and concentrated under reduced pressure. The residue was purified by silica gel chromatography (0-70% gradient of ethyl acetate:petroleum ether) to obtain (R)—N—((S)-4-methoxy-1,3-dihydrospiro[indene-2,4'-piperidin]-1-yl)-2-methylpropyl-2-sulfinamide (A12, 520 mg, yield: 93.7%) as a yellow solid. LCMS: m/z 337.2 [M+H]$^+$.

Intermediate A13: (S)-2-chloro-4,6-dihydrospiro[cyclopenta[d]thiazole-5,4'-piperidine]-4-amine

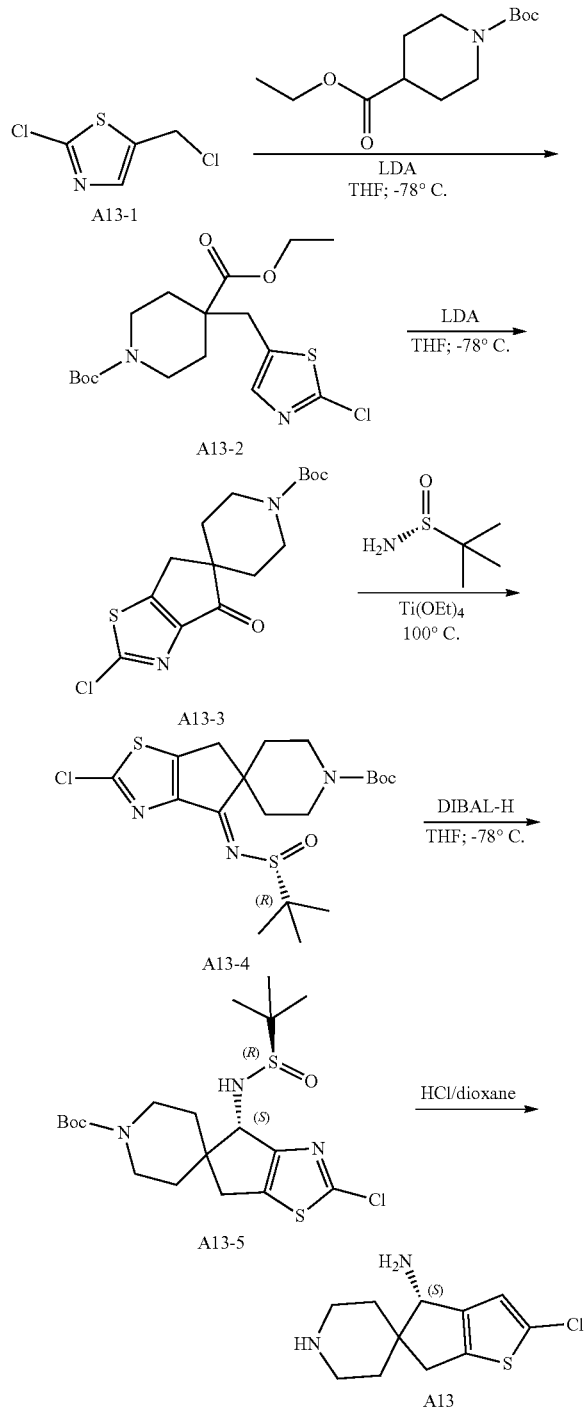

Step 1: 1-tert-butyl 4-ethylpiperidine-1,4-dicarboxylate (10.7 g, 41.6 mmol, 1.2 eq) was dissolved in THF (50 mL), LDA (2M, 9.8 mL, 19.6 mmol, 1.1 eq) was added dropwise at −78° C., the mixture was stirred for 2 h at this temperature, and 2-chloro-5-(chloromethyl)thiazole (A13-1, 3 g, 34.7 mmol, 1.0 eq) dissolved in THF (10 mL) was added dropwise to the system. Then the reaction continued at the temperature for 1.5 h. TLC testing indicated that a little raw material was unreacted. The reaction mixture was quenched with water, extracted with ethyl acetate (100 mL×2). The organic phases were combined and then washed with saturated sodium chloride aqueous solution. The organic phase was separated, then dried over anhydrous sodium sulfate, filtered and concentrated, mixed with silica gel and passed through the column (PE:EA:DCM=4:1:1) to obtain 1-tert-butyl-4-ethyl 4-(2-chlorothiazol-5-yl)methyl)piperidine-1,4-dicarboxylate (A13-2, 2.4 g, yield: 35%) as a yellow oily matter.

Step 2: 1-tert-butyl-4-ethyl 4-(2-chlorothiazol-5-yl)methyl)piperidine-1,4-dicarboxylate (A13-2, 4 g, 10.3 mmol) was dissolved in THF (100 mL), and LDA (2M, 8.5 mL, 16.6 mmol) was added dropwise at −78° C. The mixture was reacted for 1 h, and then the reaction was completed. Saturated amine chloride (100 mL) was added to quench the reaction and the mixture was extracted with ethyl acetate (100 mL×3). The organic phases were combined and washed with saturated sodium chloride aqueous solution. The organic phase was dried over anhydrous sodium sulfate. The filtrate was purified by silica gel chromatography to obtain 2-chloro-4-oxo-4,6-dihydrospiro[cyclopenta[d]thiazole-5,4'-piperidine]-1'-carboxylic acid tert-butyl ester (A13-3, 1.9 g, yield: 54%) as a yellow oily matter. LCMS: m/z 343 [M+H]$^+$ Step 3: 2-chloro-4-oxo-4,6-dihydrospiro[cyclopenta[d]thiazole-5,4'-piperidine]-1'-carboxylic acid tert-butyl ester (A13-3, 710 mg, 2.07 mmol), Ti(OEt)$_4$ and (R)-2-methylpropane-2-sulfinamide (276 mg, 2.28 mmol) were added to a reaction flask, and the mixture was heated to 100° C. under nitrogen protection for 5 h. The reaction was completed. The mixture was cooled to room temperature and diluted with ethyl acetate (50 mL), saturated brine (15 mL) was added, and white solid precipitated out. The mixture was filtered. The filter cake was washed with ethyl acetate. The filtrate was washed with saturated brine. The organic phase was separated and then dried over anhydrous sodium sulfate, filtered and concentrated. The crude product was purified by silica gel chromatography to obtain tert-butyl (E)-4-((tert-butylsulfinyl)imino)-2-chloro-4,6-dihydrospiro[cyclopenta[d]thiazole-5,4'-piperidine]-1'-carboxylic acid tert-butyl ester (A13-4, 600 mg, yield: 68%) as a light yellow solid. LCMS: m/z 426 [M+H]$^+$ Step 4: Tert-butyl (E)-4-((tert-butylsulfinyl)imino)-2-chloro-4,6-dihydrospiro[cyclopenta[d]thiazole-5,4'-piperidine]-1'-carboxylic acid tert-butyl ester (A13-4, 200 mg, 0.47 mmol) was dissolved in THF (10 mL), and the mixture was cooled to −78° C. under nitrogen protection. 1.5M of DIBAL-H (0.5 mL, 0.75 mmol) was slowly added dropwise to the reaction solution, and after the addition of DIBAL-H was completed, the mixture was reacted at −78° C. for 1 hour, and then the reaction was completed. Water was added to quench the reaction, and then saturated potassium sodium tartrate solution (20 mL) was added. The mixture was extracted with ethyl acetate (50 mL×2), and the organic phase was washed with saturated sodium chloride aqueous solution once. The organic phase was separate, dried over anhydrous sodium sulfate, filtered and concentrated. The crude product was purified by silica gel chromatography to obtain tert-butyl (S)-4-(((R)-tert-butylsulfinyl)amino)-2-chloro-4,6-dihydrospiro[cyclopenta[d]thiazole-5,4'-piperidine]-1'-carboxylic acid tert-butyl ester A13-5 (155 mg, yield: 76%) as a light yellow solid. LCMS: m/z 448 [M+H]+

Step 5: Tert-butyl (S)-4-(((R)-tert-butylsulfinyl)amino)-2-chloro-4,6-dihydrospiro[cyclopenta[d]thiazole-5,4'-piperidine]-1'-carboxylic acid tert-butyl ester (A13-5, 155 mg, 0.35 mmol) was dissolved in 4 M of dioxane hydrochloride solution (5 mL, 20 mmol), and the mixture was reacted at room temperature for 3 hours. The reaction was completed. The reaction solution was concentrated to obtain (S)-2-chloro-4,6-dihydrospiro[cyclopenta[d]thiazole-5,4'-piperidine]-4-amine (A13, 145 mg, hydrochloride) as a light yellow oil. LCMS: m/z 244 [M+H]+

Synthesis of Intermediate B2: 5-chloro-8-iodo-[1,2,4]triazolo[4,3-c]pyrimidine

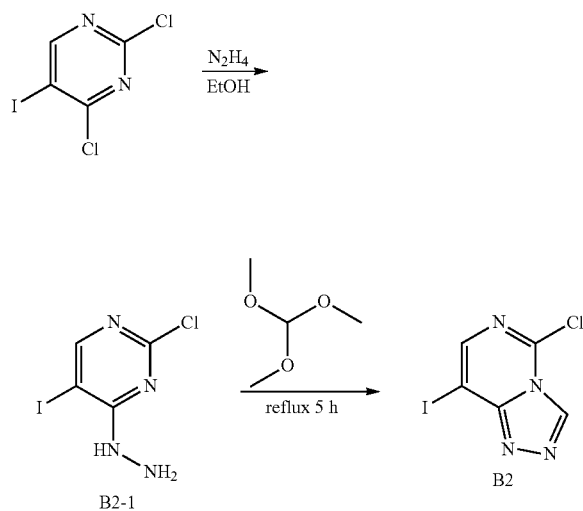

Step 1: 2,4-dichloro-5-iodopyrimidine (1.1 g, 4 mmol) and 20 mL of anhydrous ethanol were added to a dry 100 mL flask. 80% hydrazine hydrate mixture (601 mg, 12 mmol) was slowly added thereto at 0° C. under the protection of nitrogen, and the mixture continued to be stirred for 1 hour. After the reaction was completed, the mixture was filtered and washed with anhydrous ethanol to obtain 2-chloro-4-hydrazino-5-iodopyrimidine (B2-1, 850 mg, yield: 78.7%).

1H NMR (400 MHz, CDCl3) δ8.29 (s, 1H), 6.67 (s, 1H), 4.08 (s, 2H); LCMS: m/z 271.1 [M+H]+.

Step 2: 2-chloro-4-hydrazino-5-iodopyrimidine (810 mg, 3 mmol) and trimethyl orthoformate (10 mL) were added to a dried 100 mL flask successively. Under the protection of nitrogen, the mixture was heated to 85° C. and stirred for 5 hours. After the reaction was completed, the obtained residue was poured into saturated NaCl solution (50 mL), extracted with ethyl acetate (3×30 mL), and washed with saturated brine. The organic layers were combined, dried over anhydrous sodium sulfate, filtered and concentrated under reduced pressure. The obtained residue was purified by silica gel chromatography (0-50% gradient of ethyl acetate/petroleum ether) to obtain 5-chloro-8-iodo-[1,2,4]triazolo[4,3-c]pyrimidine (B2, 420 mg, yield: 50%) as a light yellow solid.

LCMS: m/z 280.9 [M+H]+.

Synthesis of Intermediate B3: 5-chloro-8-iodoimidazo[1,2-c]pyrimidine

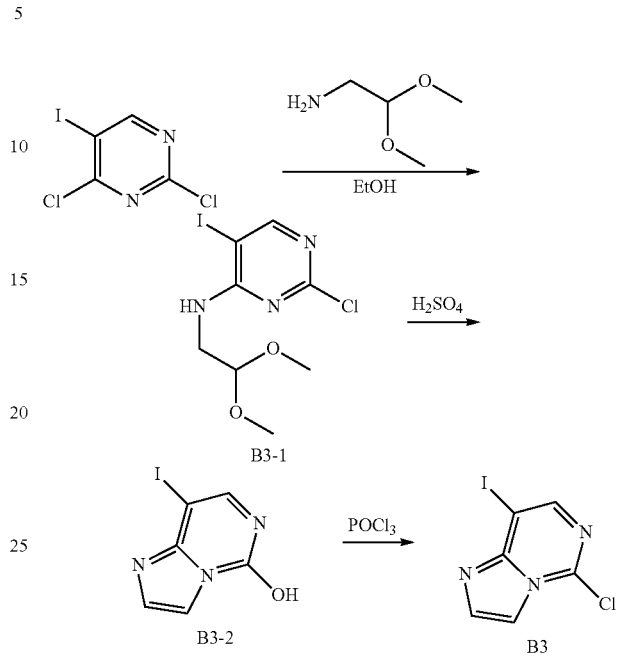

Step 1: 2,4-dichloro-5-iodopyrimidine (1.37 g, 5 mmol), 2,2-dimethoxyethylamine (8.4 g, 10 mmol) and anhydrous ethanol (50 mL) were added to a dry 100 mL flask successively. Then triethylamine (1.01 g, 10 mmol) was slowly added dropwise to the reaction mixture under the protection of nitrogen at 0° C., and then the mixture was stirred at room temperature for 10 hours. After the reaction was completed, the reaction mixture was concentrated in vacuum. 15 mL of water was added to the obtained concentrate, and the mixture was extracted with dichloromethane (3×50 mL) and washed with saturated brine. The organic layers were combined, dried over anhydrous sodium sulfate, filtered and concentrated to obtain 2-chloro-N-(2,2-dimethoxyethyl)-5-iodopyrimidine-4-amine (B3-1, 1.46 g, yield: 85%) as a white solid.

LC-MS: m/z 344.2 [M+H]+.

Step 2: 2-chloro-N-(2,2-dimethoxyethyl)-5-iodopyrimidine-4-amine (B3-1, 1.03 g, 3 mmol) and 10 mL of concentrated sulfuric acid were added to a dried 100 mL flask successively. Under the protection of nitrogen, the mixture was heated to 65° C. and stirred for 2 hours. After the reaction was completed, the reaction liquid was cooled to room temperature. The mixture was slowly poured into ice water, then the pH of the mixture was adjusted to about 6-7 with 4M of NaOH solution, and then the mixture was filtered to obtain 8-iodoimidazo[1,2-c]pyrimidin-5-ol (B3-2, 407 mg, yield: 52%) as a off-white solid. 1H NMR (400 MHz, DMSO-d6) δ 11.81 (s, 1H), 7.93 (d, J=1.4 Hz, 1H), 7.60 (s, 1H), 7.40 (d, J=1.4 Hz, 1H);

LC-MS: m/z 262.2 [M+H]+.

Step 3: 8-iodoimidazo[1,2-c]pyrimidin-5-ol (B3-2, 522 mg, 2 mmol) and phosphorus oxychloride (8 mL) were successively added to a dry 50 mL single-necked flask. Under the protection of nitrogen, N,N-diisopropylethylamine (1 mL) was slowly add dropwise, and then the mixture was heated to 120° C. and stirred for 5 hours. After the reaction was completed, the reaction liquid was cooled to room temperature and concentrated in vacuum, then quenched with saturated sodium bicarbonate solution, extracted with ethyl acetate (3×40 mL), dried over anhydrous sodium sulfate, filtered and concentrated. The obtained residue was purified by silica gel chromatography (0-30% gradient of ethyl acetate:petroleum ether) to obtain 5-chloro-8-iodoimidazo[1,2-c]pyrimidine (B3, 360 mg, yield: 55%) as a light yellow solid.

$^1$H NMR (400 MHz, DMSO-d6) δ 8.24 (s, 1H), 8.20 (d, J=1.4 Hz, 1H), 7.81 (d, J=1.4 Hz, 1H);

LC-MS: m/z 280.1 [M+H]$^+$.

Synthesis of Intermediate C1: sodium 2-amino-3-chloropyridine-4-sulfide

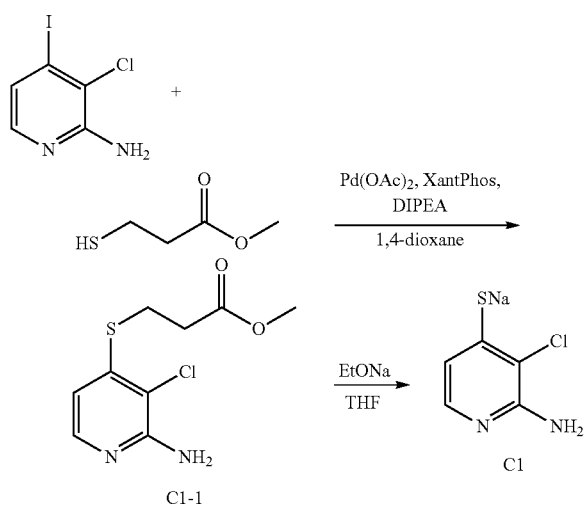

Step 1: 3-chloro-4-iodopyridine-2-amine (2.5 g, 9.82 mmol, 1.0 eq), XantPhos (341 mg, 0.59 mmol. 0.06 eq), palladium acetate (110 mg, 0.49 mmol, 0.05 eq), DIPEA (3.25 ml, 19.6 mmol, 2.0 eq), methyl 3-mercaptopropionate (1.19 ml, 10.8 mmol, 1.1 eq) and 1,4-dioxane (32.5 mL) were added to a dry 100 mL round-bottom three-necked flask successively. Under stirring, the atmosphere in the reaction system was replaced with nitrogen three times, and then the mixture was heated to 100° C. and reacted for 3 hours. After the reaction was completed, the reaction liquid was cooled to room temperature, diluted with ethyl acetate (50 mL) and filtered under reduced pressure, and the filter cake was washed with ethyl acetate (25 mL), The obtained filtrate was concentrated in vacuum, and the obtained residue was purified by silica gel chromatography (0-30% gradient of ethyl acetate:petroleum ether) to obtain methyl 3-((2-amino-3-chloropyridin-4-yl)thio)propionate (C1-1, 2.0 g, yield: 78%) as a yellow solid.

$^1$H NMR (400 MHz, CDCl$_3$) δ 7.89 (d, J=5.4 Hz, 1H), 6.53 (d, J=5.5 Hz, 1H), 4.87 (s, 2H), 3.74 (s, 3H), 3.24 (t, J=7.5 Hz, 2H), 2.75 (t, J=7.5 Hz, 2H).

Step 2: Compound C1-1 (2 g, 8.11 mmol, 1.0 eq) was dissolved in tetrahydrofuran (28 mL) in a dry 100 mL round-bottom three-necked flask, and sodium ethanol (2.9 g, 8.5 mmol, 1.05 eq, 20% wt) was added dropwise to the reaction solution at room temperature under the protection of nitrogen, and then the mixture was stirred for one hour. After the reaction was complete, the mixture was diluted with dichloromethane (60 mL) and treated with ultrasound for 5 min, and then filtered under reduced pressure. The filter cake was dried in vacuum to obtain sodium 2-amino-3-chloropyridine-4-sulfide (C1, 1.4 g, yield: 89%) as a yellow solid.

Synthesis of Intermediate C2: sodium 2,3-dichloropyridine-4-sulfide

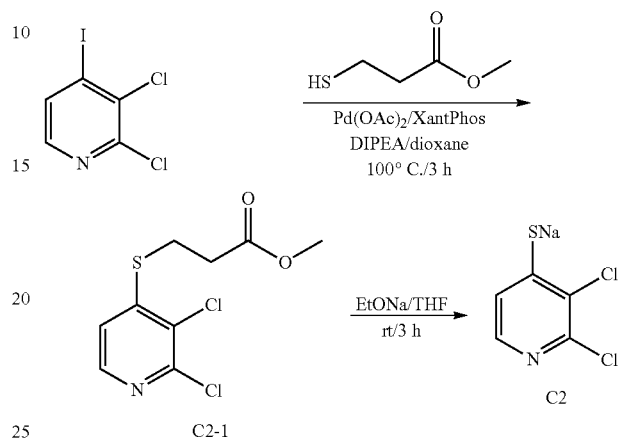

Step 1: 2,3-dichloro-4-iodopyridine (1.0 g, 3.65 mmol, 1.0 eq), methyl 3-mercaptopropionate (480 mg, 4.02 mmol, 1.1 eq) and N,N-diisopropylethylamine (950 mg, 7.3 mmol) were dissolved in 1,4-dioxane (15 mL), the atmosphere in the reaction system was replaced with argon three times, and palladium acetate (82 mg, 0.37 mmol, 0.1 eq) and XantPhos (211 mg, 0.37 mmol, 0.1 eq) were added under the protection of argon. Then the mixture was heated to 100° C. and reacted for 3 hours, and then the reaction was completed. The mixture was extracted with ethyl acetate (100 mL), filtered through diatomite and concentrated. The residue was purified by high performance liquid chromatography to obtain methyl 3-((2,3-dichloropyridin-4-yl)thio)propionate (C2-1, 550 mg, yield: 56.5%) as a off-white solid. LCMS: m/z 266.0 [M+H]$^+$ Step 2: Methyl 3-((2,3-dichloropyridin-4-yl)thio)propionate (C2-1, 100 mg, 0.37 mmol, 1.0 eq) was dissolved in tetrahydrofuran (10 mL) and ethanol (0.5 mL). Sodium alcohol (27 mg, 0.39 mmol, 1.05 eq) was added under the protection of nitrogen, the mixture was reacted at room temperature for 3 hours, the reaction was not completed, sodium alcohol (27 mg, 0.39 mmol, 1.05 eq) was added, the mixture was reacted at room temperature for 3 hours, and then the reaction was completed. Purified water was added and the mixture was freeze-dried to obtain a crude product of sodium 2,3-dichloropyridine-4-sulfide (C21, 50 mg, yield: 100%) as a light yellow solid. LCMS: m/z 180.0 [M+H]$^+$ Synthesis of Intermediate C3: sodium 2-(trifluoromethyl)pyridine-3-sulfide

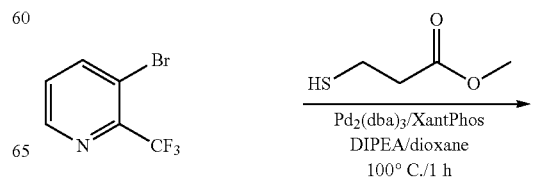

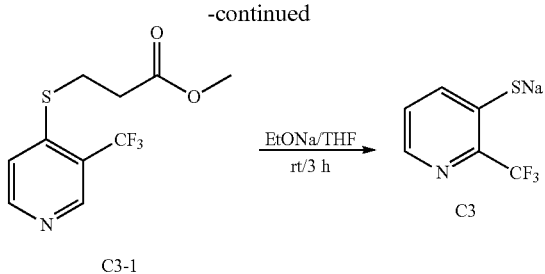

Step 1: 3-bromo-2-trifluoromethylpyridine (400 mg, 1.77 mmol, 1.0 eq), methyl 3-mercaptopropionate (235 mg, 1.95 mmol, 1.1 eq) and N,N-diisopropylethylamine (460 mg, 3.54 mmol, 2.0 eq) was dissolved in 1,4-dioxane (15 mL), the atmosphere in the reaction system was replaced with argon three times, and Pd$_2$(dba)$_3$ (160 mg, 0.18 mmol, 0.1 eq) and XantPhos (205 mg, 0.36 mmol, 0.2 eq) were added under the protection of argon. Then the mixture was heated to 110° C. and reacted for one hour, and the reaction was completed. The mixture was extracted with ethyl acetate (100 mL), filtered through diatomite, concentrated and passed through column (PE:EA=8/1~6/1) to obtain methyl 3-((2-(trifluoromethyl)pyridin-3-yl)thio)propionate (C3-1, 450 mg, yield: 95.7%) as a light yellow oily matter. LCMS: m/z 266.1 [M+H]$^+$ Step 2: Methyl 3-((2-(trifluoromethyl)pyridin-3-yl)thio)propionate (C3-1, 300 mg, 1.13 mmol, 1.0 eq) was dissolved in tetrahydrofuran (10 mL) and ethanol (0.5 mL). Sodium alcohol (84 mg, 1.23 mmol, 1.1 eq) was added under the protection of nitrogen, the mixture was reacted at room temperature for 3 hours, the reaction was not completed, sodium alcohol (83 mg, 1.23 mmol, 1.1 eq) was added, the mixture was reacted at room temperature for 3 hours, and then the reaction was completed. Tetrahydrofuran was removed under reduced pressure at room temperature. Purified water was added and the mixture was freeze-dried to obtain a crude product of sodium 2-(trifluoromethyl)pyridine-3-sulfide (C3, 500 mg, yield: more than 100%) as a light yellow solid. LCMS: m/z 179.9 [M+H]$^+$ Synthesis of Intermediate C4: sodium 2-(trifluoromethyl)pyridine-4-sulfide

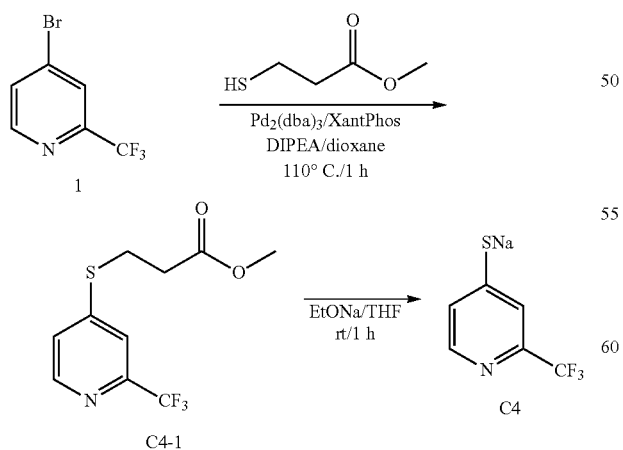

Step 1: 4-bromo-2-trifluoromethylpyridine (1.0 g, 4.4 mmol, 1.0 eq), methyl 3-mercaptopropionate (760 mg, 6.3 mmol, 1.4 eq) and N,N-diisopropylethylamine (2.17 g, 16.8 mmol, 3.8 eq) were dissolved in 1,4-dioxane (25 mL), the atmosphere in the reaction system was replaced with argon three times, and Pd$_2$(dba)$_3$ (200 mg, 0.22 mmol, 0.05 eq) and XantPhos (124 mg, 0.22 mmol, 0.05 eq) were added under the protection of argon. Then the mixture was heated to 110° C. and reacted for 1 hour, and then the reaction was completed. The mixture was extracted with ethyl acetate (100 mL), filtered through diatomite, concentrated, and passed through column (PE:EA=5/1) to obtain methyl 3-((2-(trifluoromethyl)pyridin-4-yl)thio)propionate (C4-1, 1.08 g, yield: 97%) as a light yellow oily matter. LCMS: m/z 266.2 [M+H]$^+$ Step 4: 3-((2-(trifluoromethyl)pyridin-4-yl)thio)propionate (C4-1, 230 mg, 0.85 mmol, 1.0 eq) was dissolved in tetrahydrofuran (10 mL) and ethanol (0.5 mL). Sodium alcohol (294 mg, 0.87 mmol, 1.02 eq) was added under the protection of nitrogen, the mixture was reacted at room temperature for 1 hour, and the reaction was completed. Tetrahydrofuran was removed under reduced pressure at room temperature. Purified water was added and the mixture was freeze-dried to obtain a crude product of sodium 2-(trifluoromethyl)pyridine-4-sulfide (C4, 150 mg) as a light yellow solid. LCMS: m/z 180.0 [M+H]$^+$ Synthesis of Intermediate C5: sodium 2-(trifluoromethyl)pyridine-4-sulfide

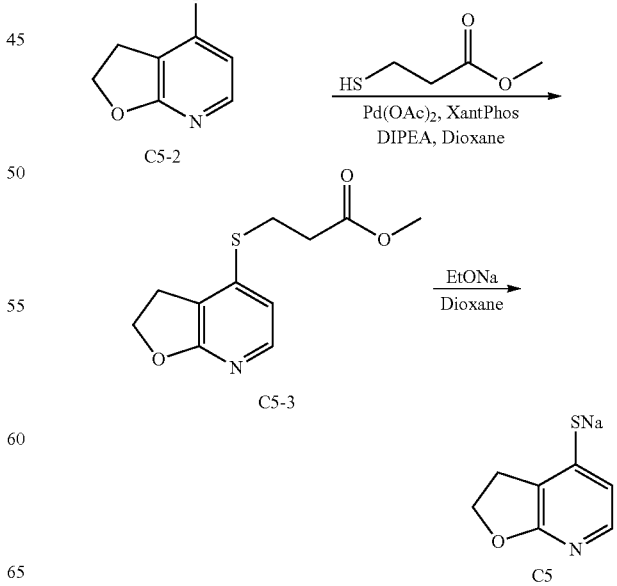

Step 1: 2-fluoro-4-iodopyridine (2.0 g, 8.97 mmol) was dissolved in THF (30 mL). The atmosphere in the reaction system was replaced with nitrogen three times, then the temperature was reduced to −65° C., and LDA (2.0 M in THF, 5.4 ml, 10.80 mmol) was added dropwise. The reaction solution gradually turned brown. After the addition of LDA was completed, the temperature was maintained for 1.5 hours. A solution of 1,3,2-dioxothiophene-2,2-dioxide (1.45 g, 11.7 mmol) in THF (30 mL) was added dropwise. Then the mixture was warmed to room temperature naturally and stirred overnight. The raw material was confirmed to be disappeared by TLC (petroleum ether/ethyl acetate=1/1). The reaction mixture was cooled to 0° C., and concentrated hydrochloric acid (4.48 ml, 40.2 mmol) was added dropwise. Then the mixture was heated to room temperature and stirred for 3 hours. The reaction liquid was poured into saturated NaHCO$_3$ aqueous solution (50 mL), extracted with ethyl acetate (3×30 mL), washed with saturated brine (50 mL), dried over anhydrous sodium sulfate, filtered, and concentrated to dry, and then purified by silica gel chromatography to obtain 2-(2-fluoro-4-iodopyridin-3-yl)ethane-1-ol (C5-1, 2.07 g, yield: 86.2%).

Step 2: Potassium carbonate (4.28 g, 30.9 mmol) was added to a solution of 2-(2-fluoro-4-iodopyridin-3-yl)ethane-1-ol (C5-1, 2.07 g, 8.97 mmol) in dioxane (60 mL). The mixture was stirred at 115° C. for 48 hours under the protection of nitrogen. LCMS and TLC (petroleum ether/ethyl acetate=1/1) indicated that there were basically raw materials and only a small amount of products in the reaction system. Cesium carbonate (7.56 g, 23.2 mmol) was added, and the reaction continued at 115° C. for 6 hours. The raw materials were confirmed to be almost completely reacted by LCMS and TLC (petroleum ether/ethyl acetate=1/1). The reaction solution was cooled to room temperature, diluted with ethyl acetate, filtered with diatomite and eluted with ethyl acetate. The filtrate was washed with saturated brine (2×50 mL), dried over anhydrous sodium sulfate, filtered, concentrated to dry and then purified by silica gel column chromatography (ethyl acetate/petroleum ether/dichloromethane=0/5/2 to 1/5/2) to obtained 4-iodo-2,3-dihydrofurano[2,3-b]pyridine (C5-2, 1.21 g, yield: 63.2%) as a white solid. LCMS: m/z 248.2 [M+H]$^+$ Step 3: Methyl 3-mercaptopropionate (437 mg, 3.64 mmol), DIPEA (1.26 g, 9.71 mmol), XantPhos (70 mg, 0.12 mmol) and Pd(OAC)$_2$ (30 mg, 0.13 mmol) were added to a solution of 4-iodo-2,3-dihydrofurano[2,3-b]pyridine (C5-2, 600 mg, 2.43 mmol) in dioxane (10 mL). Under the protection of nitrogen, the mixture was heated to 100° C. and reacted for 3 hours. TLC (petroleum ether/ethyl acetate=1/1) and LCMS indicated that the reaction was completed. The reaction solution was diluted with ethyl acetate and filtered. The filtrate was concentrated to dry, and purified by silica gel column chromatography to obtain methyl 3-((2,3-dihydrofurano[2,3-b]pyridin-4-yl)thio)propionate (C5-3, 565 mg, yield: 97.2%). LCMS: m/z 240.3 [M+H]$^+$ Step 4: Sodium ethoxide ethanol solution (20%(w/w), 185 mg, 0.54 mmol) was added to a solution of methyl 3-((2,3-dihydrofurano[2,3-b]pyridin-4-yl)thio)propionate (C5-3, 145 mg, 0.61 mmol) in THF (5 mL) at 0° C. The mixture was reacted at room temperature for 2 hours, and TLC (ethyl acetate/petroleum ether=1/1) and LCMS indicated that the reaction was completed. Without further processing, the reaction liquid was directly used for the next reaction.

Synthesis of Intermediate C6: sodium 2-methylamino-3 chloropyridine-4-sulfide

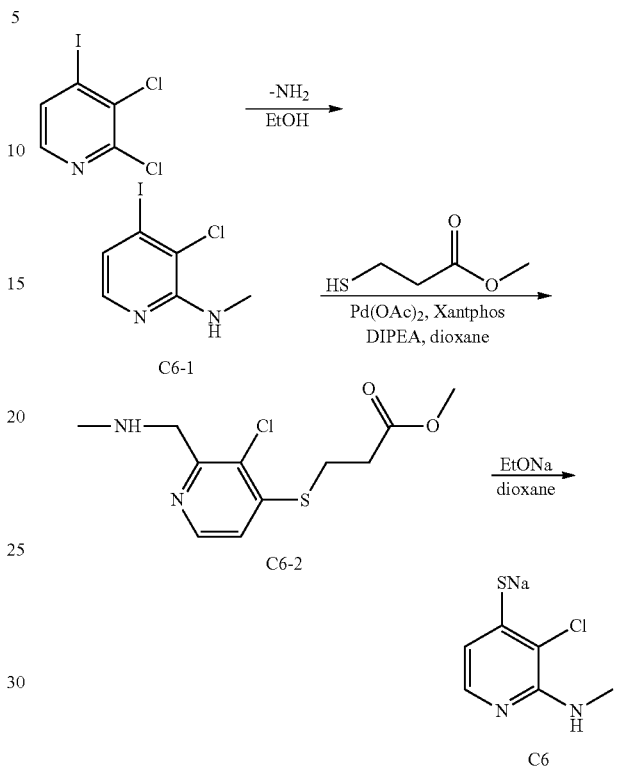

Step 1: 2,3-dichloro-4-iodopyridine (1.0 g, 3.65 mmol) reacted with methylamine/ethanol solution (27%, 25 mL) in a closed tank at 100° C. for 12 hours. TLC monitoring indicated that the reaction was completed (petroleum ether:ethyl acetate=5:1). The reaction solution was concentrated under reduced pressure and purified by silica gel chromatography (0-5% gradient of ethyl acetate:petroleum ether) to obtain 3-chloro-4-iodo-N-methylpyridine-2-amine (C6-1, 400 mg, yield: 41%). LCMS: m/z 268.9 [M+H]$^+$ Step 2: XantPhos (72 mg, 0.15 mmol), Pd(OAC)$_2$ (34 mg, 0.15 mmol), DIPEA (770 mg, 5.96 mmol) and methyl 3-mercaptopropionate (270 mg, 2.23 mmol) were added to a solution of 3-chloro-4-iodo-N-methylpyridine-2-amine (C6-1, 400 mg, 1.49 mmol) in anhydrous 1,4-dioxane (20 mL). The mixture was reacted for 5 h at 100° C. TLC (petroleum ether:ethyl acetate=5/1) indicated that the reaction was completed. After the reaction mixture was cooled to room temperature, water (50 mL) and ethyl acetate (30 mL) were added, and the layers were separated. The aqueous phase was extracted with ethyl acetate (2×40 mL). The organic phase was combined, washed with saturated brine (3×50 mL), dried over anhydrous sodium sulfate, filtered, concentrated, and purified by silica gel chromatography (petroleum ether:ethyl acetate=10:1) to obtain methyl 3-((3-chloro-2-(methylamino)pyridin-4-yl)thio)propionate (C6-2, 250 mg, yield: 65%). LCMS: m/z 261.0 [M+H]$^+$ Step 3: Methyl 3-((3-chloro-2-(methylamino)pyridin-4-yl)thio)propionate (C6-2, 114 mg, 0.44 mmol) was dissolved in dioxane (6 mL). Under the protection of argon, a solution of EtONa (20%(w/w), 150 mg, 0.44 mmol) in ethanol was added dropwise, and the mixture was stirred at room temperature for about 2.5 hours. LCMS indicated the reaction was completed. The reaction solution was directly used for the next reaction (yield: 100%). LCMS: m/z 174.8 [M+H–23]$^+$ Synthesis of Intermediate C7: sodium 1-(tetrahydro-2H-pyran-2-yl)-1H-pyrazolo[3,4-b]pyridine-4-mercaptan

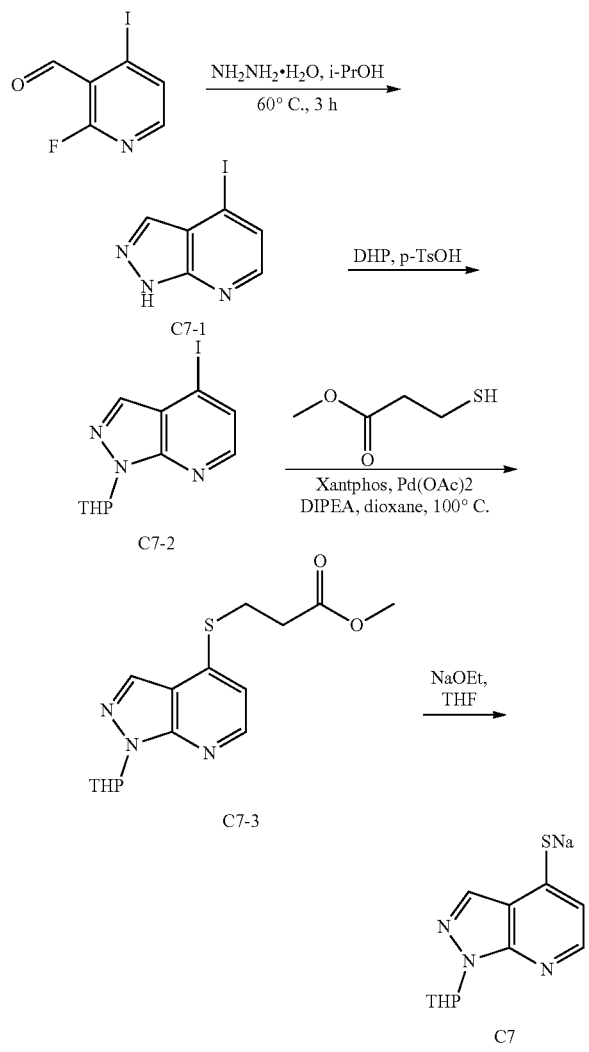

Step 1: Hydrazine hydrate (3032 mg, 60.56 mmol) was added to a solution of 2-fluoro-3-formyl-4-iodopyridine (1900 mg, 7.57 mmol) in isopropanol (30 mL), and the mixture was stirred at 60° C. for 3 h. The reaction solution was concentrated under reduced pressure to remove part of the solvent, then poured into water, and filtered. The filter cake was washed with water to obtain 4-iodo-1H-pyrazolo[3,4-b]pyridine (C7-1, 1.8 g, yield: 97%) as a light yellow solid. $^1$H NMR (400 MHz, CDCl$_3$): δ 8.19 (d, J=4.4 Hz, 1H), 7.98 (s, 1H), 7.68 (d, J=4.8 Hz, 1H).

Step 2: P-toluenesulfonic acid (28 mg, 0.16 mmol) and DHP (206 mg, 2.45 mmol) were added to a solution of 4-iodo-1H-pyrazolo[3,4-b]pyridine (C7-1, 400 mg, 1.63 mmol) in tetrahydrofuran (10 mL) successively. The mixture was stirred at 60° C. for 16 h. The reaction solution was diluted with ethyl acetate (40 mL), washed with saturated brine (2×40 mL), dried over anhydrous sodium sulfate, and filtered. The filtrate was concentrated under reduced pressure. The obtained residue was purified by silica gel chromatography (0-50% gradient of ethyl acetate:petroleum ether) to obtain 4-iodo-1-(tetrahydro-2H-pyran-2-yl)-1H-pyrazolo[3,4-B]pyridine (C7-2, 390 mg, yield: 73%) as a light yellow solid. $^1$H NMR (400 MHz, CDCl$_3$): δ 8.17 (d, J=4.8 Hz, 1H), 7.93 (s, 1H), 7.58 (d, J=5.2 Hz, 1H), 6.10 (dd, J=10.4, 2.4 Hz, 1H), 4.14-4.10 (m, 1H), 3.82 (td, J=11.6, 2.8 Hz, 1H), 2.69-2.59 (m, 1H), 2.17-2.13 (m, 1H), 2.00-1.96 (m, 1H), 1.83-1.74 (m, 2H), 1.64-1.62 (m, 1H).

Step 3: 4-iodo-1-(tetrahydro-2H-pyran-2-yl)-1H-pyrazolo[3,4-B]pyridine (C7-2, 390 mg, 1.18 mmol), methyl 3-mercaptopropionate (157 mg, 1.30 mmol) and N,N-diisopropylethylamine (306 mg, 2.37 mmol) were dissolved in 1,4-dioxane (10 mL), the atmosphere in the reaction system was replaced with argon three times, and Pd(OAc)$_2$ (27 mg, 0.12 mmol) and Xantphos (137 mg, 0.24 mmol) were added under the protection of argon. After the addition was completed, the mixture was heated to 110° C. and reacted for 2 h, and the reaction was completed. The mixture was extracted with ethyl acetate (30 mL), washed with saturated brine (2×30 mL), dried over anhydrous sodium sulfate, and filtered. The filtrate was concentrated under reduced pressure. The obtained residue was purified by silica gel chromatography (0-50% gradient of ethyl acetate:petroleum ether) to obtain methyl 3-((1H-pyrazolo[3,4-b]pyridin-4-yl)thio)propionate (C7-3, 280 mg, yield: 74%) as a yellowish brown oily matter. LCMS: m/z 322.3 [M+H]$^+$ $^1$H NMR (400 MHz, CDCl$_3$): δ 8.40 (d, J=5.2 Hz, 1H), 8.08 (s, 1H), 6.95 (d, J=5.2 Hz, 1H), 6.10 (dd, J=10.8, 2.4 Hz, 1H), 4.14~4.10 (m, 1H), 3.83 (td, J=11.2 Hz, 1H), 3.73 (s, 3H), 3.40 (t, J=7.2 Hz, 2H), 2.79 (t, J=7.2 Hz, 2H), 2.68~2.58 (m, 1H), 2.16~2.13 (m, 1H), 2.00~1.55 (m, 2H), 1.63~1.60 (m, 1H).

Step 4: Methyl 3-((1H-pyrazolo[3,4-b]pyridin-4-yl)thio)propionate (C7-3, 280 mg, 0.87 mmol) was dissolved in 1,4-dioxane (7 mL) in a three-necked flask with a condenser tube. Under the protection of nitrogen, the mixture was cooled to 0° C., and sodium ethoxide ethanol solution (20%(w/w), 266 mg, 0.78 mmol) was added. The mixture was stirred for 2 h at room temperature. TLC (dichloromethane/methanol=20/1) testing indicated that the reaction was completed, and the reaction liquid containing sodium 1-(tetrahydro-2H-pyran-2-yl)-1H-pyrazolo[3,4-b]pyridine-4-mercaptan (C7) was directly used for the next step.

Example 1: Synthesis of Compound 1

(S)-1'-((2,3-dihydrofuran[2,3-b]pyridin-4-yl)thio)imidazolo[1,2-c]pyrimidin-5-yl)-5,7-dihydrospirocyclopenta[b]pyridine-6,4'-piperidine]-5-amine

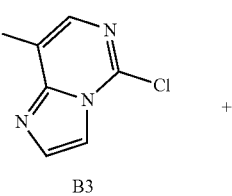
+

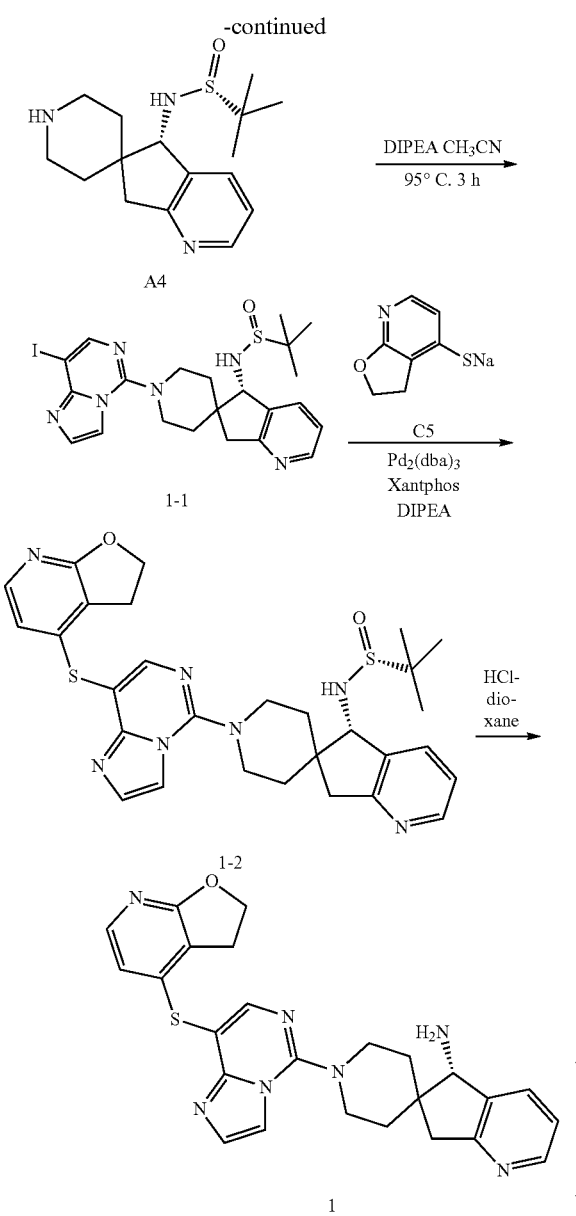

mmol) were added. Under the protection of nitrogen, the mixture was heated to 100° C. and stirred for 3 hours. TLC (petroleum ether/ethyl acetate=1/1) and LCMS indicated that the reaction was completed. The reaction solution was diluted with ethyl acetate and filtered. The filter residue was eluted with ethyl acetate. The filtrate was concentrated to dry and purified by silica gel column chromatography to obtain (S)—N—((S)-1'-(8-((2,3-dihydrofuran[2,3-b]pyridin-4-yl)thio)imidazolo[1,2-c]pyrimidin-5-yl)-5,7-dihydrospirocyclopenta[b]pyridin-6,4'-piperidin]-5-yl)-2-methylpropane-2-sulfanilamide (1-2, 217 mg, yield: 98.9%). LCMS: m/z 576.6 [M+H]$^+$ Step 3: Under the protection of nitrogen, HCl/dioxane (4 M, 0.2 mL, 0.80 mmol) was slowly added to a solution of (S)—N—((S)-1'-(8-((2,3-dihydrofuran[2,3-b]pyridin-4-yl)thio)imidazolo[1,2-c]pyrimidin-5-yl)-5,7-dihydrospirocyclopenta[b]pyridin-6,4'-piperidin]-5-yl)-2-methylpropane-2-sulfanilamide (50 mg, 0.29 mmol) in dichloromethane (5 mL) at 0° C., the mixture was stirred at room temperature for 2 hours, and TLC (dichloromethane/methanol=8/1) and LCMS indicated the reaction was completed. The reaction solution was cooled to 0° C., ammonia methanol solution was slowly added to adjust the pH to about 10, and then the mixture was concentrated under reduced pressure and purified by prep-HPLC to obtain a formate of (S)-1'-(8-((2,3-dihydrofuran[2,3-b]pyridin-4-yl)thio)imidazolo[1,2-c]pyrimidin-5-yl)-5,7-dihydrospirocyclopentadiene[b]pyridine-6,4'-piperidine]-5-amine (compound 1, 8.86 mg, yield: 20.0%). LCMS: m/z 472.5 [M+H]$^+$ $^1$H NMR (400 MHz, MeOD) δ 8.47 (d, J=4.0 Hz, 2H), 8.09 (s, 1H), 7.92 (d, J=7.6 Hz, 1H), 7.85 (d, J=1.6 Hz, 1H), 7.59 (d, J=1.6 Hz, 1H), 7.55 (d, J=6.0 Hz, 1H), 7.37~7.34 (m, 1H), 6.21 (d, J=5.6 Hz, 1H), 4.72~4.67 (m, 2H), 4.38 (s, 1H), 4.06~4.03 (m, 2H), 3.48~3.42 (m, 2H), 3.28 (s, 2H), 3.14 (d, J=16.8 Hz, 2H), 2.11~2.078 (m, 2H), 1.76~1.70 (m, 2H).

Example 2: Synthesis of Compound 2

(S)-1'-(8-((2-amino-3-chloropyridin-4-yl)thio)-[1,2,4]triazol[4,3-c]pyrimidin-5-yl)-1,3-dihydrospiro[indene-2,4'-piperidine]-1-amine Step 1: Under the protection of nitrogen, 5-chloro-8-iodoimidazo[1,2-c]pyrimidine (B3, 80 mg, 0.285 mmol), ((R)—N—((S)-1,3-dihydrospiro[indene-2,4'-piperidin]-1-yl)-2-methylpropane-2-sulfinamide (A4,105 mg, 0.342 mmol), DIEA (55 mg, 0.428 mmol) and CH$_3$CN (5 mL) were added to a dry 25 mL single-necked flask successively, and then the mixture was stirred at 95° C. for 3 hours. After the reaction was completed, the obtained reaction solution was filtered and concentrated under reduced pressure. The obtained residue was purified by silica gel chromatography (0-10% gradient of methanol/ethyl acetate) to obtain a compound (1-1, 101 mg, yield: 65%). LCMS: m/z 551.1 [M+H]+.

Step 2: Sodium 2,3-dihydrofuran[2,3-b]pyridin-4-thioformate (107 mg, 0.61 mmol) was added to dioxane (15 mL) for dilution, and then (S)—N—((S)-1'-(8-iodoimidazolo[1,2-C]pyrimidin-5-yl)-5,7-dihydrospiro[cyclopentane[B]pyridin-6,4'-piperidin]-5-yl)-2-methylpropane-2-sulfinamide (1-1, 200 mg, 0.36 mmol), DIPEA (141 mg, 1.09 mmol), XantPhos (63 mg, 0.11 mmol) and Pd$_2$(dba)$_3$ (50 mg, 0.06

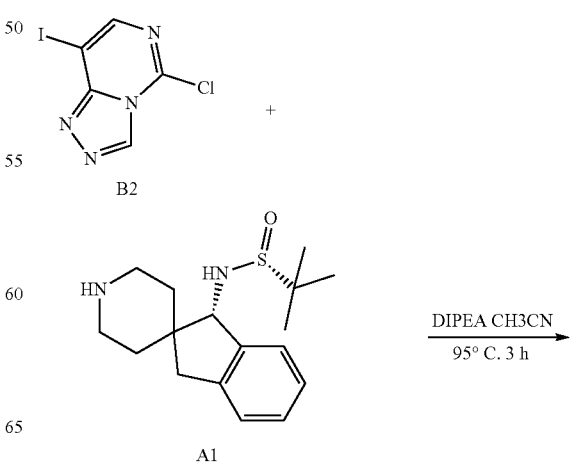

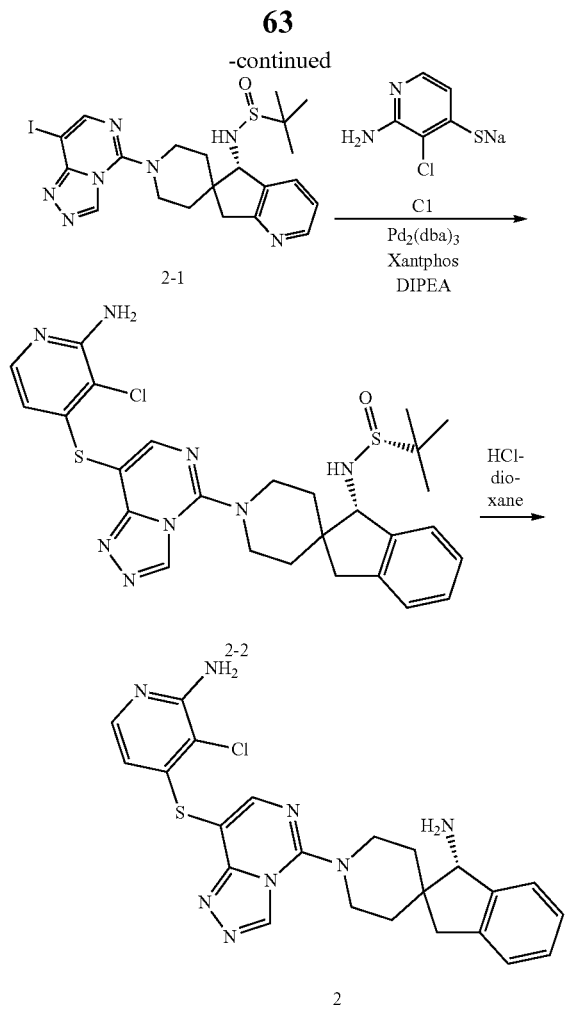

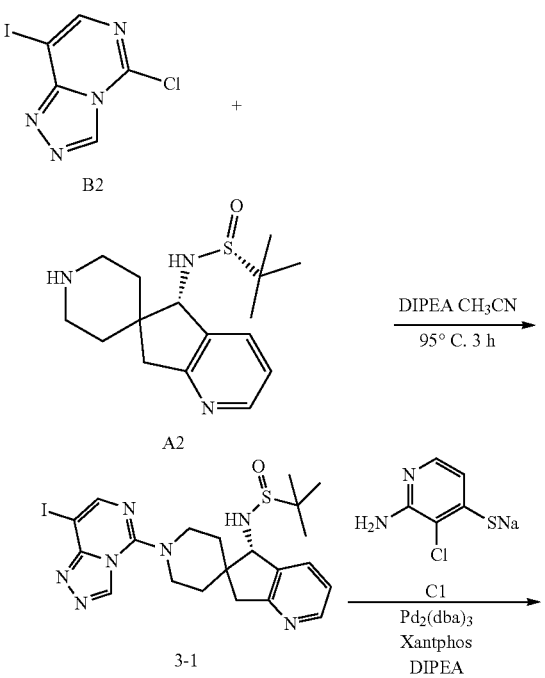

Step 1: Under the protection of nitrogen, 5-chloro-8-iodo-[1,2,4]triazolo[4,3-c]pyrimidine (B2, 80 mg, 0.285 mmol), ((R)—N—((S)-1,3-dihydrospiro[indene-2,4'-piperidin]-1-yl)-2-methylpropane-2-sulfinamide (A1, 105 mg, 0.342 mmol), DIEA (55 mg, 0.428 mmol) and $CH_3CN$ (5 mL) were added to a dry 25 mL single-necked flask successively, and then the mixture was stirred for 3 hours at 95° C. After the reaction was completed, the obtained residue was filtered and concentrated under reduced pressure. The obtained residue was purified by silica gel chromatography (0-10% gradient of methanol/ethyl acetate) to obtain (R)—N—((S)-1'-(8-iodo-[1,2,4]triazolo[4,3-c]pyrimidin-5-yl)-1,3-dihydrospiro[indene-2,4'-piperidin]-1-yl)-2-methylpropane-2-sulfinamide (2-1, 101 mg, yield: 65%) as a yellow solid. LCMS: m/z 551.1 $[M+H]^+$.

Step 2: Under the protection of nitrogen, (R)—N—((S)-1'-(8-iodo-[1,2,4]triazolo[4,3-c]pyrimidin-5-yl)-1,3-dihydrospiro[indene-2,4'-piperidin]-1-yl)-2-methylpropane-2-sulfinamide (2-1, 100 mg, 0.18 mmol), sodium 2-amino-3-chloropyridine-4-mercaptan (49 mg, 0.27 mmol), $Pd_2(dba)_3$ (16 mg, 0.018 mmol), Xantphos (21 mg, 0.036 mmol), DIPEA (58 mg, 0.45 mmol) and 1,4-dioxane solution (10 mL) were added to a 5 mL microwave reaction flask successively, and the mixture was microwaved to 100° C. and stirred for 3 hours under the protection of nitrogen. After the reaction was completed, the mixture was cooled to room temperature, filtered and concentrated under reduced pressure. The obtained residue was purified by silica gel chromatography (0-10% gradient of methanol/ethyl acetate) to obtain (R)—N—((R)-1'-(8-((2-amino-3-chloropyridin-4-yl)thio)-[1,2,4]triazolo[4,3-c]pyrimidin-5-yl)-1,3-dihydrospiro[indene-2,4'-piperidin]-1-yl)-2-methylpropane-2-sulfinamide (2-2, 65 mg, yield: 63%). LC-MS: m/z 584.2 $[M+H]^+$.

Step 3: Under the protection of nitrogen, (R)—N—((R)-1'-(8-((2-amino-3-chloropyridin-4-yl)thio)-[1,2,4]triazolo[4,3-c]pyrimidin-5-yl)-1,3-dihydrospiro[indene-2,4'-piperidin]-1-yl)-2-methylpropane-2-sulfinamide (2-2, 60 mg, 0.10 mmol) and methanol (0.6 mL) were added to a 50 mL single-necked flask successively, hydrochloric acid 1,4-dioxane solution (0.06 mL, 4M) was added dropwise at room temperature, and the mixture was stirred at room temperature for 1 hour. After the reaction was completed, the mixture was cooled to room temperature, filtered and concentrated under reduced pressure. The obtained residue was purified by preparative high performance liquid chromatography to obtain (S)-1'-(8-((2-amino-3-chloropyridin-4-yl)thio)-[1,2,4]triazolo[4,3-c]pyrimidin-5-yl)-1-1,3-dihydrospiro[indene-2,4'-piperidine]-1-amine (compound 2, 20 mg, yield: 42%).

$^1$H NMR (400 MHz, DMSO-d6) δ 9.38 (s, 1H), 7.98 (s, 1H), 7.58 (d, J=5.4 Hz, 1H), 7.36 (d, J=4.8 Hz, 1H), 7.22 (dt, J=8.0, 4.0 Hz, 3H), 6.33 (s, 2H), 5.96 (d, J=5.6 Hz, 1H), 4.22-4.07 (m, 2H), 4.00 (s, 1H), 3.49 (dd, J=22.5, 11.2 Hz, 2H), 3.12 (d, J=15.6 Hz, 1H), 2.75 (d, J=15.6 Hz, 1H), 2.03-1.86 (m, 2H), 1.63 (d, J=13.6 Hz, 1H), 1.39-1.29 (m, 1H);

LC-MS: m/z 479.1 $[M+H]^+$.

Example 3: Synthesis of Compound 3

(S)-1'-(8-((2-amino-3-chloropyridin-4-yl)thio)-[1,2,4]triazolo[4,3-c]pyrimidin-5-yl)-5,7-dihydrospiro[cyclopenta[b]pyridine-6,4'-piperidine]-5-amine

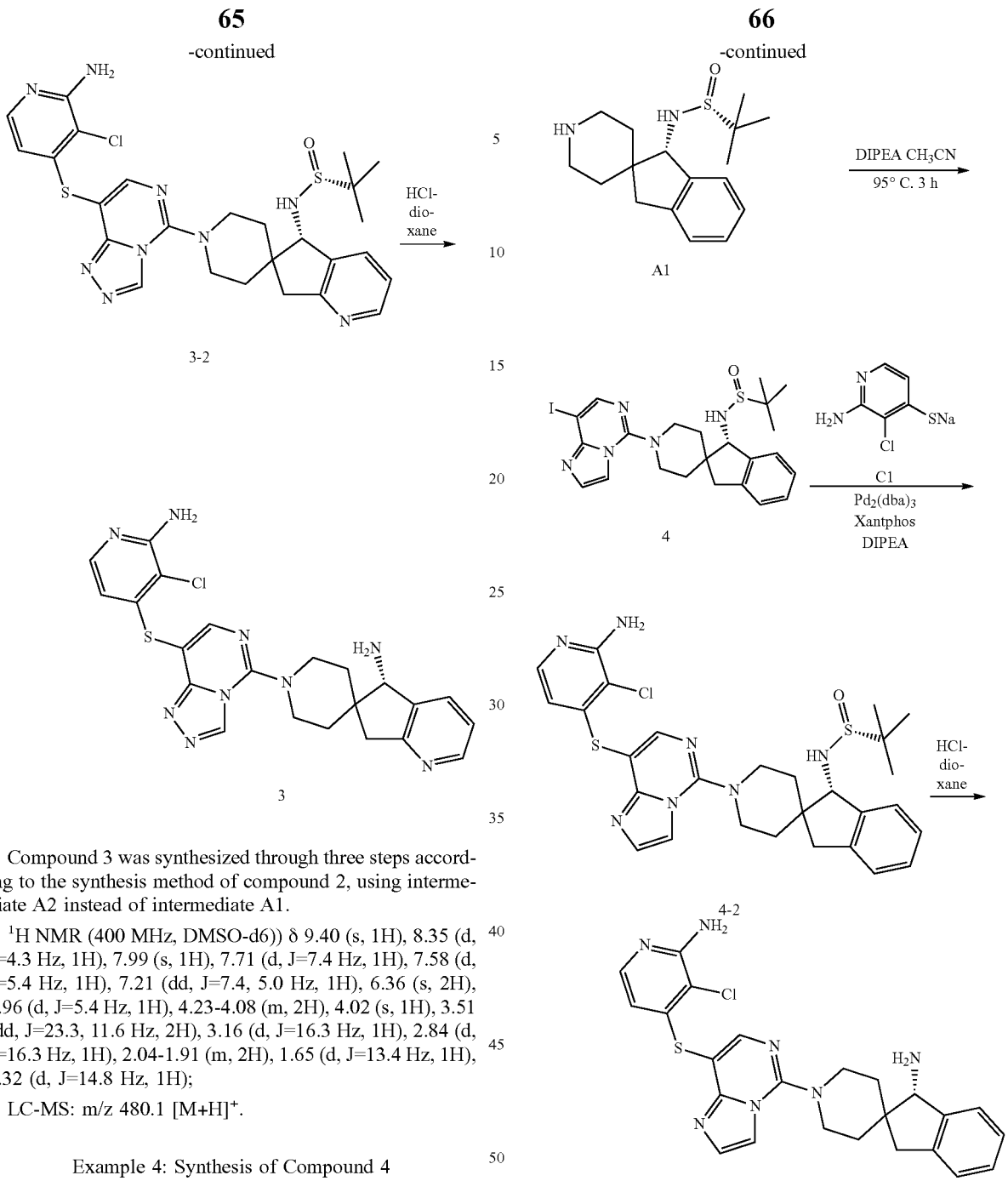

Compound 3 was synthesized through three steps according to the synthesis method of compound 2, using intermediate A2 instead of intermediate A1.

¹H NMR (400 MHz, DMSO-d6)) δ 9.40 (s, 1H), 8.35 (d, J=4.3 Hz, 1H), 7.99 (s, 1H), 7.71 (d, J=7.4 Hz, 1H), 7.58 (d, J=5.4 Hz, 1H), 7.21 (dd, J=7.4, 5.0 Hz, 1H), 6.36 (s, 2H), 5.96 (d, J=5.4 Hz, 1H), 4.23-4.08 (m, 2H), 4.02 (s, 1H), 3.51 (dd, J=23.3, 11.6 Hz, 2H), 3.16 (d, J=16.3 Hz, 1H), 2.84 (d, J=16.3 Hz, 1H), 2.04-1.91 (m, 2H), 1.65 (d, J=13.4 Hz, 1H), 1.32 (d, J=14.8 Hz, 1H);

LC-MS: m/z 480.1 [M+H]⁺.

Example 4: Synthesis of Compound 4

(S)-1'-(8-((2-amino-3-chloropyridin-4-yl)thio)imidazolo[1,2-c]pyrimidin-5-yl)-1,3-dihydrospiro[indene-2,4'-piperidine]-1-amine

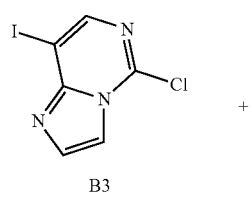

Compound 4 (formate, white solid) was synthesized through three steps according to the synthesis method of compound 2, using intermediate B3 instead of intermediate B2.

¹H NMR (400 MHz, DMSO-d6) δ8.03 (s, 1H), 7.83 (s, 1H), 7.64-7.49 (m, 2H), 7.43 (s, 1H), 7.30-7.17 (m, 3H), 6.33 (s, 2H), 5.79 (d, J=5.2 Hz, 1H), 4.12 (s, 1H), 3.95 (d, J=12.8 Hz, 2H), 3.33 (dd, J=20.0, 10.8 Hz, 2H), 3.14 (d, J=15.6 Hz, 1H), 2.82 (d, J=15.6 Hz, 1H), 1.98 (d, J=9.6 Hz, 2H), 1.61 (d, J=12.8 Hz, 1H), 1.42 (d, J=12.8 Hz, 1H), 1.23 (s, 2H);

LC-MS: m/z 478.1 [M+H]⁺.

Example 5: Synthesis of Compound 5

(S)-1'-(8-((3-chloro-2-(methylamino)pyridin-4-yl)thio)imidazo[1,2-c]pyrimidin-5-yl)-5,7-dihydrospiro[cyclopenta[b]pyridine-6,4'-piperidine]-5-amine

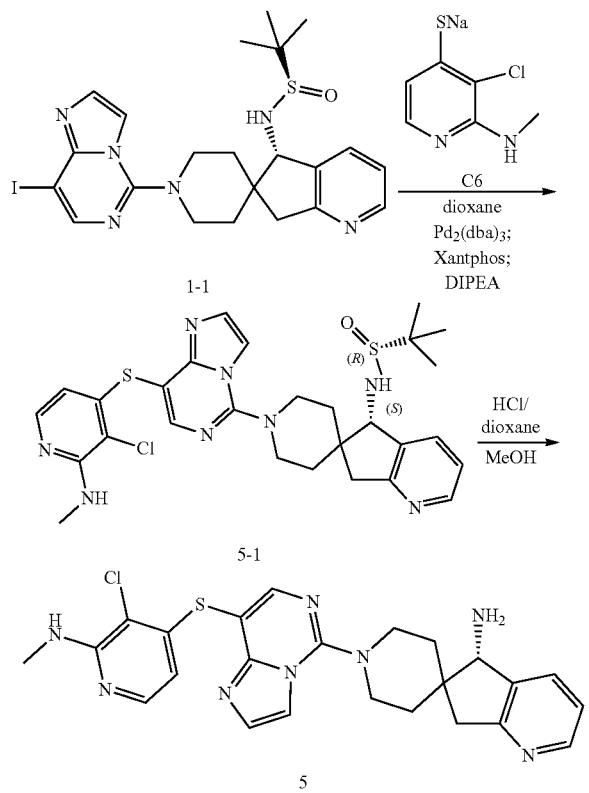

Step 1: sodium 2-methylamino-3-chloropyridin-4 sulfide (C6, 86 mg) was dissolved in 10 mL of dioxane solution, and (R)—N—((S)-1'-(8-iodoimidazolo[1,2-C]pyrimidin-5-yl)-5,7-dihydrospiro[cyclopenta[b]pyridin-6,4'-piperidin]-5-yl)-2-methylpropane-2-sulfinamide (161 mg, 0.29 mmol), Pd$_2$(dba)$_3$ (86 mg, 0.094 mmol), Xantphos (108 mg, 0.19 mmol) and DIPEA (400 mg, 3.12 mmol) were added. The mixture was reacted at 100° C. for 5 h under the protection of argon. LCMS testing indicated the reaction was completed. After the mixture was cooled to room temperature, dichloromethane (30 mL) was added, and the mixture was filtered. Water (40 mL) was added to the mother liquor and the layers were separated. The aqueous phase was extracted with dichloromethane (2×30 mL). The organic phases were combine, washed with saturated brine (3×40 mL), dried over anhydrous sodium sulfate, filtered, and purified by silica gel chromatography (dichloromethane:methanol=15:1) to obtain (R)—N-((s)-1'-(8-((3-chloro-2-(methylamino)pyridin-4-yl)thio)imidazo[1,2-c]pyrimidin-5-yl)-5,7-dihydrospiro[cyclopenta[b]pyridin-6,4'-piperidin]-5-yl)-2-methylpropane-2-sulfinamide (5-1, 135 mg, yield: 73%) as a light yellow solid. LCMS: m/z 596.9 [M+H]$^+$.

Step 2: (R)—N-((s)-1'-(8-((3-chloro-2-(methylamino)pyridin-4-yl)thio)imidazo[1,2-c]pyrimidin-5-yl)-5,7-dihydrospiro[cyclopenta[b]pyridin-6,4'-piperidin]-5-yl)-2-methylpropane-2-sulfinamide (135 mg, 0.23 mmol) was dissolved in methanol (20 mL), HCl/dioxane (4 M, 1.2 mL) was slowly added dropwise under the protection of nitrogen, and the mixture was reacted at room temperature for 40 minutes. LCMS testing indicated the reaction was completed. The reaction solution was poured into icy saturated sodium bicarbonate solution. The mixed solution was freeze-dried, and dichloromethane/methanol (10:1, 20 mL) was added. The mixture was filtered. The filtrate was concentrated to dry, and then purified by prep-HPLC to obtain a white solid (compound 5, 33 mg, yield: 30%). LCMS: m/z 493.0 [M+H]$^+$.

$^1$H NMR (400 MHz, DMSO-d6) δ 8.33 (d, J=4.4 Hz, 1H), 8.03 (s, 1H), 7.84 (d, J=1.2 Hz, 1H), 7.69 (d, J=7.6 Hz, 1H), 7.65 (d, J=5.2 Hz, 1H), 7.57 (d, J=1.2 Hz, 1H), 7.20 (dd, J=7.2, 5.2 Hz, 1H), 6.60 (q, J=4.4 Hz, 1H), 5.81 (d, J=5.2 Hz, 1H), 3.98-3.89 (m, 3H), 3.38-3.22 (m, 2H), 3.15-3.11 (d, J=16.0 Hz, 1H), 2.85 (d, J=4.8 Hz, 3H), 2.81 (d, J=16.4 Hz, 1H), 2.50-2.39 (m, 1H), 2.05-1.90 (m, 3H), 1.67 (d, J=13.2 Hz, 1H), 1.28-1.25 (d, J=13.2 Hz, 1H).

Example 6: Synthesis of Compound 6

(S)-1'-(8-((2-amino-3-chloropyridin-4-yl)thio)imidazo[1,2-c]pyrimidin-5-yl)-5,7-dihydrospiro[cyclopenta[b]pyridine-6,4'-piperidine]-5-amine

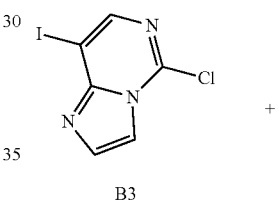

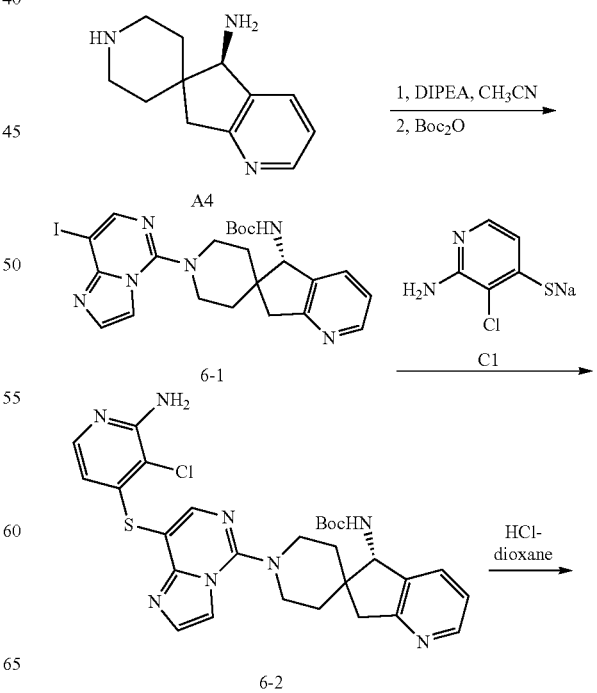

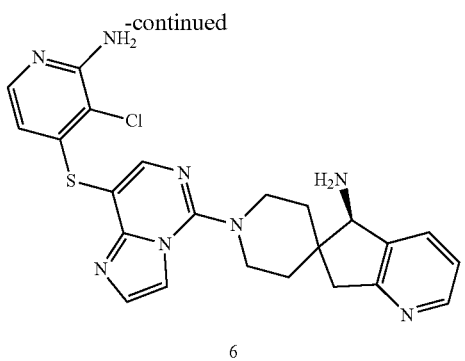

6

Step 1: B3 (1.37 g, 4.9 mmol), A4 (1.35 g, 4.9 mmol) and DIPEA (4.86 ml, 29.41 mmol) were successively added to 3 mL acetonitrile in a 25 mL single-necked flask, and then the mixture was stirred for 2 hours at 80° C. After the reaction was completed, the mixture was cooled to room temperature, then Boc$_2$O (1.6 g, 7.35 mmol, 1.5 eq) was added, and the mixture was heated to 50° C. and reacted until the reaction was completed. The reaction solution was concentrated under reduced pressure to obtain a residue. The residue was purified by silica gel chromatography (0-100% gradient of ethyl acetate/petroleum ether) to obtain 6-1 (1.7 g, yield: 63.4%) as a yellow solid. LC-MS: m/z=547.0 [M+H$^+$]

Step 2: Under the protection of nitrogen, 6-1 (1.7 g, 3.11 mmol), sodium 2-amino-3-chloropyridine-4-mercaptan (596 mg, 3.27 mmol), Pd$_2$(dba)$_3$ (285 mg, 0.311 mmol), Xantphos (360 mg, 0.622 mmol), DIPEA (804 mg, 6.22 mmol) and 1,4-dioxane solution (30 mL) were added to a 5 mL microwave reaction flask successively, and the mixture was microwaved to 100° C. and stirred for 3 hours under the protection of nitrogen. After the reaction was completed, the mixture was cooled to room temperature, filtered and concentrated under reduced pressure to obtain a residue. The residue was purified by silica gel chromatography (0-10% gradient of ethyl acetate/methanol) to obtain (S)-tert-butyl (1'-(8-((2-amino-3-chloropyridin-4-yl)thio)imidazolo[1,2-c]pyrimidin-5-yl)-5,7-dihydrospiro[cyclopenta[b]pyridin-6,4'-piperidin]-5-yl)-carbonate (6-2, 1.2 g, 66.7%).

Step 3: Under the protection of nitrogen, TFA (5 mL) was slowly added to a solution of (S)-tert-butyl (1'-(8-((2-amino-3-chloropyridin-4-yl)thio)imidazolo[1,2-c]pyrimidin-5-yl)-5,7-dihydrospiro[cyclopenta[b]pyridin-6,4'-piperidin]-5-yl)-carbonate (6-2, 1.2 g, 2.07 mmol) in dichloromethane (5 mL) at 0° C., the mixture was stirred at room temperature for 1 hour, and TLC and LCMS indicated the reaction was completed. The reaction solution was concentrated under reduced pressure, then dichloromethane/methanol mixed solution was added for dissolution, and the pH of the mixture was adjusted to neutral with NaHCO$_3$. The mixture was purified by passing through silica gel column to obtain (S)-1'-(8-((2-amino-3-chloropyridin-4-yl)thio)imidazo[1,2-c]pyrimidin-5-yl)-5,7-dihydrospiro[cyclopenta[b]pyridine-6,4'-piperidine]-5-amine (compound 6, 400 mg, yield: 40.0%).

$^1$H NMR (400 MHz, DMSO-d6) δ 8.35 (d, J=4.0 Hz, 1H), 8.03 (s, 1H), 7.83 (d, J=1.2 Hz, 1H), 7.72 (d, J=7.6 Hz, 1H), 7.56 (dd, J=10.4, 3.4 Hz, 2H), 7.20 (dd, J=7.6, 5.2 Hz, 1H), 6.33 (s, 2H), 5.80 (d, J=5.4 Hz, 1H), 4.02 (s, 1H), 3.95 (dd, J=11.6, 7.6 Hz, 2H), 3.31 (d, J=13.6 Hz, 2H), 3.15 (d, J=16.4 Hz, 1H), 2.83 (d, J=16.4 Hz, 1H), 2.00 (tt, J=12.4, 6.4 Hz, 2H), 1.64 (d, J=13.2 Hz, 1H), 1.48 (dd, J=13.6, 6.4 Hz, 1H), 1.34-1.29 (m, 2H); LCMS: m/z 479.0 [M+H]$^+$.

Example 7: Synthesis of Compound 7

(S)-1'-(8-((2-amino-3-chloropyridin-4-yl)thio)-[1,2,4]triazol[4,3-c]pyrimidin-5-yl)-5,7-dihydrospiro[cyclopenta[c]pyridine-6,4'-piperidine]-7-amine

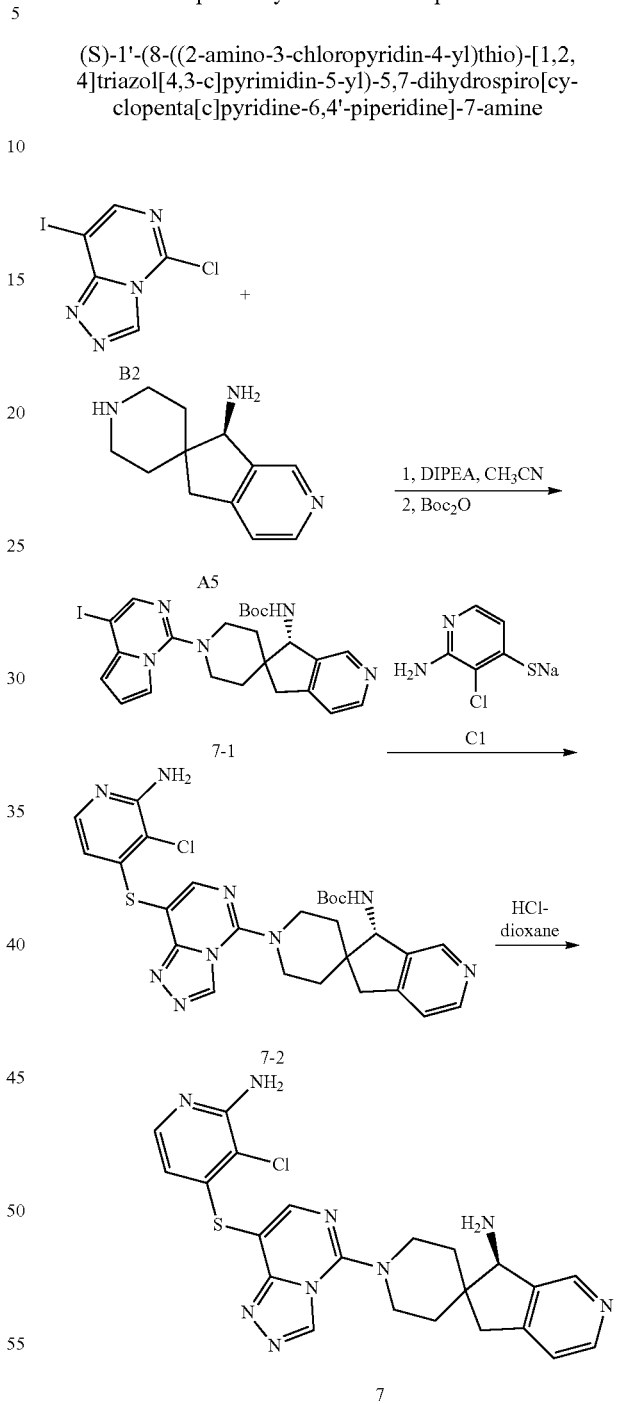

Compound 7 was synthesized through three steps according to the synthesis method of compound 6, using intermediate B2 instead of intermediate 6, and using intermediate A5 instead of intermediate A4.

$^1$H NMR (400 MHz, DMSO) δ 8.51 (s, 2H), 8.38 (d, J=4.8 Hz, 1H), 8.22 (s, 1H), 7.57 (d, J=5.6 Hz, 1H), 7.28 (d, J=4.8 Hz, 1H), 6.36 (s, 2H), 5.88 (d, J=5.6 Hz, 1H), 4.92 (t, J=13.6 Hz, 2H), 4.03 (s, 1H), 3.61 (dd, J=26.8, 12.0 Hz, 2H), 3.16

(d, J=16.8 Hz, 1H), 2.78 (s, 1H), 1.92 (td, J=11.2, 4.0 Hz, 2H), 1.63 (d, J=13.2 Hz, 1H), 1.33-1.24 (m, 1H).
LCMS: m/z 480.1 [M+H]⁺.

Example 8: Synthesis of Compound 8

(S)-1'-(8-((2-amino-3-chloropyridin-4-yl)thio)imidazo[1,2-c]pyrimidin-5-yl)-5,7-dihydrospiro[cyclopenta[c]pyridine-6,4'-piperidine]-7-amine

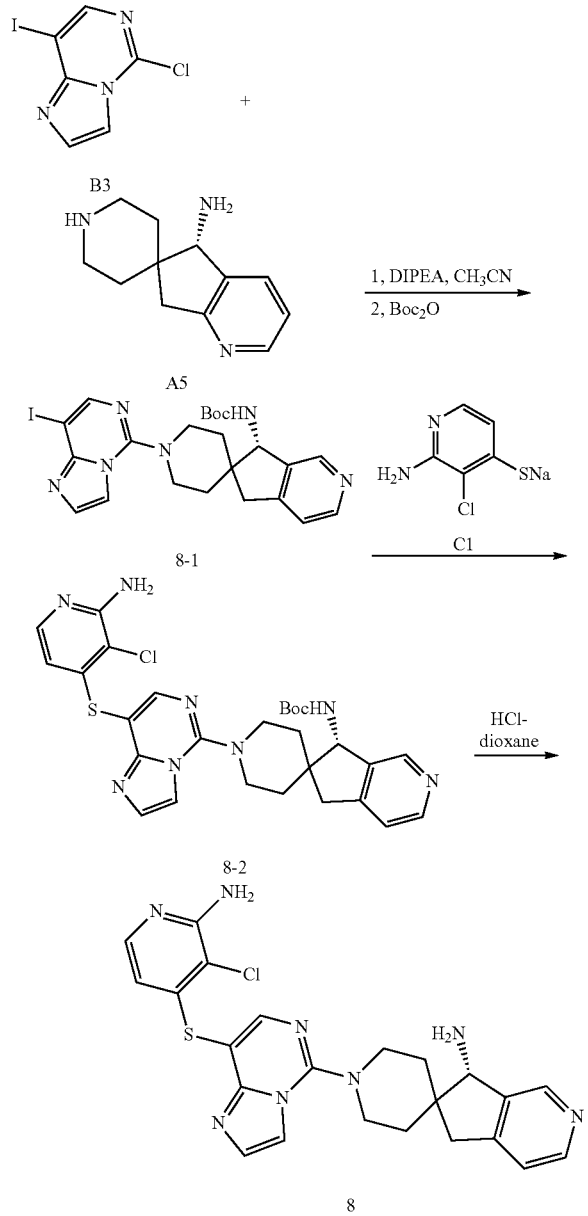

Compound 8 was synthesized according to the synthesis method of compound 6, using intermediate A5 instead of intermediate A4.

¹H NMR (400 MHz, DMSO) δ 8.53 (s, 1H), 8.39 (d, J=4.8 Hz, 1H), 8.04 (s, 1H), 7.84 (d, J=1.2 Hz, 1H), 7.58 (d, J=1.2 Hz, 1H), 7.56 (d, J=5.6 Hz, 1H), 7.28 (d, J=4.8 Hz, 1H), 6.34 (s, 2H), 5.80 (d, J=5.6 Hz, 1H), 4.07 (s, 1H), 3.93 (d, J=4.0 Hz, 2H), 3.37 (dd, J=19.6, 8.0 Hz, 2H), 3.13 (d, J=16.4 Hz, 1H), 2.76 (d, J=16.4 Hz, 1H), 1.98 (d, J=11.6 Hz, 2H), 1.62 (d, J=13.6 Hz, 1H), 1.30 (s, 1H).
LCMS: m/z 479.1 [M+H]⁺.

Example 9: Synthesis of Compound 9

(S)-1'-(8-(2,3-dichloropyridin-4-yl)thio-[1,2,4]-triazolo[4,3-c]pyrimidin-5-yl)-5,7-dihydrospiro[cyclopenta[b]pyridine-6,4'-piperidine]-7-amine

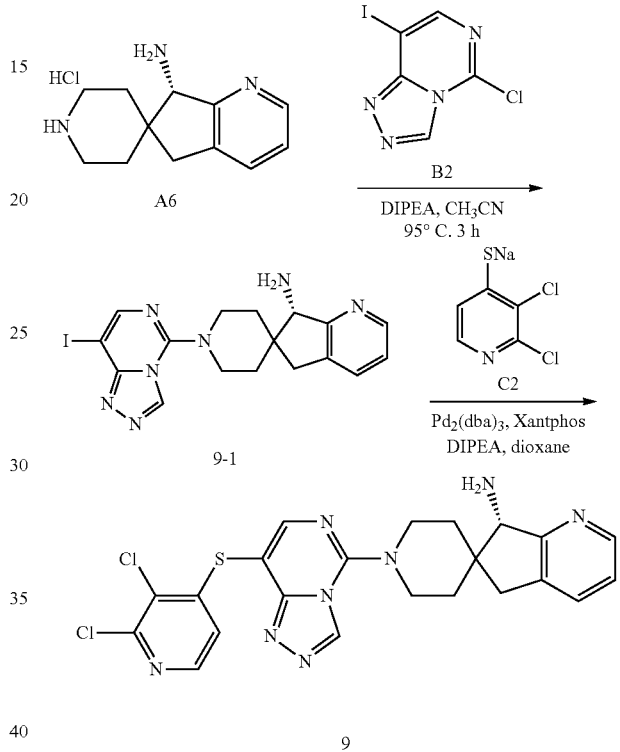

Step 1: (S)-5,7-dihydrospiro[cyclopenta[b]pyridine-6,4'-piperidine]-7-amine hydrochloride (A6, 200 mg, 1.28 mmol) was dissolved in acetonitrile (20 mL), DIPEA (1.6 mL, 9.68 mmol) and 5-chloro-8-iodo-[1,2,4]-triazolo[4,3-c]pyrimidine (B2, 180 mg, 0.64 mmol) were added, the mixture was heated to 90° C. and refluxed for 3 hours under the protection of nitrogen, and the reaction was completed. The reaction liquid was cooled to room temperature, poured into saturated sodium bicarbonate aqueous solution, and extracted twice with dichloromethane (80 mL). The organic phases were combined, and washed with saturated brine. The organic phase was separated, and then dried over anhydrous sodium sulfate, filtered and concentrated. The crude product was purified by silica gel chromatography (DCM:MeOH=20/1) to obtain (S)-1'-(8-iodo[1,2,4]triazolo[4,3-c]pyrimidin-5-yl)-5,7-dihydrospiro[cyclopenta[b]pyridine-6,4'-piperidine]-7-amine (9-1, 260 mg, yield 90%) as a light yellow solid. LCMS: m/z 448.2 [M+H]⁺

Step 2: (S)-1'-(8-iodo[1,2,4]triazolo[4,3-c]pyrimidin-5-yl)-5,7-dihydrospiro[cyclopenta[b]pyridine-6,4'-piperidine]-7-amine (21-1, 55 mg, 0.12 mmol) was dissolved in 1,4-dioxane (3 mL), and DIPEA (35 mg, 0.27 mmol) and sodium 2,3-dichloropyridine-4-mercaptan (C2, 100 mg, crude product) were added. XantPhos (30 mg, 0.05 mmol) and Pd₂(dba)₃ (17 mg, 0.02 mmol) were added under the protection of nitrogen. After the atmosphere in the reaction system was replaced with nitrogen three times, the mixture was reacted at 100° C. for 3 hours, and the reaction was completed. The reaction solution was concentrated and purified by high performance liquid chromatography to obtain (S)-1'-(8-(2,3-dichloropyridin-4-yl)thio-[1,2,4]-triazolo[4,3-c]pyrimidin-5-yl)-5,7-dihydrospiro[cyclopenta[b]pyridine-6,4'-piperidine]-7-amine (compound 9, 27 mg, TFA salt, yield: 40%) as a light yellow solid. LCMS: m/z 499.1 [M+H]+

$^1$H NMR (400 MHz, MeOD) δ 9.35 (s, 1H), 8.56 (d, J=4.8 Hz, 1H), 8.14 (s, 1H), 7.95 (d, J=5.2 Hz, 1H), 7.84 (d, J=7.6 Hz, 1H), 7.44-7.41 (m, 1H), 6.80 (d, J=5.2 Hz, 1H), 4.53 (s, 1H), 4.36-4.32 (m, 2H), 3.69-3.60 (m, 2H), 3.40 (d, J=16.4 Hz, 1H), 3.19 (d, J=16.4 Hz, 1H), 2.26-2.19 (m, 1H), 2.05-1.93 (m, 2H), 1.73-1.70 (m, 1H).

Example 10: Synthesis of Compound 10

(S)-1'-(8-((2-amino-3-chloropyridin-4-yl)thio)imidazo[1,2-c]pyrimidin-5-yl)-5,7-dihydrospiro[cyclopenta[b]pyridine-6,4'-piperidine]-7-amine

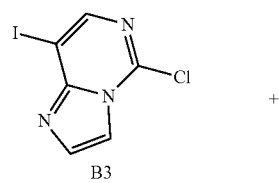

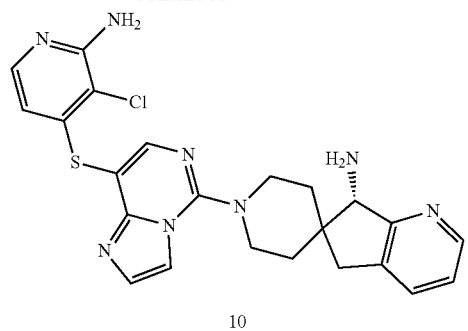

Compound 10 was synthesized through three steps according to the synthesis method of compound 6, using intermediate A6 instead of intermediate A4.

$^1$H NMR (400 MHz, DMSO) δ 8.38 (d, J=4.3 Hz, 1H), 8.24 (s, 1H), 8.03 (s, 1H), 7.84 (d, J=1.4 Hz, 1H), 7.65 (d, J=7.4 Hz, 1H), 7.56 (dd, J=9.1, 3.4 Hz, 2H), 7.29-7.13 (m, 1H), 6.33 (s, 2H), 5.80 (d, J=5.4 Hz, 1H), 4.01 (s, 1H), 3.95-3.86 (m, 2H), 3.38 (dd, J=23.6, 11.2 Hz, 3H), 3.11 (d, J=16.0 Hz, 1H), 2.75 (d, J=16.0 Hz, 1H), 2.05-1.91 (m, 2H), 1.69 (d, J=13.6 Hz, 1H), 1.31 (d, J=14.0 Hz, 2H).

LC-MS: m/z=478.0 [M+H+].

Example 11: Synthesis of Compound 11

(S)-1'-(8-((2-amino-3-chloropyridin-4-yl)thio)-[1,2,4]triazol[4,3-c]pyrimidin-5-yl)-5,7-dihydrospiro[cyclopenta[b]pyridine-6,4'-piperidine]-7-amine

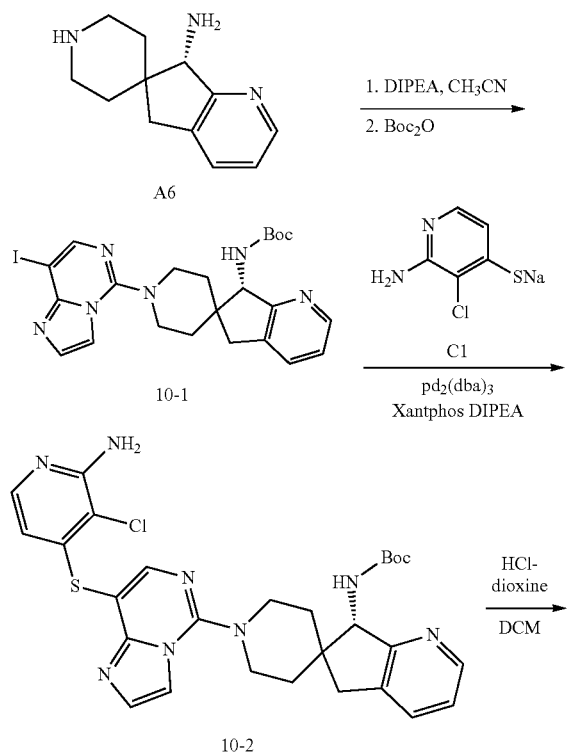

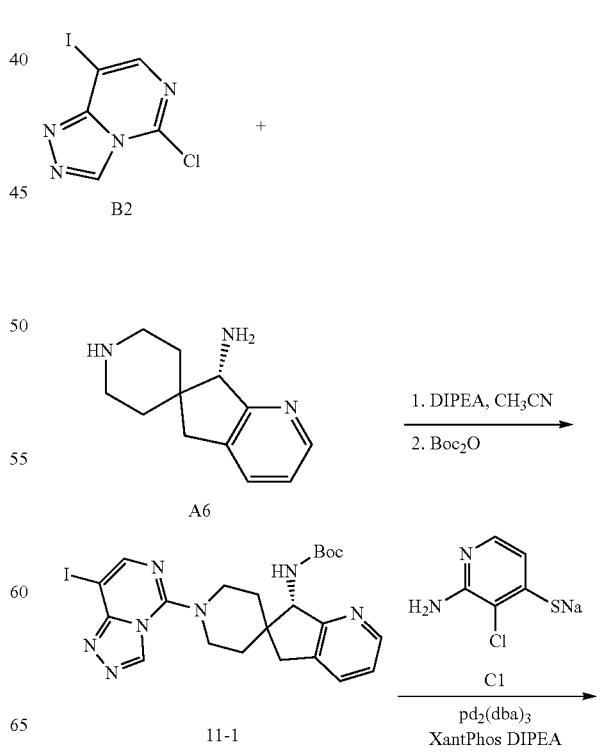

-continued

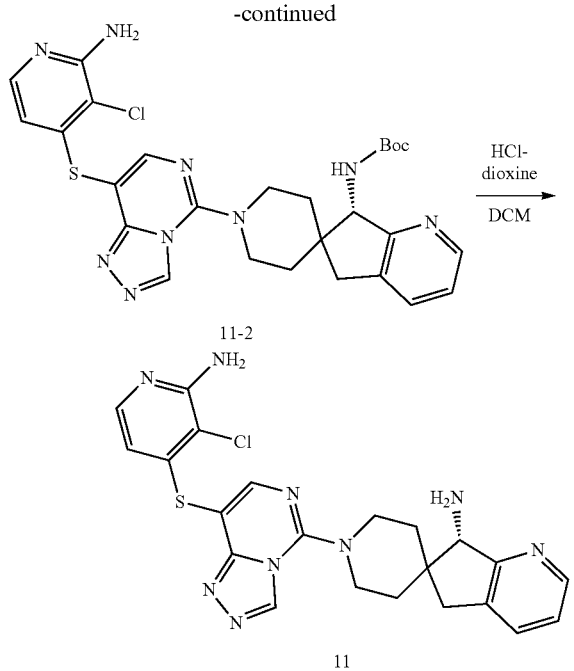

(S)-1'-(8-((2-amino-3-chloropyridin-4-yl)thio)-[1,2,4]triazolo[4,3-c]pyrimidin-5-yl)-5,7-dihydrospiro[cyclopenta[b]pyridine-6,4'-piperidine]-7-amine (11, formate, white solid) was synthesized through three steps according to the synthesis protocol of compound 6, using intermediate B2 instead of intermediate B3, and intermediate A6 instead of intermediate A4.

$^1$H NMR (400 MHz, DMSO-d6) δ 9.40 (s, 1H), 8.48 (d, J=4.5 Hz, 1H), 8.00 (s, 1H), 7.76 (d, J=7.3 Hz, 1H), 7.58 (d, J=5.4 Hz, 1H), 7.33 (dd, J=7.5, 5.0 Hz, 1H), 6.35 (s, 2H), 5.94 (d, J=5.4 Hz, 1H), 4.31 (s, 1H), 4.26-4.09 (m, 2H), 3.53 (dd, J=27.1, 12.0 Hz, 2H), 3.24 (d, J=16.4 Hz, 1H), 2.92 (d, J=16.3 Hz, 1H), 2.09 (s, 1H), 1.92 (s, 1H), 1.76 (d, J=13.2 Hz, 1H), 1.42 (d, J=13.2 Hz, 1H).

LCMS: m/z=479.0 [M+H+].

Example 12: Synthesis of Compound 12

(S)-1'-(8-((2-amino-3-chloropyridin-4-yl)thio)-[1,2,4]triazolo[4,3-c]pyrimidin-5-yl)-6-fluoro-1,3-dihydrospiro[indene-2,4'-piperidine]-1-amine

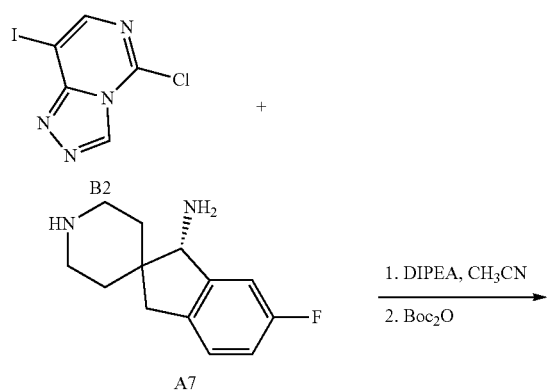

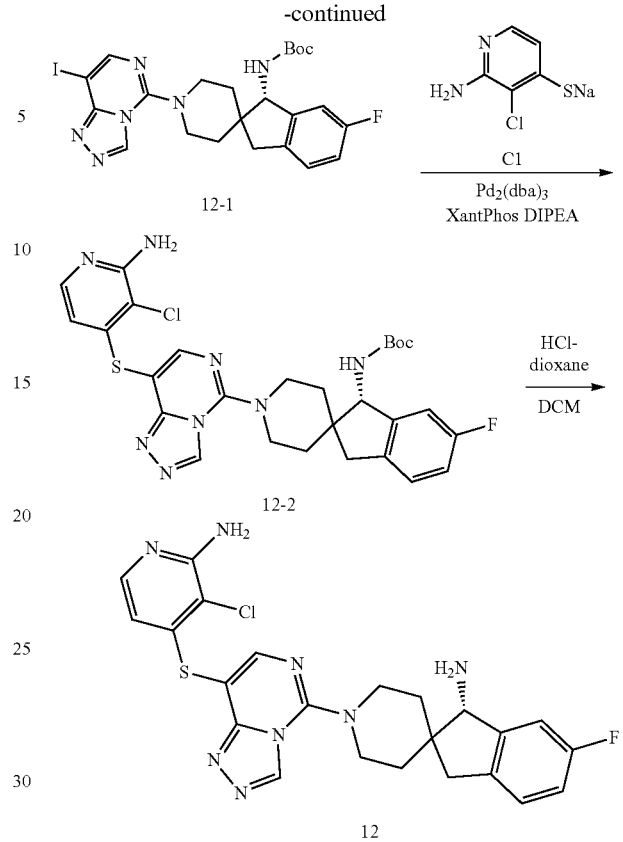

(S)-1'-(8-((2-amino-3-chloropyridin-4-yl)thio)-[1,2,4]triazolo[4,3-c]pyrimidin-5-yl)-6-fluoro-1,3-dihydrospiro[indene-2,4'-piperidine]-1-amine (12, formate, white solid) was synthesized through three steps according to the synthesis protocol of compound 6, using intermediate B2 instead of intermediate B3, and intermediate A7 instead of intermediate A4.

$^1$H NMR (400 MHz, DMSO-d6) δ 9.38 (s, 1H), 8.22 (s, 1H), 7.98 (s, 1H), 7.57 (d, J=5.4 Hz, 1H), 7.31-7.20 (m, 1H), 7.16 (d, J=7.5 Hz, 1H), 7.01 (t, J=8.7 Hz, 1H), 6.34 (s, 2H), 5.95 (d, J=5.4 Hz, 1H), 4.14 (t, J=12.0 Hz, 2H), 4.00 (s, 1H), 3.47 (dd, J=25.4, 12.0 Hz, 3H), 3.10 (d, J=15.5 Hz, 1H), 2.71 (d, J=15.5 Hz, 1H), 2.08-1.85 (m, 2H), 1.64 (d, J=13.3 Hz, 1H), 1.30 (d, J=13.5 Hz, 1H). LCMS: m/z=495.0 [M+H+].

Example 13: Synthesis of Compound 13

(S)-1'-(8-((2-amino-3-chloropyridin-4-yl)thio)imidazo[1,2-c]pyrimidin-5-yl)-6-fluoro-1,3-dihydrospiro[indene-2,4'-piperidine]-1-amine

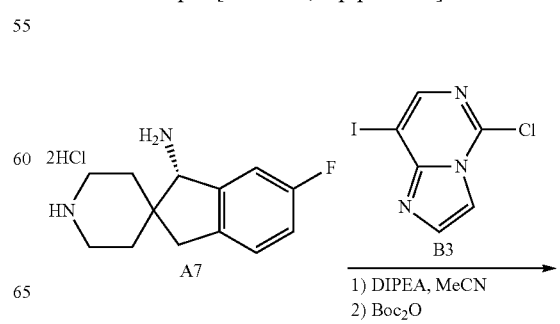

77

-continued

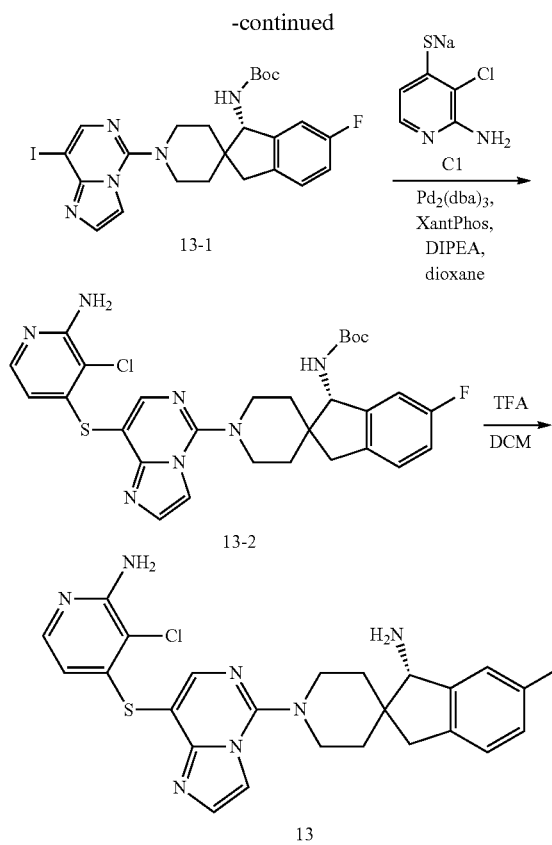

(S)-(1'-(8-((2-amino-3-chloropyridin-4-yl)thio)imidazo[1,2-c]pyrimidin-5-yl)-5-fluoro-1,3-dihydrospiro[indene-2,4'-piperidin]-3-yl)carboxylic acid tert-butyl ester (13-2) was synthesized through two steps according to the synthesis protocol of compound 6, using intermediate A7 instead of intermediate A4.

Step 3: (S)-(1'-(8-((2-amino-3-chloropyridin-4-yl)thio)imidazo[1,2-c]pyrimidin-5-yl)-5-fluoro-1,3-dihydrospiro[indene-2,4'-piperidin]-3-yl)carboxylic acid tert-butyl ester (13-2, 60 mg, 0.101 mmol), dichloromethane (1 mL) and trifluoroacetic acid (0.2 mL) were added to a dry single-necked flask successively. The reaction solution was stirred at 20° C. for 1 hour. The reaction liquid was concentrated under reduced pressure. The pH of the obtained residual reaction liquid was adjusted to 8 with saturated sodium bicarbonate aqueous solution. The mixture was extracted with DCM/MeOH (10:1) mixed solvent (10 mL) for three times, and the combined organic phase was concentrated under reduced pressure. The obtained residue was purified by HPLC preparation to obtained (S)-1'-(8-((2-amino-3-chloropyridin-4-yl)thio)imidazo[1,2-c]pyrimidin-5-yl)-6-fluoro-1,3-dihydrospiro[indene-2,4'-piperidine]-1-amine (13, 32 mg, formate, yield: 58.2%) as a white solid.

$^{1}$H NMR (400 MHz, DMSO-d6) δ 8.15 (s, 1H), 8.03 (s, 1H), 7.83 (d, J=1.2 Hz, 1H), 7.58 (d, J=1.6 Hz, 1H), 7.55 (d, J=5.6 Hz, 1H), 7.32-7.26 (m, 1H), 7.23-7.18 (m, 1H), 7.12-7.02 (m, 1H), 6.32 (s, 2H), 5.80 (d, J=5.2 Hz, 1H), 4.14 (s, 1H), 4.00-3.90 (m, 2H), 3.40-3.30 (m, 2H), 3.15-3.05 (m, 1H), 2.85-2.75 (m, 1H), 2.05-1.85 (m, 2H), 1.70-1.55 (m, 1H), 1.45-1.36 (m, 1H); LC-MS: m/z 496.0 [M+H]+.

78

Example 14: Synthesis of Compound 14

(S)-1'-(8-((2-amino-3-chloropyridin-4-yl)thio)imidazo[1,2-c]pyrimidin-5-yl)-5,7-dihydrospiro[cyclopenta[c]pyridine-6,4'-piperidine]-5-amine

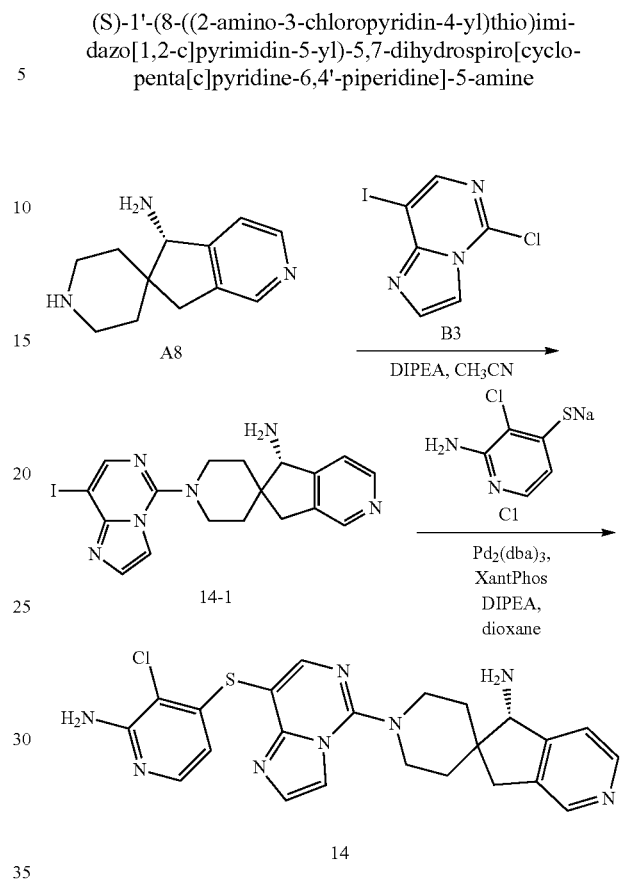

Step 1: (S)-5,7-dihydrospiro[cyclopenta[c]pyridine-6,4'-piperidine]-5-amine hydrochloride (A8, 200 mg, 0.83 mmol) was dissolved in acetonitrile (20 mL), DIPEA (1.07 g, 8.3 mmol) and 5-chloro-8-iodoimidazo[1,2-c]pyrimidine (B3, 208 mg, 0.75 mmol) were added, the mixture was heated to 90° C. and refluxed for 5 hours under nitrogen protection, and the reaction was completed. The reaction liquid was cooled to room temperature, poured into saturated sodium bicarbonate aqueous solution, and extracted twice with dichloromethane (50 mL). The organic phases were combined and then washed with saturated brine. The organic phase was separated, and then dried over anhydrous sodium sulfate, filtered and concentrated. The crude product was purified by silica gel chromatography to obtain 1-(8-iodoimidazo[1,2-c]pyrimidin-5-yl)-5,7-dihydrospiro[cyclopenta[c]pyridine-6,4'-piperidine]-4-amine (14-1, 250 mg, yield: 74%) as a light yellow solid. LCMS: m/z 447.1 [M+H]$^{+}$ Step 9: 1'-(8-iodoimidazo[1,2-c]pyrimidin-5-yl)-5,7-dihydrospiro[cyclopenta[c]pyridine-6,4'-piperidine]-4-amine (14-1, 50 mg, 0.11 mmol) was dissolved in 1,4-dioxane (10 mL), DIPEA (36 mg, 0.28 mmol) and sodium 2-amino-3-chloropyridine-4-mercaptan (C1, 31 mg, 0.17 mmol) were added. XantPhos (13 mg, 0.02 mmol) and Pd$_2$(dba)$_3$ (10 mg, 0.01 mmol) were added under the protection of nitrogen. After the atmosphere in the reaction system was replaced with nitrogen for three times, the mixture was reacted at 100° C. for 3 hours, and the reaction was completed. The reaction liquid was concentrated, and then purified by high performance liquid chromatography to obtain (S)-1'-(8-((2-amino-3-chloropyridin-4-yl)thio)imidazo[1,2-c]pyrimidin- 5-yl)-5,7-dihydrospiro[cyclopenta[c]pyridine-6,4'-piperidine]-5-amine (14, 12 mg, yield: 22.4%) as a light yellow solid.

LCMS: m/z 479.2 [M+H]$^+$

1H NMR (400 MHz, MeOD) δ 8.64 (s, 1H), 8.56 (d, J=4.4 Hz, 1H), 8.09 (s, 1H), 7.62-7.60 (m, 2H), 7.60-7.50 (m, 1H), 5.95-5.94 (m, 1H), 4.64 (s, 1H), 4.22-4.07 (m, 2H), 3.60 (s, 2H), 3.6-3.49 (m, 2H), 2.20-2.10 (m, 2H), 2.10-2.00 (m, 1H), 1.85-1.63 (m, 2H).

Example 15: Synthesis of Compound 15

(S)-1'-(8-((2-amino-3-chloropyridin-4-yl)thio)-[1,2,4]triazolo[4,3-c]pyrimidin-5-yl)-5,7-dihydrospiro[cyclopenta[c]pyridine-6,4'-piperidine]-5-amine

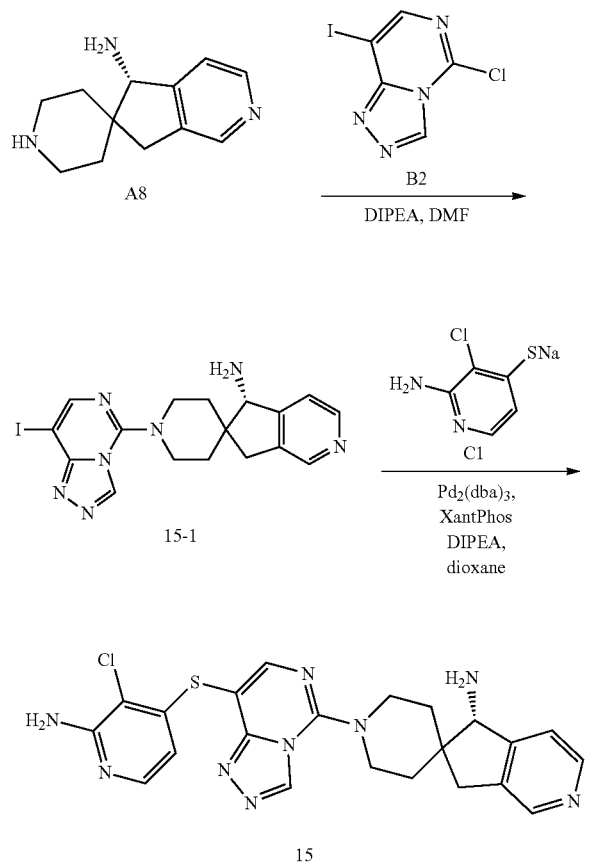

(S)-1'-(8-((2-amino-3-chloropyridin-4-yl)thio)-[1,2,4]triazolo[4,3-c]pyrimidin-5-yl)-5,7-dihydrospiro[cyclopenta[c]pyridine-6,4'-piperidine]-5-amine (15) was synthesized through two steps according to the synthesis protocol of compound 14, using intermediate B2 instead of intermediate B3.

LCMS: m/z 480.0 [M+H]$^+$ $^1$H NMR (400 MHz, MeOD) δ 9.31 (s, 1H), 8.43-8.46 (m, 2H), 8.02 (s, 1H), 7.49-7.54 (m, 2H), 6.05 (d, J=5.6 MHz, 1H), 4.17-4.29 (m, 3H), 3.48-3.60 (m, 3H), 2.96 (d, J=16.0 MHz, 1H), 1.98-2.15 (m, 2H), 1.76-1.79 (m, 1H), 1.22-1.25 (m, 1H).

Example 16: Synthesis of Compound 16

(S)-1-amino-1'-(8-((2-amino-3-chloropyridin-4-yl)thio)-[1,2,4]triazolo[4,3-c]pyrimidin-5-yl)-1,3-dihydrospiro[indene-2,4'-piperidin]-4-ol

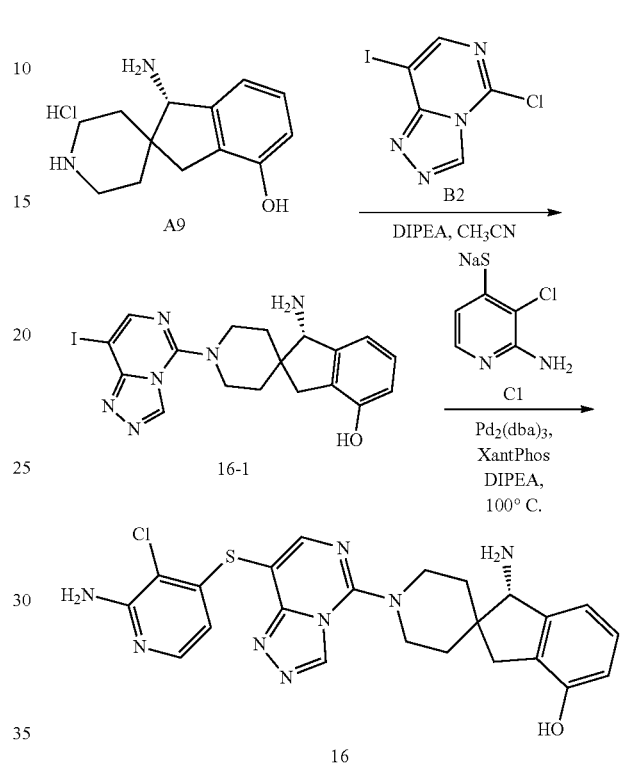

Step 1: (S)-1-amino-1,3-dihydrospiro[indene-2,4'-piperidin]-4-ol hydrochloride (A9, 200 mg, 0.79 mmol) was dissolved in acetonitrile (40 mL), DIPEA (1.07 g, 8.3 mmol) and 5-chloro-8-iodo-[1,2,4]triazolo[4,3-c]pyrimidine (B2, 208 mg, 0.75 mmol) were added, the mixture was reacted at room temperature under nitrogen protection for 18 hours, and the reaction was completed. The reaction liquid was cooled to room temperature, poured into saturated sodium bicarbonate aqueous solution, and extract with dichloromethane (100 mL) twice. The organic phases were combined, and then washed with saturated brine. The organic phase was separated, and then dried over anhydrous sodium sulfate, filtered and concentrated. The crude product was purified by silica gel chromatography to obtain (S)-1-amino-1'-(8-iodo-[1,2,4]triazolo[4,3-c]pyrimidin-5-yl)-1,3-dihydrospiro[indene-2,4'-piperidin]-4-ol (16-1, 220 mg, yield: 63%) as a light yellow solid. LCMS: m/z 463.0 [M+H]$^+$ Step 2: (S)-1-amino-1'-(8-iodo-[1,2,4]triazolo[4,3-c]pyrimidin-5-yl)-1,3-dihydrospiro[indene-2,4'-piperidin]-4-ol (16-1, 200 mg, 0.43 mmol) was dissolved in 1,4-dioxane (30 mL), and DIPEA (111 mg, 0.86 mmol) and sodium 2-amino-3-chloropyridin-4-mercaptan (C1, 118 mg, 0.65 mmol) were added. Under nitrogen protection, XantPhos (52.0 mg, 0.08 mmol) and Pd$_2$(dba)$_3$ (41 mg, 0.04 mmol) were added. After the atmosphere in the reaction system was replaced with nitrogen for three times, the mixture was reacted at 100° C. for 3 hours, and the reaction was completed. The reaction liquid was concentrated and then purified by high performance liquid chromatography to obtain (S)-1-amino-1'-(8-

((2-amino-3-chloropyridin-4-yl)thio)-[1,2,4]triazolo[4,3-c]pyrimidin-5-yl)-1,3-dihydrospiro[indene-2,4'-piperidin]-4-ol (16,100 mg, yield: 47%) as a white solid. LCMS: m/z 495.3 [M+H]$^+$ $^1$H NMR (400 MHz, MeOD) δ 9.32 (s, 1H), 8.01 (s, 1H), 7.53 (d, J=5.6 MHz, 1H), 7.04 (t, J=7.6 MHz, 1H), 6.84 (d, J=5.6 MHz, 1H), 6.64 (d, J=8.0 MHz, 1H), 6.06 (d, J=5.6 MHz, 1H), 4.20-4.24 (m, 2H), 3.95 (s, 1H), 3.54-3.62 (m, 2H), 3.13 (d, J=15.6 MHz, 1H), 2.74 (d, J=15.6 MHz, 1H), 1.93-2.06 (m, 2H), 1.70 (d, J=12.8 MHz, 1H), 1.55 (d, J=12.8 MHz, 1H).

Example 17: Synthesis of Compound 17

Compound (S)-1-amino-1'-(8-((2-amino-3-chloropyridin-4-yl)thio)-[1,2,4]triazolo[4,3-c]pyrimidin-5-yl)-1,3-dihydrospiro[indene-2,4'-piperidine]-4-nitrile

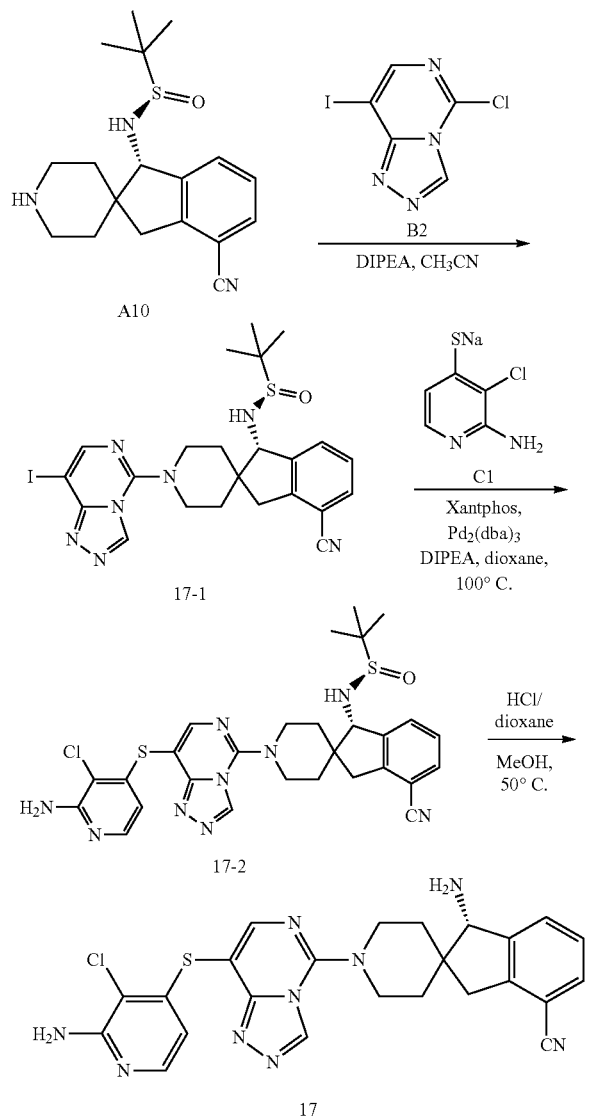

Step 1: (S)-1-(((R)-tert-butylsulfinyl)amino)-4-cyano-1,3-dihydrospiro[indene-2,4'-piperidine] (A10, 490 mg, 1.48 mmol) was dissolved in acetonitrile (20 mL), DIPEA (1.91 g, 14.8 mmol) and 5-chloro-8-iodo-[1,2,4]triazolo[4,3-c]pyrimidine (B2, 415 mg, 1.48 mmol) were added, the mixture was reacted at 85° C. under nitrogen protection for 3 hours, and the reaction was completed. The residue obtained by concentration under reduced pressure was purified by silica gel chromatography (0-10% gradient of methanol/ethyl acetate) to obtain (R)—N—((S)-1'-(8-iodo-[1,2,4]triazolo[4,3-c]pyrimidin-5-yl)-4-cyano-1,3-dihydrospiro[indene-2,4'-piperidin]-1-yl)-2-tert-butylsulfonamide (17-1, 360 mg, yield: 42.3%) as a yellow solid. LCMS: m/z 576.1 [M+H]$^+$.

Step 2: (R)—N—((S)-1'-(8-iodo-[1,2,4]triazolo[4,3-c]pyrimidin-5-yl)-4-cyano-1,3-dihydrospiro[indene-2,4'-piperidin]-1-yl)-2-tert-butylsulfonamide (17-1, 360 mg, 0.63 mmol) was dissolved in 1,4-dioxane (10 mL), and DIPEA (202 mg, 1.56 mmol) and sodium 2-amino-3-chloropyridin-4-mercaptan (C1, 171 mg, 0.94 mmol) were added. XantPhos (73 mg, 0.126 mmol) and Pd$_2$(dba)$_3$ (57.7 mg, 0.063 mmol) were added under the protection of nitrogen. After the atmosphere in the reaction system was replaced with nitrogen for three times, the mixture was reacted at 100° C. for 3 hours, and the reaction was completed. The reaction solution was concentrated and then purified by silica gel chromatography to to obtain (R)—N—((S)-1'-((8-((2-amino-3-chloropyridin-4-yl)thio)-[1,2,4]triazolo[4,3-c]pyrimidin-5-yl)-4-cyano-1,3-dihydrospiro[indene-2,4'-piperidin]-1-yl)-2-tert-butylsulfonamide (17-2, 130 mg, 34.2%) as a white solid. LC-MS: m/z 608.2 [M+H]$^+$.

Step 3: (R)—N—((S)-1'-((8-((2-amino-3-chloropyridin-4-yl)thio)-[1,2,4]triazolo[4,3-c]pyrimidin-5-yl)-4-cyano-1,3-dihydrospiro[indene-2,4'-piperidin]-1-yl)-2-tert-butylsulfonamide (17-2, 130 mg, 0.21 mmol) and methanol (6 mL) were successively added to a 50 mL single-necked flask under the protection of nitrogen, and hydrochloric acid 1,4-dioxane solution (2 ml, 4M) was added dropwise at room temperature, and the mixture was stirred at room temperature for 1 hour. After the reaction was completed, the mixture was cooled to room temperature, filtered and concentrated under reduced pressure. The obtained residue was purified by high performance liquid chromatography to obtain (S)-1-amino-1'-(8-((2-amino-3-chloropyridin-4-yl)thio)-[1,2,4]triazolo[4,3-c]pyrimidin-5-yl)-1,3-dihydrospiro[indene-2,4'-piperidine]-4-nitrile (17, 10 mg, yield: 9.3%).

$^1$H NMR (400 MHz, CDCl$_3$) δ 9.32 (s, 1H), 8.02 (s, 1H), 7.71 (d, J=7.2 Hz, 1H), 7.59 (d, J=7.6 Hz, 1H), 7.53 (d, J=5.6 Hz, 1H), 7.43 (d, J=7.6 Hz, 1H), 6.06 (d, J=5.6 Hz, 1H), 4.23 (d, J=10.8 Hz, 2H), 4.12 (s, 1H), 3.60 (m, 2H), 3.37 (m, 1H), 3.03 (d, J=16.4 Hz, 1H), 2.06 (m, 2H), 1.74 (t, 2H), 1.57 (d, J=19.2 Hz, 2H), 1.52 (s, 2H).

LCMS: m/z 504.1 [M+H]$^+$.

Example 18: Synthesis of Compound 18

(S)-1'-(8-((2-amino-3-chloropyridin-4-yl)thio)imidazo[1,2-c]pyrimidin-5-yl)-5,7-dihydrospiro[cyclopenta[b]pyrazine-6,4'-piperidine]-5-amine

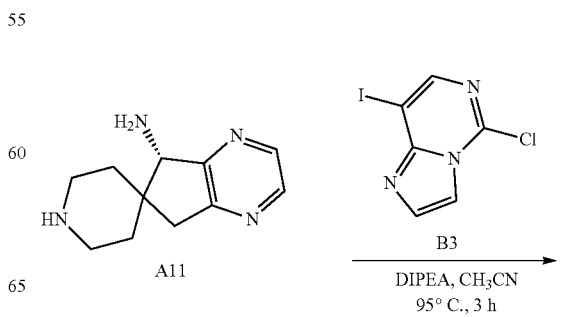

83

-continued

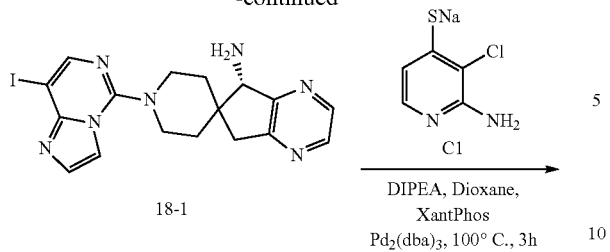

18-1

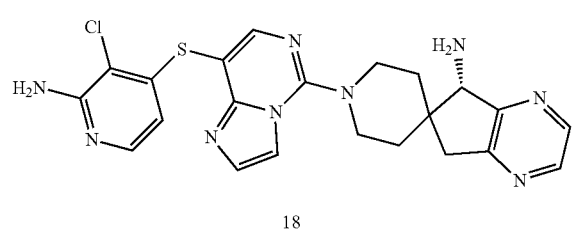

18

Step 1: (S)-5,7-dihydrospiro[cyclopenta[b]pyridine-6,4'-piperidine]-5-amine hydrochloride (A11, 1.50 g, 4.95 mmol) was dissolved in 150 mL of acetonitrile, DIPEA (5.68 g, 44.0 mmol) and 5-chloro-8-iodoimidazo[1,2-c]pyrimidine (B3, 1.28 g, 4.59 mmol) were added, the mixture was heated to 95° C. for and refluxed for 3 hours under nitrogen protection, and the reaction was completed. The mixture was cooled to room temperature and filtered. The filtrate was concentrated to dry, mixed with silica gel and passed through the column to obtain (S)-1'-(8-iodoimidazo[1,2-c]pyrimidine-5-yl)-5,7-dihydrospiro[cyclopenta[b]pyrazine-6,4'-piperidine]-5-amine (18-1, 2.05 g, yield: 92.7%) as a beige powder. LCMS: m/z 448.0 [M+H]$^+$ Step 2: (S)-1'-(8-iodoimidazo[1,2-c]pyrimidin-5-yl)-5,7-dihydrospiro[cyclopenta[b]pyrazine-6,4'-piperidine]-5-amine (18-1, 2.05 g, 4.59 mmol) was dissolved in 120 mL of 1,4-dioxane in a 350 mL glass seal tube, DIPEA (1.78 g, 13.8 mmol), sodium 2-amino-3-chloropyridine-4-mercaptan (C1, 1.26 g, 6.9 mmol), XantPhos (797 mg, 1.38 mmol) and Pd$_2$(dba)$_3$ (630 mg, 0.69 mmol) were added successively, the reaction mixture was sparged with argon for 30 seconds, and was heated to 100° C. under argon and maintained for 3 hours until the reaction was completed. The mixture was cooled to room temperature, diluted with dichloromethane and filtered by suction filtration. The filtrate was spin-dried and passed through the column. The obtained pure point was spin-dried, mixed with dichloromethane/n-hexane (1/1) and pulped overnight, and then filtered and dried to obtain (S)-1'-(8-((2-amino-3-chloropyridin-4-yl)thio)imidazo[1,2-c]pyrimidin-5-yl)-5,7-dihydrospiro[cyclopenta[b]pyrazine-6,4'-piperidine]-5-amine (compound 18, 440 mg, yield: 19.9%). LCMS: m/z 480.1 [M+H]$^+$ $^1$H NMR (400 MHz, MeOD): δ8.44-8.39 (m, 2H), 8.05 (s, 1H), 7.85 (d, J=1.6 Hz, 1H), 7.56 (d, J=1.6 Hz, 1H), 7.49 (d, J=5.6 Hz, 1H), 5.89 (d, J=5.6 Hz, 1H), 4.14 (s, 1H), 4.06-4.02 (m, 2H), 3.49-3.40 (m, 2H), 3.33 (s, 1H), 3.01 (d, J=16.8 Hz, 1H), 2.24-2.10 (m, 2H), 1.82 (d, J=13.2 Hz, 1H), 1.50 (d, J=13.6 Hz, 1H).

84

Example 19: Synthesis of Compound 19

(S)-1'-(8-((2-amino-3-chloropyridin-4-yl)thio)-[1,2,4]triazolo[4,3-c]pyrimidin-5-yl)-4-methoxy-1,3-dihydrospiro[indene-2,4'-piperidine]-1-amine

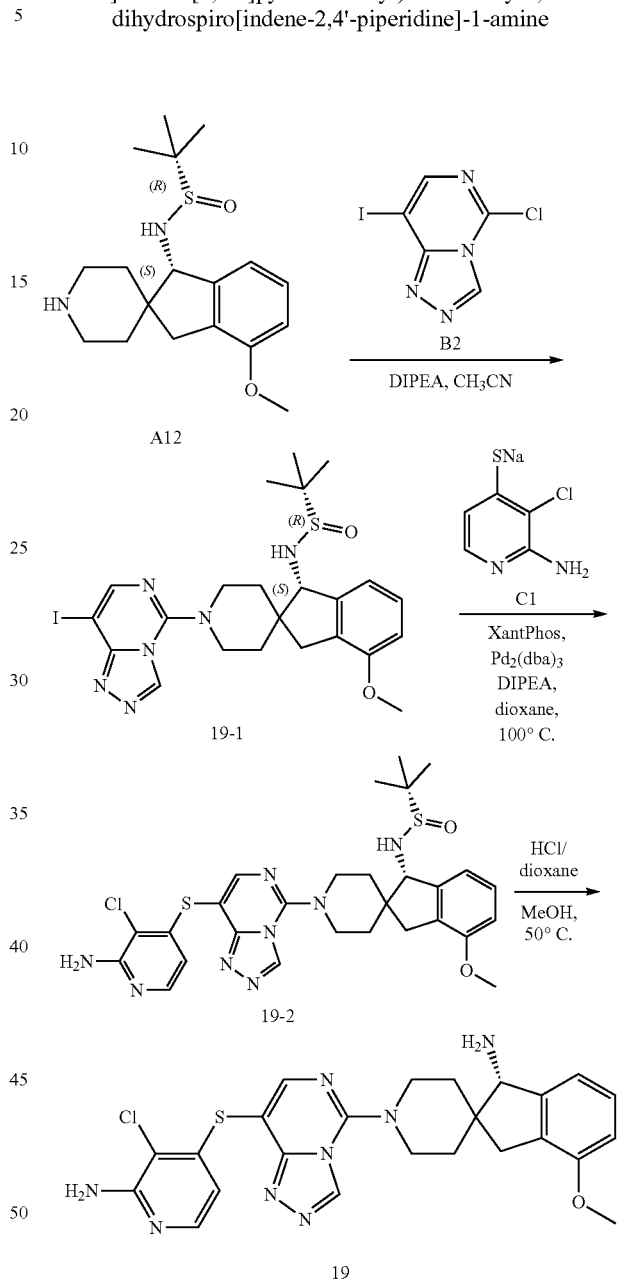

Step 7: (S)-1-(((R)-tert-butylsulfinyl)amino)-4-methoxy-1,3-dihydrospiro[indene-2,4'-piperidine] (A12, 520 mg, 1.55 mmol) was dissolved in acetonitrile (20 mL), DIPEA (2.0 g, 15.5 mmol) and 5-chloro-8-iodo-[1,2,4]triazolo[4,3-c]pyrimidine (B2, 435 mg, 1.55 mmol) were added, the mixture was reacted at 85° C. for 3 hours under the protection of nitrogen, and the reaction was completed. The residue obtained by concentration under reduced pressure was purified by silica gel chromatography (0-10% gradient of methanol/ethyl acetate) to obtain (R)—N—((S)-1'-(8-iodo-[1,2,4]triazolo[4,3-c]pyrimidine-5-yl)-4-methoxy-1,3-dihydrospiro[indene-2,4'-piperidin]-1-yl)-2-tert-butylsulfonamide (19-1, 420 mg, yield: 46.8%) as a yellow solid.

LCMS: m/z 581.1 [M+H]+.

Step 8: (R)—N—((S)-1'-(8-iodo-[1,2,4]triazolo[4,3-c]pyrimidin-5-yl)-4-methoxy-1,3-dihydrospiro[indene-2,4'-piperidin]-1-yl)-2-tert-butylsulfonamide (19-1, 420 mg, 0.72 mmol) was dissolved in 1,4-dioxane (10 mL), and DIPEA (234 mg, 1.81 mmol) and sodium 2-amino-3-chloropyridine-4-mercaptan (C1, 198 mg, 1.09 mmol) were added. XantPhos (83 mg, 0.144 mmol) and Pd$_2$(dba)$_3$ (66 mg, 0.072 mmol) were added under the protection of nitrogen. After the atmosphere in the reaction system was replaced with nitrogen for three times, the mixture was reacted at 100° C. for 3 hours, and the reaction was completed. The reaction solution was concentrated and then purified by silica gel chromatography to obtain (R)—N—((S)-1'-(8-((2-amino-3-chloropyridin-4-yl)thio)-[1,2,4]triazolo[4,3-c]pyrimidin-5-yl)-4-methoxy-1,3-dihydrospiro[indene-2,4'-piperidin]-1-yl)-2-tert-butylsulfonamide (19-2, 310 mg, yield: 69.9%) as a white solid.

LCMS: m/z 613.2 [M+H]+.

Step 9: (R)—N—((S)-1'-(8-((2-amino-3-chloropyridin-4-yl)thio)-[1,2,4]triazolo[4,3-c]pyrimidin-5-yl)-4-methoxy-1,3-dihydrospiro[indene-2,4'-piperidin]-1-yl)-2-tert-butylsulfonamide (19-2, 310 mg, 0.51 mmol) and methanol (6 mL) were added to a 50 mL single-necked flask under the protection of nitrogen successively, hydrochloric acid 1,4-dioxane solution (2 mL, 4M) was added dropwise at room temperature, and the mixture was stirred at room temperature for 1 hour. After the reaction was completed, the mixture was cooled to room temperature, filtered and concentrated under reduced pressure. The obtained residue was purified by preparative high performance liquid chromatography to obtain (S)-1'-(8-((2-amino-3-chloropyridin-4-yl)thio)-[1,2,4]triazolo[4,3-c]pyrimidin-5-yl)-4-methoxy-1,3-dihydrospiro[indene-2,4'-piperidine]-1-amine (compound 19, 114 mg, yield: 44.3%).

$^1$H NMR (400 MHz, CDCl$_3$) δ 8.80 (s, 1H), 7.95 (s, 1H), 7.65 (d, J=5.6 Hz, 1H), 7.26 (t, 2H), 6.96 (d, J=7.6 Hz, 1H), 6.77 (d, J=8.4 Hz, 1H), 6.02 (d, J=5.6 Hz, 1H), 4.89 (s, 2H), 4.13-4.04 (m, 4H), 3.86 (s, 3H), 3.53-3.48 (m, 2H), 3.11 (d, J=16 Hz, 1H), 2.70 (d, J=16 Hz, 1H), 2.08-2.01 (m, 3H), 1.76 (d, J=14 Hz, 1H), 1.53 (d, J=14 Hz, 2H).

LCMS: m/z 509.2 [M+H]+.

Example 20: Synthesis of Compound 20

(S)-1'-(8-((2-amino-3-chloropyridin-4-yl)thio)-[1,2,4]triazol[4,3-c]pyrimidin-5-yl)-5,7-dihydrospiro[cyclopenta[b]pyrazine-6,4'-piperidine]-5-amine

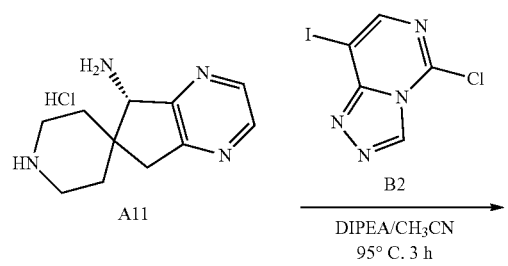

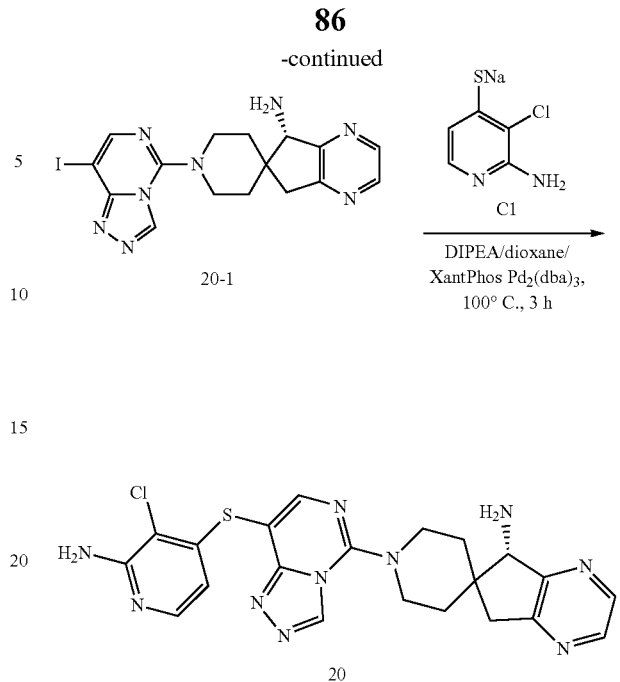

Step 1: (S)-5,7-dihydrospiro[cyclopenta[b]pyridine-6,4'-piperidine]-5-amine hydrochloride (A11, 89 mg, 0.29 mmol) was dissolved in 20 mL of acetonitrile, DIPEA (212 mg, 1.64 mmol) and 5-chloro-8-iodo-[1,2,4]triazolo[4,3-c]pyrimidine (B2, 77 mg, 0.275 mmol) were added, the mixture was heated to 95° C. and refluxed for 3 hours under the protection nitrogen, and the reaction was completed. The mixture was cooled to room temperature and filtered. The filtrate was concentrated to dry, mixed with silica gel and passed through the column to obtain (S)-1'-(8-iodo-[1,2,4]triazolo[4,3-c]pyrimidin-5-yl)-5,7-dihydrospiro[cyclopenta[b]pyrazine-6,4'-piperidine]-5-amine (20-1, 65 mg, yield: 52.7%). LCMS: m/z 449.2 [M+H]+

Step 2: (S)-1'-(8-iodo-[1,2,4]triazolo[4,3-c]pyrimidin-5-yl)-5,7-dihydrospiro[cyclopenta[b]pyrazine-6,4'-piperidine]-5-amine (20-1, 65 mg, 0.145 mmol) was dissolved in 5 mL of 1,4-dioxanein a 5 mL microwave tube, and DIPEA (56 mg, 0.434 mmol), 2-amino-3-chloropyridine-4 sodium sulfide (C1, 40 mg, 0.219 mmol), XantPhos (34 mg, 0.059 mmol) and Pd$_2$(dba)$_3$ (27 mg, 0.029 mmol) were added successively, the reaction mixture was sparged with argon for 30 seconds, and was heated to 100° C. under the atmosphere of argon and maintained for 3 hours until the reaction was completed. The mixture was cooled to room temperature, diluted with dichloromethane, and filtered by suction filtration. The filtrate was spin-dried and purified with preparative silica gel board. The obtained pure point was sent for preparation to obtain a pure product of (S)-1'-(8-((2-amino-3-chloropyridin-4-yl)thio)-[1,2,4]triazolo[4,3-c]pyrimidin-5-yl)-5,7-dihydrospiro[cyclopenta[b]pyrazine-6,4'-piperidine]-5-amine (compound 20, 19.4 mg, yield: 27.8%). LCMS: m/z 481.2 [M+H]+

$^1$H NMR (400 MHz, MeOD) δ9.35 (s, 1H), 8.59-8.57 (m, 2H), 8.11 (s, 1H), 7.53 (d, J=6.8 Hz, 1H), 6.37 (d, J=6.4 Hz, 1H), 4.65 (s, 2H), 4.37-4.35 (m, 2H), 3.69-3.62 (m, 2H), 3.47 (d, J=17.2 Hz, 1H), 3.26 (s, 1H), 2.31-2.23 (m, 1H), 2.07-1.97 (m, 2H), 1.68 (d, J=11.6 Hz, 1H).

Example 21: Synthesis of Compound 21

(S)-1'-(8-((2-(trifluoromethyl)pyridin-3-yl)thio)-[1,2,4]-triazolo[4,3-c]pyrimidin-5-yl)-5,7-dihydrospiro[cyclopenta[b]pyridine-6,4'-piperidine]-7-amine

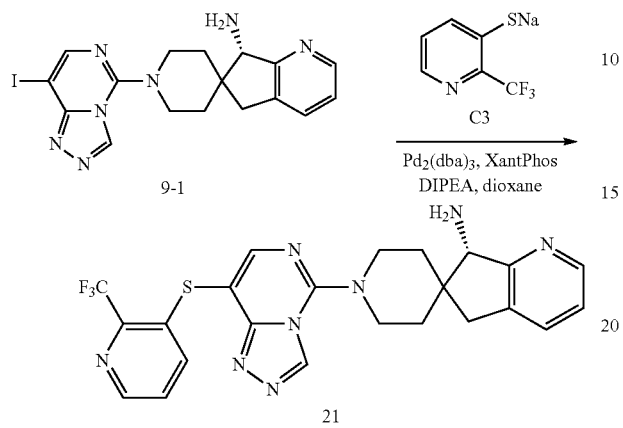

(S)-1'-(8-iodo[1,2,4]triazolo[4,3-c]pyrimidin-5-yl)-5,7-dihydrospiro[cyclopenta[b]pyridine-6,4'-piperidine]-7-amine (9-1, 100 mg, 0.22 mmol) was dissolved in 1,4-dioxane (12 mL), and DIPEA (300 mg, 2.32 mmol) and sodium 2-(trifluoromethyl)pyridine-3-mercaptan (C3, 200 mg, crude product) were added. XantPhos (100 mg, 0.17 mmol) and Pd$_2$(dba)$_3$ (100 mg, 0.11 mmol) were added under the protection of nitrogen. After the the atmosphere in the reaction system was replaced with nitrogen for three times, the mixture was reacted at 100° C. for 3 hours, and the reaction was completed. The reaction solution was passed through the column (EA:MeOH=5/1, 0.5% of ammonium hydroxide) to obtain (S)-1'-(8-((2-(trifluoromethyl)pyridin-3-yl)thio)-[1,2,4]-triazolo[4,3-c]pyrimidin-5-yl)-5,7-dihydrospiro[cyclopenta[b]pyridine-6,4'-piperidine]-7-amine (compound 21, 35 mg, yield: 31%) as a white solid. LCMS: m/z 499.1 [M+H]$^+$ $^1$H NMR (400 MHz, MeOD) δ 9.32 (s, 1H), 8.41-8.37 (m, 2H), 8.03 (s, 1H), 7.72 (d, J=7.6 Hz, 1H), 7.60 (d, J=8.4 Hz, 1H), 7.38-7.35 (m, 1H), 7.28-7.25 (m, 1H), 4.18-4.14 (m, 2H), 4.04 (s, 1H), 3.62-3.59 (m, 2H), 3.23 (d, J=16.4 Hz, 1H), 2.90 (d, J=16.4 Hz, 1H), 2.11-2.06 (m, 2H), 1.79-1.75 (m, 1H), 1.56-1.53 (m, 1H).

Example 22: Synthesis of Compound 22

(S)-1'-(8-((2-amino-3-chloropyridin-4-yl)thio)imidazo[1,5-c]pyrimidin-5-yl)-2-chloro-4,6-dihydrospiro[cyclopenta[d]thiazole-5,4'-piperidine]-4-amine

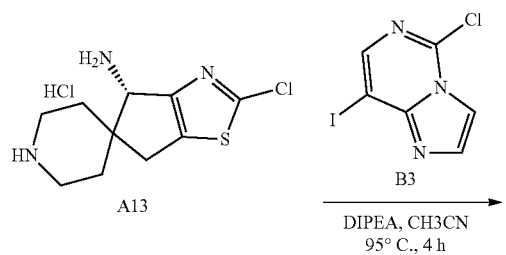

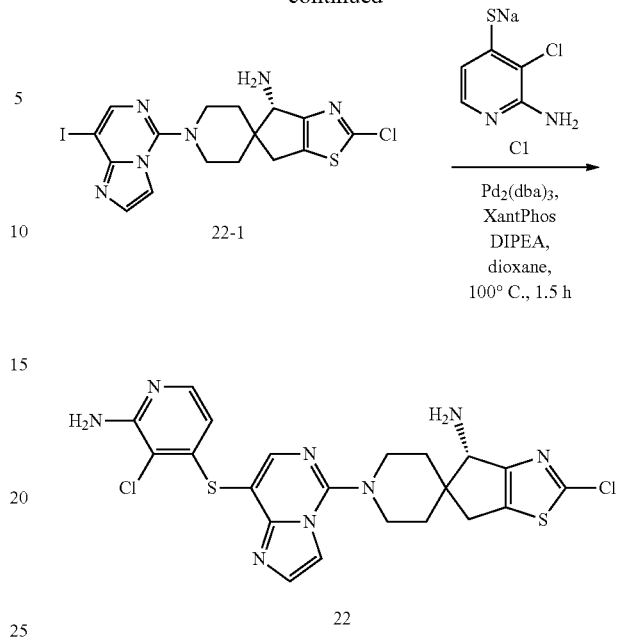

Step 1: (S)-2-chloro-4,6-dihydrospiro[cyclopenta[d]thiazole-5,4'-piperidine]-4-amine hydrochloride (A13, 155 mg, 0.35 mmol) was dissolved in acetonitrile (10 mL), and DIPEA (450 mg, 3.5 mmol) and 5-chloro-8-iodoimidazo[1,2-c]pyrimidine (B3, 108 mg, 0.39 mmol) were added, the mixture was heated to 100° C. and refluxed for 5 hours under the protection of nitrogen, and the reaction was completed. The reaction solution was cooled to room temperature, poured into saturated sodium bicarbonate aqueous solution and extracted with dichloromethane (50 mL×2). The organic phases were combined, and then washed with saturated brine. The organic phase was separated, and then dried over anhydrous sodium sulfate, filtered and concentrated. The crude product was purified by silica gel chromatography to obtain (S)-2-chloro-1'-(8-iodoimidazo[1,2-c]pyrimidin-5-yl)-4,6-dihydrospiro[cyclopenta[d]thiazole-5,4'-piperidine]-4-amine (22-1, 72 mg, yield: 43%) as a light yellow solid. LCMS: m/z 487 [M+H]$^+$ Step 2: (S)-2-chloro-1'-(8-iodoimidazo[1,2-c]pyrimidine-5-yl)-4,6-dihydrospiro[cyclopenta[d]thiazole-5,4'-piperidine]-4-amine (22-1, 50 mg, 0.1 mmol) was dissolved in 1,4-dioxane (5 mL), and DIPEA (30 mg, 0.25 mmol) and sodium 2-amino-3-chloropyridine-4-mercaptan (C1, 30 mg, 0.15 mmol) were added. XantPhos (13 mg, 0.02 mmol) and Pd$_2$(dba)$_3$ (20 mg, 0.02 mmol) were added under the protection of nitrogen. After the the atmosphere in the reaction system was replaced with nitrogen for three times, the mixture was reacted at 100° C. for 3 hours. The reaction solution was concentrated and then purified by high performance liquid chromatography to obtain (S)-1'-(8-((2-amino-3-chloropyridin-4-yl)thio)imidazo[1,2-c]pyrimidin-5-yl)-2-chloro-4,6-dihydrospiro[cyclopenta[d]thiazole-5,4'-piperidine]-4-amine (compound 22, 3 mg, yield: 5%) as a light yellow solid. LCMS: m/z 519 [M+H]$^+$ 1H NMR (400 MHz, MeOD) δ 8.06 (s, 1H), 7.85 (s, 1H), 7.57 (s, 1H), 7.50-7.49 (d, 1H), 5.89-5.87 (d, 1H), 4.15 (s, 1H), 4.07-3.99 (dd, 2H), 3.53-3.39 (m, 4H), 3.11-3.09 (d, 2H), 2.21-2.04 (m, 4H)

Example 23: Synthesis of Compound 23

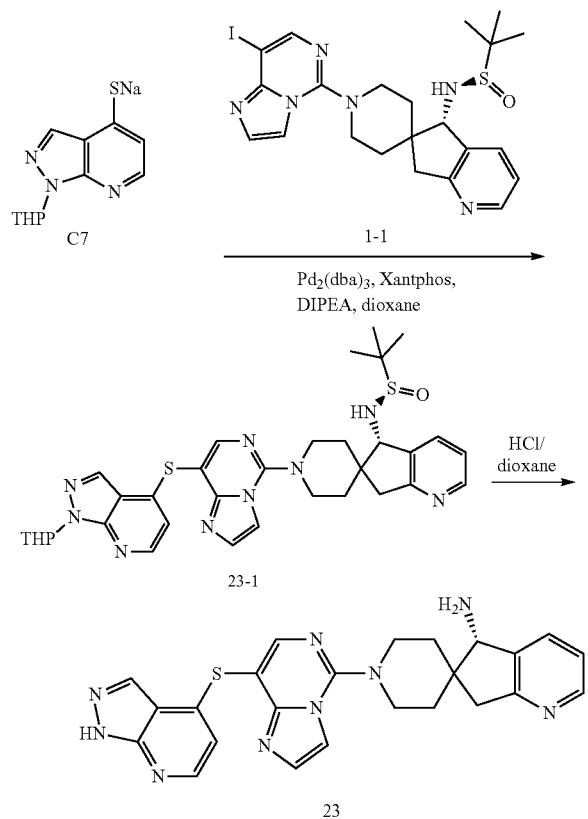

Step 1: Dioxane (20 mL) was added to sodium 1-(tetrahydro-2H-pyran-2-yl)-1H-pyrazolo[3,4-b]pyridine-4-mercaptan (C7, 224 mg, 0.8 mmol) in a reaction flask, and then (S)—N—((S)-1'-(8-iodoimidazolo[1,2-C]pyrimidin-5-yl)-5,7-dihydrospiro[cyclopentane[B]pyridine-6,4'-piperidin]-5-yl)-2-methylpropane-2-sulfinamide (1-1, 287 mg, 0.52 mmol), DIPEA (304 mg, 2.35 mmol), XantPhos (91 mg, 0.16 mmol) and Pd$_2$(dba)$_3$ (72 mg, 0.08 mmol) were added. The mixture was heated to 100° C. and stirred for 3 h under the protection of nitrogen, and TLC (dichloromethane/methanol=20/1) and LCMS indicated the reaction was completed. The reaction solution was diluted with ethyl acetate and filtered. The filter residue was eluted with ethyl acetate. The filtrate was concentrated to dry and purified by silica gel chromatography to obtain (R)-2-methyl-N-((5 S)-1'-((8-((1-(tetrahydro-2H-pyran-2-yl)-1H-pyrazolo[3,4-b]pyridin-4-yl)thio)imidazo[1,2-c]pyrimidin-5-yl)-5,7-dihydrospiro[cyclopentadiene[b]pyridine-6,4'-piperidine]-5-yl)propane-2-sulfinamide (23-1, 352 mg, yield: 97.2%).

LCMS: m/z 658.4 [M+H]$^+$

Step 6: Under the protection of nitrogen, HCl/dioxane (4 M, 1.3 mL, 5.20 mmol) was slowly added to a solution of (R)-2-methyl-N-((5 S)-1'-((8-((1-(tetrahydro-2H-pyran-2-yl)-1H-pyrazolo[3,4-b]pyridin-4-yl)thio)imidazo[1,2-c]pyrimidin-5-yl)-5,7-dihydrospiro[cyclopentadiene[b]pyridine-6,4'-piperidin]-5-yl)propane-2-sulfinamide (23-1, 176 mg, 0.26 mmol) in dichloromethane (10 mL) at 0° C., the mixture was stirred at room temperature for 2 h, and TLC (dichloromethane/methanol=8/1) and LCMS indicated the reaction was completed. The reaction solution was cooled to 0° C., ammonia methanol solution was slowly added to adjust the PH to about 10, and then the mixture was concentrated under reduced pressure and purified by prep-TLC to obtain (S)-1'-(8-(((1H-pyrazolo[3,4-b]pyridin-4-yl]thio]imidazo[1,2-c]pyrimidin-5-yl)-5,7-dihydrospiro[cyclopentadiene[b]pyridine-6,4'-piperidine]-5-amine (23, 73.01 mg, yield: 58.1%). LCMS: m/z 470.5 [M+H]$^+$ $^1$HNMR (400 MHz, MeOD): δ 8.42 (d, J=4.0 Hz, 1H), 8.16~8.14 (m, 2H), 8.10 (s, 1H), 7.91~7.87 (m, 2H), 7.56 (d, J=1.2 Hz, 1H), 7.34~7.31 (m, 1H), 4.26 (s, 1H), 4.11~4.06 (m, 1H), 3.49~3.43 (m, 2H), 3.28 (s, 1H), 3.07 (d, J=16.8 Hz, 1H), 2.15~2.07 (m, 2H), 1.76 (d, J=12.8 Hz, 2H), 1.64 (d, J=13.6 Hz, 2H).

Synthesis of Control Compound: At the Time of Application of the Disclosure, the Closest Control Compound to the Disclosure is Example 25 of WO2018136265. According to the Synthetic Route and Operation Steps of Example 25 of WO2018136265, the Control Compound AA was Obtained

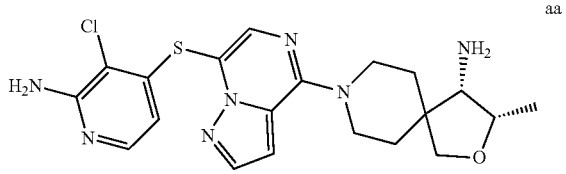 [SMILES: C[C@@H]1OCC2(CCN(c3ncc(Sc4ccnc(N)c4Cl)n4nccc34)CC2)[C@@H]1N]

The biological function of the compound of the disclosure has been proved by the tests on enzyme activity and at the cellular level. For example, in the SHP2 enzyme activity inhibition test, the compound of the disclosure can achieve strong inhibition activity (IC50 can reach 1 nM). At the cellular level, the compound of the disclosure also showed a very good activity on inhibiting the proliferation of cancer cells, and the inhibitory activity on the proliferation of MV4-11 cell line can reach 1 nM. Compared with SHP099 (6-(4-amino-4-methylpiperidine-1-yl)-3-(2,3-dichlorophenyl)pyrazine-2-amine) or the control compound aa, the compound of the disclosure showed superior activity both at the enzymatic level and at the cellular level.

Test Example 1: Test Method of SHP2 Enzyme Activity

Test Method of SHP2 Enzyme Activity:

Compound powder was dissolved in DMSO to make mother liquor. During the experiment, the compound stock solution was diluted with DMSO by 3-fold gradient, and 10 different test concentrations were set for each compound. 1 μL of the compounds at each concentration point was put into the well of the detection plate (Corning, Costa 3915), and each concentration was tested in two replicates. 6,8-difluoro-4-methyl-7-hydroxycoumarin phosphate (DiFMUP) was used as the substrate, and it can be hydrolyzed under the catalysis of SHP2 E72A to produce 6,8-difluoro-4-methyl-7-hydroxycoumarin (DiFMU). To determine the enzyme activity of SHP2, the fluorescence value at 455 nm was detected by PE Enspire multifunctional reader using an excitation wavelength of 358 nm.

The SHP2 buffer for the reaction consisted of 60 mmol/L Hepes, PH7.2, 75 mmol/L NaCl, 75 mmol/L KCl, 1 mmol/L EDTA, 5 mmol/L DTT.

The screening system consisted of SHP2 buffer, enzyme SHP2 E76A protein, substrate DiFMUP and test compounds.

Test Method of IC50:

In a 96-well screening plate, 50 ng SHP2 E76A protein was reacted with the test compound in SHP2 buffer for 20 min, and then incubated with 10 uM DiFMUP at room temperature for 20 min. The light intensity at 455 nm was read by PE Enspire multifunction reader with an excitation light of 358 nm. The inhibition rate of the sample on the enzyme activity was calculated as the ratio of the measured fluorescence value of the compound treatment group to that of the DMSO control well. IC50 values of the compounds were calculated using Graphpad's Prism software by non-linearly fitting the inhibition rate to the concentration of the inhibitor. The curve of enzyme activity as a function of compound concentration was fitted through the equation $Y = Bottom + (Top - Bottom)/(1 + 10^{((LogIC50-X)*HillSlope)})$. An IC50 value of each compound was calculated. Table 1 shows IC50 values of some compounds of the disclosure.

TABLE 1

| Compound number | Enzyme activity (nM) | Compound number | Enzyme activity (nM) |
|---|---|---|---|
| SHP099 | 263 | Compound 12 | 2 |
| Positive control aa | 26 | Compound 13 | 1 |
| Compound 1 | 11 | Compound 14 | 8 |
| Compound 2 | 4 | Compound 15 | 3 |
| Compound 3 | 11 | Compound 16 | 2 |
| Compound 4 | 7 | Compound 17 | 10 |
| Compound 5 | 5 | Compound 18 | 7 |
| Compound 6 | 6 | Compound 19 | 7 |
| Compound 7 | 3 | Compound 20 | 6 |
| Compound 8 | 10 | Compound 21 | 11 |
| Compound 9 | 7 | Compound 22 | 9 |
| Compound 10 | 3 | Compound 23 | 9 |
| Compound 11 | 1 | | |

Test Example 2: MV4-11 Cell Proliferation Inhibition Experiment

The number of living cells in the culture was determined by quantitative determination of intracellular ATP using CellTiter-Glo® Luminescent Cell Viability Assay kit.

In the first step, MV4-11 cells were inoculated into 96-well plates with a density of 2500 cells per well and a volume of 100 μL per well. The plates were placed in 37° C., 5% carbon dioxide incubator overnight.

In the second step, cells were treated with compounds. The compounds to be tested were diluted 3 times, and 8 concentration gradients were set up. Each well was added with a certain volume of DMSO or the compound to be tested, and each concentration was tested in 2 replicates, and the final concentration of DMSO was 0.5%. The plates were placed in 37° C., 5% carbon dioxide incubator for 72 h.

In the third step, cell viability of the control groups and the treatment groups was determined using CellTiter-Glo® Luminescent Cell Viability Assay kit (Promega, G7570). Each well was added with 50 uL CellTiter-Glo. The culture was mixed well, and incubated at room temperature for 10 min. Signals were read using EnSpire (Perkin Elmer). Inhibition percentages (%) were calculated by the following formula:

Inhibition percentage (%)=(1−signal value of compound treatment group/signal value of DMSO treatment group)*100.

The results are shown in Table 2.

TABLE 2

| Compound number | Cell proliferation inhibition activity (nM) | Compound number | Cell proliferation inhibition activity (nM) |
|---|---|---|---|
| SHP099 | 1600 | Compound 10 | 7 |
| Positive control aa | 423 | Compound 11 | 30 |
| Compound 1 | 68 | Compound 12 | 30 |
| Compound 2 | 11 | Compound 13 | 1 |
| Compound 3 | 99 | Compound 14 | 36 |
| Compound 4 | 7 | Compound 15 | 94 |
| Compound 5 | 6 | Compound 16 | 52 |
| Compound 6 | 4 | Compound 17 | 35 |
| Compound 7 | 29 | Compound 18 | 42 |
| Compound 8 | 33 | Compound 19 | 1 |
| Compound 9 | 60 | | |

Test Example 3: Pharmacokinetics Experiment of Compound

Pharmacokinetics of the compound of the disclosure was determined. The following method was used to determine the pharmacokinetic parameters of the compound of the disclosure.

Healthy male adult mice were used in the study. Each group was intragastrically administered with a single dose of 5-100 mg/kg. Fasting lasted from 10 hours before administration to 4 hours after administration. Blood samples were collected at different time points after administration and the compound content in plasma was determined by LC-MS/MS. The relationship between plasma concentration and time was analyzed by professional software (winnonlin), and the pharmacokinetic parameters of the compounds were calculated. According to Table 3, the compounds of the disclosure have excellent pharmacokinetic properties.

TABLE 3

| Compound number | Oral administration dosage (mg/Kg) | Plasma exposure AUC: uM * hr | Maximum plasma concentration Cmax:uM | Half-life $T_{1/2}$:hr | Oral bioavailability % |
|---|---|---|---|---|---|
| 4 | 5 | 29 | 7 | 5.4 | 34 |
| 6 | 5 | 35 | 6 | 3.1 | 37 |
| 7 | 5 | 43 | 7.5 | 3 | 98 |
| 10 | 5 | 48 | 5 | 3.8 | 51 |
| 18 | 5 | 40 | 6.5 | 3.5 | 72 |

All publications mentioned herein are cited by reference in the present disclosure to the same extent as if each publication is separately cited by reference. The preferred embodiments of the present disclosure are described in detail above, but the disclosure is not limited to the specific details in the above embodiments. Within the scope of the technical concept of the present disclosure, a variety of simple modifications can be made to the technical solutions of the disclosure, and all of the modifications fall within the scope of the disclosure.

In addition, it should be noted that each specific technical feature described in the above specific embodiments can be combined in any suitable way without contradiction. In order to avoid unnecessary duplication, the present disclosure does not separately describe the various possible combinations. In addition, various different embodiments of the present disclosure can also be combined in any way, and the

What is claimed is:
1. A compound, which is:
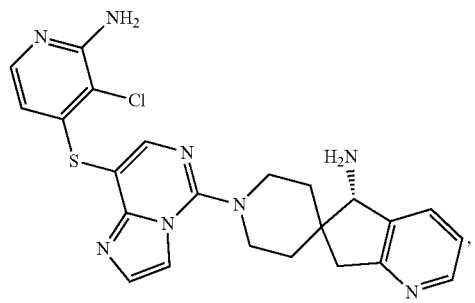 [SMILES: Nc1nccc(Sc2cnc(N3CCC4(CC3)Cc3ncccc3[C@H]4N)n3ccnc23)c1Cl]
or a pharmaceutically acceptable salt thereof.
2. A compound, which is:
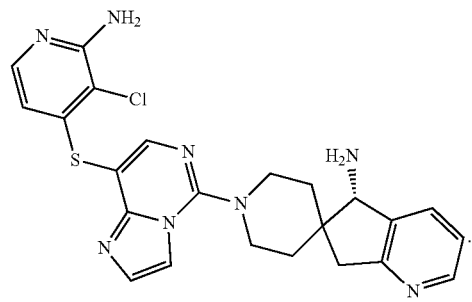 [SMILES: Nc1nccc(Sc2cnc(N3CCC4(CC3)Cc3ncccc3[C@H]4N)n3ccnc23)c1Cl]
* * * * *